US009339533B2

(12) United States Patent
Beck et al.

(10) Patent No.: US 9,339,533 B2

(45) Date of Patent: May 17, 2016

(54) **MODIFIED LIVE VACCINE OF *MYCOPLASMA BOVIS*, METHODS OF PRODUCING MODIFIED LIVE *MYCOPLASMA BOVIS* VACCINES, COMBINATION VACCINES AND METHODS OF TREATMENT**

(75) Inventors: Michael Beck, Saint Joseph, MO (US); Jeffrey Knittel, Saint Joseph, MO (US)

(73) Assignee: Boehringer Ingelheim Vetmedica, Inc., St. Joseph, MO (US)

(*) Notice: Subject to any disclaimer, the term of this patent is extended or adjusted under 35 U.S.C. 154(b) by 644 days.

(21) Appl. No.: 12/766,084

(22) Filed: Apr. 23, 2010

(65) Prior Publication Data

US 2010/0272759 A1 Oct. 28, 2010

Related U.S. Application Data

(60) Provisional application No. 61/172,543, filed on Apr. 24, 2009.

(51) Int. Cl.

*A61K 39/02* (2006.01)
*A61K 49/00* (2006.01)
*A61K 39/00* (2006.01)

(52) U.S. Cl.

CPC ....... *A61K 39/0241* (2013.01); *A61K 2039/522* (2013.01)

(58) Field of Classification Search

None

See application file for complete search history.

(56) References Cited

U.S. PATENT DOCUMENTS

| | | | | |
|---|---|---|---|---|
| 6,248,329 | B1 * | 6/2001 | Chandrashekar et al. | 424/191.1 |
| 6,548,069 | B2 | 4/2003 | Hymas et al. | |
| 7,429,389 | B2 | 9/2008 | Leonard et al. | |
| 2002/0150593 | A1 | 10/2002 | Hymas et al. | |
| 2003/0064079 | A1 | 4/2003 | Goudie et al. | |
| 2003/0147914 | A1 | 8/2003 | Keich et al. | |
| 2003/0180219 | A1 | 9/2003 | Keich et al. | |
| 2005/0053627 | A1 | 3/2005 | Leonard et al. | |
| 2007/0077260 | A1 | 4/2007 | Leonard et al. | |
| 2008/0069842 | A9 | 3/2008 | Leonard et al. | |
| 2008/0193463 | A1 | 8/2008 | Frey et al. | |
| 2008/0226671 | A1 | 9/2008 | Leonard et al. | |
| 2009/0068231 | A1 | 3/2009 | Kumar et al. | |
| 2009/0130148 | A1 * | 5/2009 | Beck et al. | 424/264.1 |
| 2010/0272759 | A1 | 10/2010 | Beck et al. | |
| 2011/0059437 | A1 | 3/2011 | Beck | |
| 2012/0093854 | A1 | 4/2012 | Beck et al. | |

FOREIGN PATENT DOCUMENTS

| | | | |
|---|---|---|---|
| WO | 9902670 | A1 | 1/1999 |
| WO | 9964604 | A2 | 12/1999 |
| WO | 0134189 | A2 | 5/2001 |
| WO | 03004051 | A2 | 1/2003 |
| WO | 03004052 | A1 | 1/2003 |
| WO | 03017755 | A2 | 3/2003 |
| WO | 2005111201 | A1 | 11/2005 |
| WO | 2008030619 | A2 | 3/2008 |
| WO | 2009036241 | A1 | 3/2009 |
| WO | 2009058833 | A2 | 5/2009 |
| WO | 2010002537 | A1 | 1/2010 |
| WO | 2010051210 | A1 | 5/2010 |
| WO | 2010124154 | A1 | 10/2010 |

OTHER PUBLICATIONS

International Search Report for PCT/US2010/032149 mailed Aug. 5, 2010.

Mostowy et al., "The in vitro evolution of BCG vaccines". 2003, Vaccine, vol. 21, pp. 4270-4274.

Rosengarten et al. "Antigen Heterogeneity among Isolates of Mycoplasma bovis Is Generated by High-Frequency Variation of Diverse Membrane Surface Proteins". Nov. 1994, Infection and Immunity, vol. 62, No. 11, pp. 5066-5074.

Thorns, et al., "Effect of Serial Passages Through Liquid Medium on the Virulence of Mycoplasma-Bovis for the Mouse Mammary Gland", Research in Veterinary Science, vol. 29, No. 3, 1980 pp. 328-332.

Written Opinion of the International Search Authority for PCT/US2010/032149 mailed Aug. 5, 2010.

Alberti et al., "Molecular and antigenic characterization of a Mycoplasma bovis strain causing an outbreak of infectious keratoconjunctivitis". 2006, Journal of Veterinary Diagnostic Investigation, vol. 18, pp. 41-51.

Angen et al., "Respiratory disease in calves: Microbiological investigations on trans-tracheally aspirated bronchoalveolar fluid and acute phase protein response". 2009, Veterinary Microbiology, vol. 137, pp. 165-171.

Boddie et al., "Germicidal Activities of Representatives of Five Different Teat Dip Classes Against Three Bovine Mycoplasma Species Using a Modified Excised Teat Model". 2002, Journal of Dairy Science, vol. 85, pp. 1909-1912.

Boothby et al., "Immune Responses to Mycoplasma bovis Vaccination and Experimental Infection in the Bovine Mammary Gland". 1988, Canadian Journal of Veterinary Research, vol. 52, pp. 355-359.

Brank et al., "Development of a Recombinant Antigen for Antibody-Based Diagnosis of Mycoplasma bovis Infection in Cattle". Nov. 1999, Clinical and Diagnostic Laboratory Immunology, vol. 6, No. 6, pp. 861-867.

Bush et al., "Characterization of a lympho-inhibitory peptide produced by Mycoplasma bovis". 2004, Biochemical and Biophysical Research Communications, vol. 315, pp. 336-341.

Butler et al., "Pasteurization of Discard Mycoplasma Mastitic Milk Used to Feed Calves: Thermal Effects on Various Mycoplasma". 2000, Journal of Dairy Science, vol. 83, pp. 2285-2288.

(Continued)

*Primary Examiner* — Rodney P Swartz

(74) *Attorney, Agent, or Firm* — Michael P. Morris; Joyce L. Morrison

(57) ABSTRACT

The present invention relates to new attenuated *M. bovis* bacteria strains passaged at least 110 times. Moreover, the present invention also provides immunogenic compositions comprising live bacteria of any of those attenuated *M. bovis* bacteria strain, their manufacture and use for the treatment and prophylaxis of *M. bovis* infections and combinations with other veterinary vaccines or medicaments.

24 Claims, 6 Drawing Sheets

(56) References Cited

OTHER PUBLICATIONS

Byrne et al., "Mycoplasma bovis arthritis as a sequel to respiratory disease in bought-in weanling cattle in the Republic of Ireland". Oct. 2001, Irish Veterinary Journal, vol. 54(10), pp. 516-519.
Cai et al., "Development of a real-time PCR for detection of Mycoplasma bovis in bovine milk and lung samples". 2005, Journal of Veterinary Diagnostic Investigation, vol. 17, pp. 537-545.
Caswell et al., "Mycoplasma bovis pneumonia in cattle". 2008, Animal Health Research Reviews, vol. 8(2), pp. 161-186.
Chima et al., "Immunoprophylaxis of Experimental Mycoplasma Bovis Arthritis in Calves. Protective Efficacy of Live Organisms and Formalinized Vaccines". 1980, Veterinary Microbiology, vol. 5, pp. 113-122.
Devriese et al., "Antibiotic Susceptibility Testing of Mycoplasma bovis using Tween 80 Hydrolysis as an Indicator of Growth". 1991, Journal of Veterinary Medicine B, vol. 38, pp. 781-783.
Duarte et al., "Otitis in Cattle, an Aetiological Review". 2004, Journal of Veterinary Medicine B, vol. 51, pp. 1-7.
Gagea et al., "Diseases and pathogens associated with mortality in Ontario beef feedlots". 2006, Journal of Veterinary Diagnostic Investigation, vol. 18, pp. 18-28.
Gagea et al., "Naturally occurring Mycoplasma bovis—associated pneumonia and polyarthritis in feedlot beef calves". 2006, Journal of Veterinary Diagnostic Investigation, vol. 18, pp. 29-40.
Geary et al., "Inflammatory Toxin from Mycoplasma bovis: Isolation and Characterization". May 1981, Science, vol. 212, pp. 1032-1033.
Ghadersohi et al., "Development of a monoclonal blocking ELISA for the detection of antibody to Mycoplasma bovis in dairy cattle and comparison to detection by PCR". 2005, Veterinary Immunology and immunopathology, vol. 104, pp. 183-193.
Gourlay et al., "Experimental pneumonia in conventionally reared and gnotobiotic calves by dual infection with Mycoplasma bovis and Pasteurella haemolytica". 1985, Research in Veterinary Science, vol. 28, pp. 377-382.
Hannan et al., "Comparative Susceptibilities of Various Animal-Pathogenic Mycoplasmas to Fluoroquinolones". 1997, Antimicrobial Agents and Chemotherapy, vol. 41, No. 9, pp. 2037-2040.
Hannan, P., "Guidelines and recommendations for antimicrobial minimum inhibitory concentration (MIC) testing against veterinary mycoplasma species". 2000, Veterinary Research, vol. 31, pp. 373-395.
Howard et al., Comparative Pathogenicity of Mycoplasma bovis and Mycoplasma Dispar for the Respiratory Tract of Calves. 1987, Israel Journal of Medical Sciences, vol. 23, pp. 621-624.
International Search Report for PCT/US2008/81545 mailed Apr. 15, 2009.
International Search Report for PCT/US20091/61610 mailed Jan. 15, 2010.
Khan et al., "Biochemical characterisation of some non fermenting, non arginine hydrolysing mycoplasmas of ruminants". 2005, Veterinary Microbiology, vol. 109, pp. 129-134.
Khodakaram-Tafti et al., "Immunohistopathological Findings in the Lungs of Calves Naturally Infected with Mycoplasma bovis". 2004, Journal of Veterinary Medicine A, vol. 51, pp. 10-14.
Krysak, D., "Chronic pneumonia and polyarthritis syndrome in a feedlot calf". Oct. 2006, Canadian Veterinary Journal, vol. 47, pp. 1019-1022.
Lin et al., "A rapid chromogenic microtitre assay of arginine aminopeptidase activity in Mycoplasma strains". 2006, Systematic and Applied Microbiology, vol. 29, pp. 589-592.
Lysnyansky et al., "Juxtaposition of an Active Promoter to vsp Genes via Site-Specific DNA Inversions Generates Antigenic Variation in Mycoplasma bovis". Oct. 2001, Journal of Bacteriology, vol. 183, No. 19, pp. 5698-5708.
Lysnyansky et al., "Molecular characterization of the Mycoplasma bovis p68 gene, encoding a basic membrane protein with homology to P48 of Mycoplasma agalactiae". 2008, FEMS Microbiology Letters, vol. 279, pp. 234-242.
Madoff et al., "Isolation of Mycoplasma bovis from a Patient with Systemic Illness". Jun. 1979, Journal of Clinical Microbiology, vol. 9, No. 6, pp. 709-711.
Maunsell et al., "Mycoplasa bovis Infections in Young Calves". 2009, Vet Clin Food Anim, vol. 25, pp. 139-177.
Miles et al., "Insertion sequence profiling of UK Mycoplasma bovis field isolates". 2005, Veterinary Microbiology, vol. 107, pp. 301-306.
Nicholas et al., "An experimental vaccine for calf pneumonia caused by Mycoplasma bovis: clinical, cultural, serological and pathological findings". 2002, Vaccine, vol. 20, pp. 3569-3575.
Nicholas et al., "Mycoplasmas in Adult Cattle: Bugs Worth Bothering with?". 2005, British Cattle Veterinary Association, vol. 13, Part 2, pp. 167-170.
Nicholas et al., "Vaccines for Mycoplasma Diseases in Animals and Man". 2009, Journal of Comparative Pathology, vol. 140, pp. 85-96.
Pfuetzner et al., "Mycoplasma bovis as an agent of mastitis, pneumonia, arthritis and genital disorders in cattle". 1996, Rev. sci. tech. Off. int. Epiz., vol. 15(4), pp. 1477-1494.
Razin et al., "Molecular Biology and Pathogenicity of Mycoplasmas". Dec. 1998, Microbiology and Molecular Biology Reviews, vol. 62, No. 4, pp. 1094-1156.
Rodriguez et al., "Immunohistochemical Characterization of Lung Lesions Induced Experimentally by Mycoplasma agalactiae and Mycoplasma bovis in Goats". 2000, Journal of Comparative Pathology, vol. 123, pp. 285-293.
Rosenbusch et al., "In vitro antimicrobial inhibition profiles of Mycoplasma bovis isolates recovered from various regions of the United States from 2002 to 2003". 2005, Journal of Veterinary Diagnostic Investigation, vol. 17, pp. 436-441.
Sachse et al., "Comparison of Mycoplasma bovis Strains Based on SDS-PAGE and Immunoblot Protein Patterns". 1992, Journal of Veterinary Medicine B, vol. 39, pp. 246-252.
Stalheim et al., "Naturally Occurring and Experimentally Induced Mycoplasmal Arthritis of Cattle". Sep. 1975, Journal of Clinical Microbiology, vol. 2, No. 3, pp. 165-168.
Tenk et al., "Detection of Mycoplasma Bovis with an Improved PCR Assay". 2006, Acta Veterinaria Hungarica, vol. 54(4), pp. 427-435.
Thomas et al., "Adherence of Mycoplasma bovis to bovine bronchial epithelial cells". 2003, Microbial Pathogenesis, vol. 34, pp. 141-148.
Thomas et al., "Adherence to various host cell lines of Mycoplasma bovis strains differing in pathogenic and cultural features". 2003, Veterinary Microbiology, vol. 91, pp. 101-113.
Thomas et al., "The p40* adhesin pseudogene of Mycoplasma bovis". 2004, Veterinary Microbiology, vol. 104, pp. 213-217.
Vicca et al., "In Vitro Susceptibilities of Mycoplasma hyopneumoniae Field Isolates". Nov. 2004, Antimicrobial Agents and Chemotherapy, vol. 48, No. 11, pp. 4470-4472.
Zhang et al., "Attenuated Mycoplasma bovis strains provide protection against avirulent infection in calves". Vaccine, 2014, 8 pages. [Accessed at: http://dx.doi.org/10.1016/j.vaccine.2013.12.004].

* cited by examiner

SEQUENCE LISTING

```
<160> NUMBER OF SEQ ID NOS: 52

<210> SEQ ID NO 1
<211> LENGTH: 21
<212> TYPE: DNA
<213> ORGANISM: Mycoplasma bovis

<400> SEQUENCE: 1

ccgcaagtta acttgtggtg c                                              21


<210> SEQ ID NO 2
<211> LENGTH: 24
<212> TYPE: DNA
<213> ORGANISM: Mycoplasma bovis

<400> SEQUENCE: 2

ggccattttc ttgtcagaac cacc                                           24


<210> SEQ ID NO 3
<211> LENGTH: 29
<212> TYPE: DNA
<213> ORGANISM: Mycoplasma bovis

<400> SEQUENCE: 3

gcttttactc tggtactaga tggtcttgg                                      29


<210> SEQ ID NO 4
<211> LENGTH: 30
<212> TYPE: DNA
<213> ORGANISM: Mycoplasma bovis

<400> SEQUENCE: 4

gtggcgttct tgacaataga acaattagtg                                     30


<210> SEQ ID NO 5
<211> LENGTH: 26
<212> TYPE: DNA
<213> ORGANISM: Mycoplasma bovis

<400> SEQUENCE: 5

gatgttcttc attgtctttt gcatcg                                         26


<210> SEQ ID NO 6
```

-continued

<211> LENGTH: 23
<212> TYPE: DNA
<213> ORGANISM: Mycoplasma bovis

<400> SEQUENCE: 6
cgacgagtta caagaaagtt ggc 23

<210> SEQ ID NO 7
<211> LENGTH: 29
<212> TYPE: DNA
<213> ORGANISM: Mycoplasma bovis

<400> SEQUENCE: 7
gaaacaccta tcccagtagg tacaagatc 29

<210> SEQ ID NO 8
<211> LENGTH: 33
<212> TYPE: DNA
<213> ORGANISM: Mycoplasma bovis

<400> SEQUENCE: 8
gtctacattg ttcaaaatgc gacattttgt ata 33

<210> SEQ ID NO 9
<211> LENGTH: 60
<212> TYPE: DNA
<213> ORGANISM: Mycoplasma bovis

<400> SEQUENCE: 9
cgcccgttta gctattggta caattaactt ctcgcttgca gttgaaggcc aaagaattga 60

<210> SEQ ID NO 10
<211> LENGTH: 60
<212> TYPE: DNA
<213> ORGANISM: Mycoplasma bovis

<400> SEQUENCE: 10
cgcccgttta gctattggta caattaactt ctcgcttgca gttgaaggcc aaataattga 60

<210> SEQ ID NO 11
<211> LENGTH: 60
<212> TYPE: PRT
<213> ORGANISM: Mycoplasma bovis

<400> SEQUENCE: 11

```
Leu Val Asn Thr Lys Tyr Lys Asn Trp Asp Trp Asn Tyr Gly Leu Ser
1               5                   10                  15

Pro Arg Tyr Glu Tyr Asn Arg Asp Ala Arg Leu Ala Ile Gly Thr Ile
            20                  25                  30

Asn Phe Ser Leu Ala Val Glu Gly Gln Arg Ile Glu Lys Ile Lys Ile
        35                  40                  45

Ser Gly Asp Phe Phe Ala Lys Lys Asp Ile Thr Glu
    50                  55                  60
```

<210> SEQ ID NO 12
<211> LENGTH: 60
<212> TYPE: PRT
<213> ORGANISM: Mycoplasma bovis

<400> SEQUENCE: 12

```
Leu Val Asn Thr Lys Tyr Lys Asn Trp Asp Trp Asn Tyr Gly Leu Ser
1               5                   10                  15
```

```
Pro Arg Tyr Glu Tyr Asn Arg Asp Ala Arg Leu Ala Ile Gly Thr Ile
            20                  25                  30

Asn Phe Ser Leu Ala Val Glu Gly Gln Ile Ile Glu Lys Ile Lys Ile
        35                  40                  45

Ser Gly Asp Phe Phe Ala Lys Lys Asp Ile Thr Glu
    50                  55                  60


<210> SEQ ID NO 13
<211> LENGTH: 35
<212> TYPE: DNA
<213> ORGANISM: Mycoplasma bovis

<400> SEQUENCE: 13

attcataaac cattgaattt gctaggggag tcatt                               35


<210> SEQ ID NO 14
<211> LENGTH: 35
<212> TYPE: DNA
<213> ORGANISM: Mycoplasma bovis

<400> SEQUENCE: 14

attcataaac cattaaattt gctaggggag tcatt                               35


<210> SEQ ID NO 15
<211> LENGTH: 60
<212> TYPE: PRT
<213> ORGANISM: Mycoplasma bovis

<400> SEQUENCE: 15

Ile His Lys Pro Leu Asn Leu Leu Gly Glu Ser Leu Asn Lys Glu Ala
1               5                   10                  15

Phe Ser Ser Ile Asn Asp Ile Asp Cys Ile Leu Phe Leu Thr Pro Val
            20                  25                  30

Asn Glu Glu Ile Lys Ser Gly Asp Lys Leu Ile Leu Glu Arg Ile Ala
        35                  40                  45

Asn Ser Lys Asn Lys Ile Ala Val Ile Ser Lys Ile
    50                  55                  60


<210> SEQ ID NO 16
<211> LENGTH: 60
<212> TYPE: PRT
<213> ORGANISM: Mycoplasma bovis

<400> SEQUENCE: 16

Ile His Lys Pro Leu Asn Leu Leu Gly Glu Ser Leu Asn Lys Glu Ala
1               5                   10                  15

Phe Ser Ser Ile Asn Asp Ile Asp Cys Ile Leu Phe Leu Thr Pro Val
            20                  25                  30

Asn Glu Glu Ile Lys Ser Gly Asp Lys Leu Ile Leu Glu Arg Ile Ala
        35                  40                  45

Asn Ser Lys Asn Lys Ile Ala Val Ile Ser Lys Ile
    50                  55                  60


<210> SEQ ID NO 17
<211> LENGTH: 60
<212> TYPE: DNA
<213> ORGANISM: Mycoplasma bovis

<400> SEQUENCE: 17

cacataaaat atttaaggac atattatgag taagaaaaat aaattaatga ttgggctttc     60
```

<210> SEQ ID NO 18
<211> LENGTH: 60
<212> TYPE: DNA
<213> ORGANISM: Mycoplasma bovis

<400> SEQUENCE: 18
cacataaaat atttaaggac atattattag taagaaaaat aaattaatga ttgggctttc 60

<210> SEQ ID NO 19
<211> LENGTH: 54
<212> TYPE: PRT
<213> ORGANISM: Mycoplasma bovis

<400> SEQUENCE: 19

Met Ser Lys Lys Asn Lys Leu Met Ile Gly Leu Ser Ser Thr Ala Ile
1 5 10 15

Pro Leu Leu Ala Ala Val Ser Ala Lys Cys Gly Gly Thr Val Asn Tyr
20 25 30

Glu Asp Leu Gly Lys Asp Ala Lys Lys Ile Ser Leu Gly Val Ser Phe
35 40 45

Ser Ser Gly Gln Pro Gln
50

<210> SEQ ID NO 20
<211> LENGTH: 54
<212> TYPE: PRT
<213> ORGANISM: Mycoplasma bovis

<400> SEQUENCE: 20

Ile Ser Lys Lys Asn Lys Leu Met Ile Gly Leu Ser Ser Thr Ala Ile
1 5 10 15

Pro Leu Leu Ala Ala Val Ser Ala Lys Cys Gly Gly Thr Val Asn Tyr
20 25 30

Glu Asp Leu Gly Lys Asp Ala Lys Lys Ile Ser Leu Gly Val Ser Phe
35 40 45

Ser Ser Gly Gln Pro Gln
50

<210> SEQ ID NO 21
<211> LENGTH: 60
<212> TYPE: DNA
<213> ORGANISM: Mycoplasma bovis

<400> SEQUENCE: 21
tttaacacag taacatctag aatatctaga gacaaccgtg aaagaagagt gttcggctat 60

<210> SEQ ID NO 22
<211> LENGTH: 60
<212> TYPE: DNA
<213> ORGANISM: Mycoplasma bovis

<400> SEQUENCE: 22
tttaacacag taacatctag aatatctaga gacgaccgtg aaagaagagt gttcggctat 60

<210> SEQ ID NO 23
<211> LENGTH: 51
<212> TYPE: PRT
<213> ORGANISM: Mycoplasma bovis

<400> SEQUENCE: 23

Ala Ala Ile Ile Asn Glu Asp Gly Thr Ile Ser Ser His Gly Phe Ala

```
1               5                   10                  15

Pro Asp Asp Gln Phe Asn Thr Val Thr Ser Arg Ile Ser Arg Asp Asn
            20                  25                  30

Arg Glu Arg Arg Val Phe Gly Tyr Asp Ser Pro Tyr Gly Arg Ser Pro
        35                  40                  45

Asp Asn Val
    50
```

<210> SEQ ID NO 24
<211> LENGTH: 51
<212> TYPE: PRT
<213> ORGANISM: Mycoplasma bovis

<400> SEQUENCE: 24

```
Ala Ala Ile Ile Asn Glu Asp Gly Thr Ile Ser Ser His Gly Phe Ala
1               5                   10                  15

Pro Asp Asp Gln Phe Asn Thr Val Thr Ser Arg Ile Ser Arg Asp Asp
            20                  25                  30

Arg Glu Arg Arg Val Phe Gly Tyr Asp Ser Pro Tyr Gly Arg Ser Pro
        35                  40                  45

Asp Asn Val
    50
```

<210> SEQ ID NO 25
<211> LENGTH: 60
<212> TYPE: DNA
<213> ORGANISM: Mycoplasma bovis

<400> SEQUENCE: 25
ggaaaagcta aatttgctta ccaaggagat gacaaagtta tattgcctga gttcaaaaca     60

<210> SEQ ID NO 26
<211> LENGTH: 60
<212> TYPE: DNA
<213> ORGANISM: Mycoplasma bovis

<400> SEQUENCE: 26
ggaaaagcta aatttgctta ccaaggagat gacaaagtta tattacctga gttcaaaaca     60

<210> SEQ ID NO 27
<211> LENGTH: 60
<212> TYPE: PRT
<213> ORGANISM: Mycoplasma bovis

<400> SEQUENCE: 27

```
Ala Lys Ser Ile Thr Leu Ile Met Thr Ile Leu Ala Asp Ala Ile Ala
1               5                   10                  15

Thr Ala Arg Gly Gly Lys Ala Lys Phe Ala Tyr Gln Gly Asp Asp Lys
            20                  25                  30

Val Ile Leu Pro Glu Phe Lys Thr Asp Arg Val Gln Asn Pro Arg Phe
        35                  40                  45

Val Asn Gln Arg Arg Ser Phe Glu Gln Thr Gly Ala
    50                  55                  60
```

<210> SEQ ID NO 28
<211> LENGTH: 60
<212> TYPE: DNA
<213> ORGANISM: Mycoplasma bovis

<400> SEQUENCE: 28
atgattgccg atcagaatag tggcaagaga atttcgttcc ctgttgaagg atctattata 60

<210> SEQ ID NO 29
<211> LENGTH: 60
<212> TYPE: DNA
<213> ORGANISM: Mycoplasma bovis

<400> SEQUENCE: 29
atgattgccg atcagaatag tggcaagaga atttcgttcc ctgtttaagg atctattata 60

<210> SEQ ID NO 30
<211> LENGTH: 60
<212> TYPE: PRT
<213> ORGANISM: Mycoplasma bovis

<400> SEQUENCE: 30

Met Ile Ala Asp Gln Asn Ser Gly Lys Arg Ile Ser Phe Pro Val Glu
1 5 10 15

Gly Ser Ile Ile Asp Val Gln Ala Tyr Lys Tyr Asp Gly Thr Leu Tyr
20 25 30

Arg Gln Trp Asn Gly Val Lys Val Leu Arg Asn Thr Asn Lys His Tyr
35 40 45

Val Leu Leu Met Tyr Lys Thr Arg Val Ser Glu Gln
50 55 60

<210> SEQ ID NO 31
<211> LENGTH: 15
<212> TYPE: PRT
<213> ORGANISM: Mycoplasma bovis

<400> SEQUENCE: 31

Met Ile Ala Asp Gln Asn Ser Gly Lys Arg Ile Ser Phe Pro Val
1 5 10 15

<210> SEQ ID NO 32
<211> LENGTH: 44
<212> TYPE: PRT
<213> ORGANISM: Mycoplasma bovis

<400> SEQUENCE: 32

Gly Ser Ile Ile Asp Val Gln Ala Tyr Lys Tyr Asp Gly Thr Leu Tyr
1 5 10 15

Arg Gln Trp Asn Gly Val Lys Val Leu Arg Asn Thr Asn Lys His Tyr
20 25 30

Val Leu Leu Met Tyr Lys Thr Arg Val Ser Glu Gln
35 40

<210> SEQ ID NO 33
<211> LENGTH: 55
<212> TYPE: DNA
<213> ORGANISM: Mycoplasma bovis

<400> SEQUENCE: 33
aatgaattta gtaagtcatt atatgaaagc gcaaaaagct ctgccaagtt gcata 55

<210> SEQ ID NO 34
<211> LENGTH: 55
<212> TYPE: DNA
<213> ORGANISM: Mycoplasma bovis

<400> SEQUENCE: 34
aataaattta gtaagtcatt atatgaaagc gcaaaaagct ctgccaagtt gcata 55

<210> SEQ ID NO 35
<211> LENGTH: 60
<212> TYPE: PRT
<213> ORGANISM: Mycoplasma bovis

<400> SEQUENCE: 35

```
Ser Gly Tyr Trp Ala Gly Leu Asp Gly Phe Asp Val Ser Ser Leu Asp
1               5                   10                  15

Asn Gly Thr Val Glu Lys Met Phe Asp Glu Ile Phe Gly Ser Pro Asp
            20                  25                  30

Lys Lys Gly Val Leu Glu Thr Gln His Gly Leu Thr Lys Asn Glu Ile
        35                  40                  45

Ala Lys Phe Leu Asp Ser Ser Ala Asn Glu Phe Ser
    50                  55                  60
```

<210> SEQ ID NO 36
<211> LENGTH: 60
<212> TYPE: PRT
<213> ORGANISM: Mycoplasma bovis

<400> SEQUENCE: 36

```
Ser Gly Tyr Trp Ala Gly Leu Asp Gly Phe Asp Val Ser Ser Leu Asp
1               5                   10                  15

Asn Gly Thr Val Glu Lys Met Phe Asp Glu Ile Phe Gly Ser Pro Asp
            20                  25                  30

Lys Lys Gly Val Leu Glu Thr Gln His Gly Leu Thr Lys Asn Glu Ile
        35                  40                  45

Ala Lys Phe Leu Asp Ser Ser Ala Asn Lys Phe Ser
    50                  55                  60
```

<210> SEQ ID NO 37
<211> LENGTH: 345
<212> TYPE: PRT
<213> ORGANISM: Mycoplasma bovis

<400> SEQUENCE: 37

```
Met Ile Leu Val Glu Pro Ile Arg Asn Gly Lys Tyr Val Lys Asp Gly
1               5                   10                  15

Ala Tyr Trp Leu Ala Ile Gln Ile Trp Ala Met Asn His Leu Arg Leu
            20                  25                  30

Asn Glu Lys Ile Val Phe Pro Gly Ile Ala Ala Pro His Ile Gln Leu
        35                  40                  45

Gly Tyr Phe Gln Asn Pro Glu Val Glu Val Asn Phe Lys Tyr Leu Lys
    50                  55                  60

Glu His Asn Leu Glu Val Val Arg Arg Asn Thr Gly Gly Gly Ala Ile
65                  70                  75                  80

Tyr Ile Asp Asp Asn Ser Val Asn Val Cys Tyr Leu Ile Pro Tyr Asp
                85                  90                  95

Glu Lys Asp Asn Ile Leu Gly Asn Tyr Asp Lys Phe Tyr Glu Pro Thr
            100                 105                 110

Ile Lys Met Leu Lys Glu Leu Gly Ala Lys Asn Val Val Gln Ser Gly
        115                 120                 125

Lys Asn Asp Leu Thr Ile Asp Gly Lys Lys Val Ser Gly Ala Ala Met
    130                 135                 140

Met Leu Asn Gly Asp Val Ile Tyr Gly Gly Asn Ser Leu Leu Tyr Lys
145                 150                 155                 160
```

```
Val Asp Tyr Asp Ala Met Val Asp Ser Leu Asn Pro Asn Arg Lys Lys
                165                 170                 175

Ile Glu Ala Lys Gly Val Lys Ser Ile Arg Gln Arg Val Ala Pro Leu
            180                 185                 190

Ser Asn Tyr Phe Asp Glu Gln Tyr Arg Asn Leu Asp Ile Phe Glu Phe
        195                 200                 205

Lys Asp Leu Val Ile Lys Lys Leu Phe Gly Val Asp Asp Leu Ser Lys
    210                 215                 220

Val Lys Arg Tyr Glu Leu Thr Glu Gln Asp Trp Ala Gln Val Asp Glu
225                 230                 235                 240

Leu Val Asn Thr Lys Tyr Lys Asn Trp Asp Trp Asn Tyr Gly Leu Ser
                245                 250                 255

Pro Arg Tyr Glu Tyr Asn Arg Asp Ala Arg Leu Ala Ile Gly Thr Ile
            260                 265                 270

Asn Phe Ser Leu Ala Val Glu Gly Gln Arg Ile Glu Lys Ile Lys Ile
        275                 280                 285

Ser Gly Asp Phe Phe Ala Lys Lys Asp Ile Thr Glu Leu Glu Lys Ala
    290                 295                 300

Leu Val Gly Thr Lys Met Thr Phe Asp Asp Leu Val Lys Ala Phe Lys
305                 310                 315                 320

Asp Ala Asp Ile Gln Ser Tyr Phe Phe Asn Glu Ile Ser Pro Glu Glu
                325                 330                 335

Val Ser Lys Ile Ile Leu Asp Glu Glu
            340                 345
```

<210> SEQ ID NO 38
<211> LENGTH: 345
<212> TYPE: PRT
<213> ORGANISM: Mycoplasma bovis

<400> SEQUENCE: 38

```
Met Ile Leu Val Glu Pro Ile Arg Asn Gly Lys Tyr Val Lys Asp Gly
1               5                   10                  15

Ala Tyr Trp Leu Ala Ile Gln Ile Trp Ala Met Asn His Leu Arg Leu
            20                  25                  30

Asn Glu Lys Ile Val Phe Pro Gly Ile Ala Ala Pro His Ile Gln Leu
        35                  40                  45

Gly Tyr Phe Gln Asn Pro Glu Val Glu Val Asn Phe Lys Tyr Leu Lys
    50                  55                  60

Glu His Asn Leu Glu Val Val Arg Arg Asn Thr Gly Gly Gly Ala Ile
65                  70                  75                  80

Tyr Ile Asp Asp Asn Ser Val Asn Val Cys Tyr Leu Ile Pro Tyr Asp
                85                  90                  95

Glu Lys Asp Asn Ile Leu Gly Asn Tyr Asp Lys Phe Tyr Glu Pro Thr
            100                 105                 110

Ile Lys Met Leu Lys Glu Leu Gly Ala Lys Asn Val Val Gln Ser Gly
        115                 120                 125

Lys Asn Asp Leu Thr Ile Asp Gly Lys Lys Val Ser Gly Ala Ala Met
    130                 135                 140

Met Leu Asn Gly Asp Val Ile Tyr Gly Gly Asn Ser Leu Leu Tyr Lys
145                 150                 155                 160

Val Asp Tyr Asp Ala Met Val Asp Ser Leu Asn Pro Asn Arg Lys Lys
                165                 170                 175

Ile Glu Ala Lys Gly Val Lys Ser Ile Arg Gln Arg Val Ala Pro Leu
            180                 185                 190
```

```
Ser Asn Tyr Phe Asp Glu Gln Tyr Arg Asn Leu Asp Ile Phe Glu Phe
        195                 200                 205

Lys Asp Leu Val Ile Lys Lys Leu Phe Gly Val Asp Asp Leu Ser Lys
    210                 215                 220

Val Lys Arg Tyr Glu Leu Thr Glu Gln Asp Trp Ala Gln Val Asp Glu
225                 230                 235                 240

Leu Val Asn Thr Lys Tyr Lys Asn Trp Asp Trp Asn Tyr Gly Leu Ser
                245                 250                 255

Pro Arg Tyr Glu Tyr Asn Arg Asp Ala Arg Leu Ala Ile Gly Thr Ile
            260                 265                 270

Asn Phe Ser Leu Ala Val Glu Gly Gln Ile Ile Glu Lys Ile Lys Ile
        275                 280                 285

Ser Gly Asp Phe Phe Ala Lys Lys Asp Ile Thr Glu Leu Glu Lys Ala
    290                 295                 300

Leu Val Gly Thr Lys Met Thr Phe Asp Asp Leu Val Lys Ala Phe Lys
305                 310                 315                 320

Asp Ala Asp Ile Gln Ser Tyr Phe Phe Asn Glu Ile Ser Pro Glu Glu
                325                 330                 335

Val Ser Lys Ile Ile Leu Asp Glu Glu
            340                 345
```

<210> SEQ ID NO 39
<211> LENGTH: 290
<212> TYPE: PRT
<213> ORGANISM: Mycoplasma bovis

<400> SEQUENCE: 39

```
Met Lys Val Cys Ile Ile Ser Ile Leu Gly Arg Pro Asn Val Gly Lys
1               5                   10                  15

Ser Ser Leu Leu Asn Lys Ile Ile Lys Tyr Asp Leu Ala Ile Val Ser
            20                  25                  30

Asn Val Pro Gln Thr Thr Arg Asp Gln Ile Met Gly Val Tyr Thr Glu
        35                  40                  45

Asn Asp Tyr Gln Phe Val Phe Val Asp Thr Pro Gly Ile His Lys Pro
    50                  55                  60

Leu Asn Leu Leu Gly Glu Ser Leu Asn Lys Glu Ala Phe Ser Ser Ile
65                  70                  75                  80

Asn Asp Ile Asp Cys Ile Leu Phe Leu Thr Pro Val Asn Glu Glu Ile
                85                  90                  95

Lys Ser Gly Asp Lys Leu Ile Leu Glu Arg Ile Ala Asn Ser Lys Asn
            100                 105                 110

Lys Ile Ala Val Ile Ser Lys Ile Asp Leu Ala Lys Ser Pro Asp Asp
        115                 120                 125

Ile Ser Lys Lys Ile Lys Ser Leu Glu Glu Phe Asn Phe Gln Lys Ile
    130                 135                 140

Ile Ser Val Ser Asn Lys Asn Asp Lys Ser Ile Asp Ser Leu Ile Glu
145                 150                 155                 160

Ile Leu Lys Glu Tyr Ser Tyr Glu Ala Pro Pro Phe Tyr Asp Glu Asp
                165                 170                 175

Tyr Ile Thr Asp Lys Ser Met Arg Phe Met Ala Lys Glu Tyr Ile Arg
            180                 185                 190

Glu Ser Ala Ile Asn Leu Leu Thr Asp Glu Leu Pro His Ser Ile Ala
        195                 200                 205

Val Glu Val Gln Asp Phe Ile Glu Glu Glu Asp Arg Ile Thr Ile Asn
```

-continued

```
    210                 215                 220

Ala Val Ile Tyr Val Lys Lys Asp Ser Gln Lys Gly Ile Leu Ile Gly
225                 230                 235                 240

Lys Gly Ala Ser Met Ile Lys Lys Ile Gly Thr Asn Ala Arg Met Lys
                245                 250                 255

Met Gly His Gln Phe Asn Ser Lys Val Thr Leu Asn Leu Lys Val Lys
            260                 265                 270

Val Ser Asn Lys Trp Ile Asn Asp Lys Ser Ala Leu Lys Lys Phe Gly
        275                 280                 285

Tyr Asn
    290
```

<210> SEQ ID NO 40
<211> LENGTH: 873
<212> TYPE: DNA
<213> ORGANISM: Mycoplasma bovis

<400> SEQUENCE: 40

```
atgaaggtat gtattattag tattttaggg cgtccaaatg ttggcaaatc ctcattatta     60

aacaaaatta ttaaatatga tcttgctatt gtatctaacg ttccgcaaac aactagagat    120

caaataatgg gagtgtacac tgaaaatgat tatcagtttg tttttgttga cacgcccgga    180

attcataaac cattgaattt gctaggggag tcattaaaca aagaagcatt tagctcaata    240

aacgacattg attgcatttt atttttaacc cccgtaaatg aagagattaa gtcaggggat    300

aaattaattc tagaaagaat tgctaattca aaaaataaaa ttgctgtaat atcaaaaatt    360

gatttagcta aatcaccaga cgatatttct aagaaaatta agagcttaga agaattcaat    420

tttcaaaaaa ttatttctgt ttctaataaa aatgacaaat caattgactc actaattgaa    480

atattaaagg agtattcata cgaagctcct ccattttacg acgaagacta tattacagat    540

aaatcgatga gatttatggc taaagaatac attcgtgaaa gcgctataaa tcttttaacg    600

gacgaattac cgcattcaat tgctgtcgaa gtgcaggatt ttattgaaga agaagacaga    660

ataacaatta atgccgtaat ttatgttaaa aaagattcgc aaaaaggaat tttaattggc    720

aaaggggcat caatgattaa aaaaattggc accaatgcta gaatgaaaat gggccatcag    780

ttcaatagta aagttacgct taatttaaag gtaaaagttt ctaataaatg gatcaatgac    840

aaaagtgcac taaaaaaatt tggctataat taa                                 873
```

<210> SEQ ID NO 41
<211> LENGTH: 873
<212> TYPE: DNA
<213> ORGANISM: Mycoplasma bovis

<400> SEQUENCE: 41

```
atgaaggtat gtattattag tattttaggg cgtccaaatg ttggcaaatc ctcattatta     60

aacaaaatta ttaaatatga tcttgctatt gtatctaacg ttccgcaaac aactagagat    120

caaataatgg gagtgtacac tgaaaatgat tatcagtttg tttttgttga cacgcccgga    180

attcataaac cattaaattt gctaggggag tcattaaaca aagaagcatt tagctcaata    240

aacgacattg attgcatttt atttttaacc cccgtaaatg aagagattaa gtcaggggat    300

aaattaattc tagaaagaat tgctaattca aaaaataaaa ttgctgtaat atcaaaaatt    360

gatttagcta aatcaccaga cgatatttct aagaaaatta agagcttaga agaattcaat    420

tttcaaaaaa ttatttctgt ttctaataaa aatgacaaat caattgactc actaattgaa    480
```

```
atattaaagg agtattcata cgaagctcct ccattttacg acgaagacta tattacagat    540

aaatcgatga gatttatggc taaagaatac attcgtgaaa gcgctataaa tcttttaacg    600

gacgaattac cgcattcaat tgctgtcgaa gtgcaggatt ttattgaaga agaagacaga    660

ataacaatta atgccgtaat ttatgttaaa aaagattcgc aaaaaggaat tttaattggc    720

aaaggggcat caatgattaa aaaaattggc accaatgcta gaatgaaaat gggccatcag    780

ttcaatagta aagttacgct taatttaaag gtaaaagttt ctaataaatg gatcaatgac    840

aaaagtgcac taaaaaaatt tggctataat taa                                 873
```

<210> SEQ ID NO 42
<211> LENGTH: 728
<212> TYPE: PRT
<213> ORGANISM: Mycoplasma bovis

<400> SEQUENCE: 42

```
Met Ser Lys Lys Asn Lys Leu Met Ile Gly Leu Ser Ser Thr Ala Ile
1               5                   10                  15

Pro Leu Leu Ala Ala Val Ser Ala Lys Cys Gly Gly Thr Val Asn Tyr
            20                  25                  30

Glu Asp Leu Gly Lys Asp Ala Lys Lys Ile Ser Leu Gly Val Ser Phe
        35                  40                  45

Ser Ser Gly Gln Pro Gln Trp Asn Thr Met Ala Ser Leu Ile Lys Tyr
    50                  55                  60

Tyr Asn Glu Ala His Lys Asn Asp Lys His Phe Leu Pro Val Glu Leu
65                  70                  75                  80

Lys His Leu Gly Ser Gly Tyr Pro Glu Gly Glu Asn Thr Val Ile Thr
                85                  90                  95

Glu Leu Lys Ala Lys Arg Asn Glu Val Val Asn Leu Ala Phe Asn Tyr
            100                 105                 110

Gly Ser Leu Ala Ser Arg Leu Ala Ser Ser Glu Met Arg Asp Leu Tyr
        115                 120                 125

Lys Met Asp Lys Val Leu Asn Phe Glu Asp Asn Asp Lys Asp Ile Ser
    130                 135                 140

Val Asp Leu Lys Asn Ile Asn Glu Lys Phe Ala Arg Ala Asn Ser Asn
145                 150                 155                 160

Thr Glu Asn Leu Pro Asn Asn Gly Thr Phe Met Ile Pro Met Leu Lys
                165                 170                 175

Ser Ile Gln Val Met Ser Ala Asn Ala Pro Val Leu Gln Tyr Ile Phe
            180                 185                 190

Lys Thr Phe Glu Asn Lys Gly Ala Lys Phe Asp Asp Ser Phe Lys Lys
        195                 200                 205

Ser Ala Arg Tyr Gln Asp Ile Met Thr Asn Gly Lys Gly Asp Glu Ser
    210                 215                 220

Glu Val Gln Lys Leu Trp Gly Glu Phe Glu Ser Ser Gln Gln Asp Ala
225                 230                 235                 240

Val Lys Lys Leu Thr Ile Ser Ser Ser Thr Phe Glu Asn Leu Glu Glu
                245                 250                 255

Leu Leu Asn Phe Ala Asn Ile Ala Gln Lys Ser Phe Lys Asn Ser Ala
            260                 265                 270

Ala Lys Asn Ser Arg Leu His Ile Leu Gly Val Asp Asp Val Ser Gly
        275                 280                 285

Leu Ile Gln Ser Leu Pro Tyr Ala Met Ile Asn Ala Asp Ala Asn Asp
    290                 295                 300
```

-continued

```
Phe Phe Ile Gln Thr Gly Leu Val Lys Asn Lys Thr Thr Val Asn Tyr
305                 310                 315                 320

Lys Lys Ile Lys Asp Lys Asn Asn Lys Ser Val Lys Ala Leu Ser Glu
                325                 330                 335

Ile Tyr Asn Lys Phe Lys Glu Ser Leu Ala Thr Lys Ser Leu Thr Leu
            340                 345                 350

Leu Ala Gly Gly Glu Tyr Thr Ser Ser Tyr Gln Thr Lys His Glu Tyr
        355                 360                 365

Ala Phe Gly Ile Gly Ser Thr Ala Gly Tyr Arg His Asn Phe Ile Ser
    370                 375                 380

Asp Lys Thr Lys Lys Val Ile Phe Thr Leu Lys Gly Thr Asp Val Ser
385                 390                 395                 400

Gly Glu Lys Asp Lys Glu Phe Lys Asn Val Ile Lys Lys Thr Glu Lys
                405                 410                 415

Gly Val Asp Gln Leu Phe Val Thr Phe Lys Glu Asn Ala Asn Lys Val
            420                 425                 430

Tyr Lys Ser Thr Val Asp Thr Asp Lys Leu Asp Asp Glu Glu Lys Asp
        435                 440                 445

Ser Leu Arg Tyr Ser Tyr Lys Ser Leu Asp Ser Ala Thr Asp Ser Lys
    450                 455                 460

Met Asp Glu Ile Leu Lys Lys Ile Thr Asn Thr Asp Pro Glu Ala Ser
465                 470                 475                 480

Asp Asn Lys Gln Trp Leu Leu Phe Leu Arg Glu Asp Asn Gln Ser Asp
                485                 490                 495

Ile Lys Thr Val Lys Glu Lys Gly Ala Gln Glu Val Gly Thr Val Ile
            500                 505                 510

Glu Thr Lys Ile Ser Gly Ala Ser Lys Tyr Lys Ile Phe Phe Leu Asn
        515                 520                 525

Asp Glu Ser Leu Leu Val Arg Lys Glu Leu Ser Ser Lys Gly Thr Leu
    530                 535                 540

Gln Glu Lys Glu Leu Ile Val Phe Ala Val Pro Gly Lys Trp Asn Lys
545                 550                 555                 560

Ser Asn Glu Lys Arg Val Ile Tyr Ser Gln Gly Pro Ser Leu Ile Gly
                565                 570                 575

Val Ser Arg Gly Ala Lys Pro Asp Arg Ala Ala Lys Asn Phe Ala Lys
            580                 585                 590

Phe Leu Thr Ser Leu Glu Lys Ile Asp Ile Thr Leu Ser Lys Tyr Asp
        595                 600                 605

Lys Asp Met Lys Lys Thr Lys Asp Ser Arg Asp Lys Pro Tyr Lys Gln
    610                 615                 620

Val Thr Pro Ala Gln Phe Ile Ser Asp Ala Ala Ser Tyr Val Phe Pro
625                 630                 635                 640

Val Lys Gly Phe Glu Lys Thr Asp Thr Ser Lys Ile Lys Asn Lys Tyr
                645                 650                 655

Ile Val His Thr Tyr Asn Glu Leu Lys Glu Ala Val Thr Asn Lys Asn
            660                 665                 670

Val Val Ile Tyr Glu Glu Pro Ala Gly Phe His Ser Ser Ser Phe Arg
        675                 680                 685

Glu Ser Leu Gly Ser Ala Phe Lys Ser Ala Tyr Leu Lys Ala Lys Asn
    690                 695                 700

Asp Gln Pro Leu Glu Asp Phe Asp Lys Glu Ile Ile Gly Ser Ile Ile
705                 710                 715                 720

Ala Ser Ser Ser Gln Ile Leu Lys
```

725

<210> SEQ ID NO 43
<211> LENGTH: 728
<212> TYPE: PRT
<213> ORGANISM: Mycoplasma bovis

<400> SEQUENCE: 43

```
Ile Ser Lys Lys Asn Lys Leu Met Ile Gly Leu Ser Ser Thr Ala Ile
1               5                   10                  15

Pro Leu Leu Ala Ala Val Ser Ala Lys Cys Gly Gly Thr Val Asn Tyr
            20                  25                  30

Glu Asp Leu Gly Lys Asp Ala Lys Lys Ile Ser Leu Gly Val Ser Phe
        35                  40                  45

Ser Ser Gly Gln Pro Gln Trp Asn Thr Met Ala Ser Leu Ile Lys Tyr
    50                  55                  60

Tyr Asn Glu Ala His Lys Asn Asp Lys His Phe Leu Pro Val Glu Leu
65                  70                  75                  80

Lys His Leu Gly Ser Gly Tyr Pro Glu Gly Glu Asn Thr Val Ile Thr
                85                  90                  95

Glu Leu Lys Ala Lys Arg Asn Glu Val Val Asn Leu Ala Phe Asn Tyr
            100                 105                 110

Gly Ser Leu Ala Ser Arg Leu Ala Ser Ser Glu Met Arg Asp Leu Tyr
        115                 120                 125

Lys Met Asp Lys Val Leu Asn Phe Glu Asp Asn Asp Lys Asp Ile Ser
    130                 135                 140

Val Asp Leu Lys Asn Ile Asn Glu Lys Phe Ala Arg Ala Asn Ser Asn
145                 150                 155                 160

Thr Glu Asn Leu Pro Asn Asn Gly Thr Phe Met Ile Pro Met Leu Lys
                165                 170                 175

Ser Ile Gln Val Met Ser Ala Asn Ala Pro Val Leu Gln Tyr Ile Phe
            180                 185                 190

Lys Thr Phe Glu Asn Lys Gly Ala Lys Phe Asp Asp Ser Phe Lys Lys
        195                 200                 205

Ser Ala Arg Tyr Gln Asp Ile Met Thr Asn Gly Lys Gly Asp Glu Ser
    210                 215                 220

Glu Val Gln Lys Leu Trp Gly Glu Phe Glu Ser Ser Gln Gln Asp Ala
225                 230                 235                 240

Val Lys Lys Leu Thr Ile Ser Ser Ser Thr Phe Glu Asn Leu Glu Glu
                245                 250                 255

Leu Leu Asn Phe Ala Asn Ile Ala Gln Lys Ser Phe Lys Asn Ser Ala
            260                 265                 270

Ala Lys Asn Ser Arg Leu His Ile Leu Gly Val Asp Asp Val Ser Gly
        275                 280                 285

Leu Ile Gln Ser Leu Pro Tyr Ala Met Ile Asn Ala Asp Ala Asn Asp
    290                 295                 300

Phe Phe Ile Gln Thr Gly Leu Val Lys Asn Lys Thr Thr Val Asn Tyr
305                 310                 315                 320

Lys Lys Ile Lys Asp Lys Asn Asn Lys Ser Val Lys Ala Leu Ser Glu
                325                 330                 335

Ile Tyr Asn Lys Phe Lys Glu Ser Leu Ala Thr Lys Ser Leu Thr Leu
            340                 345                 350

Leu Ala Gly Gly Glu Tyr Thr Ser Ser Tyr Gln Thr Lys His Glu Tyr
        355                 360                 365
```

```
Ala Phe Gly Ile Gly Ser Thr Ala Gly Tyr Arg His Asn Phe Ile Ser
    370                 375                 380

Asp Lys Thr Lys Lys Val Ile Phe Thr Leu Lys Gly Thr Asp Val Ser
385                 390                 395                 400

Gly Glu Lys Asp Lys Glu Phe Lys Asn Val Ile Lys Lys Thr Glu Lys
                405                 410                 415

Gly Val Asp Gln Leu Phe Val Thr Phe Lys Glu Asn Ala Asn Lys Val
            420                 425                 430

Tyr Lys Ser Thr Val Asp Thr Asp Lys Leu Asp Asp Glu Glu Lys Asp
        435                 440                 445

Ser Leu Arg Tyr Ser Tyr Lys Ser Leu Asp Ser Ala Thr Asp Ser Lys
    450                 455                 460

Met Asp Glu Ile Leu Lys Lys Ile Thr Asn Thr Asp Pro Glu Ala Ser
465                 470                 475                 480

Asp Asn Lys Gln Trp Leu Leu Phe Leu Arg Glu Asp Asn Gln Ser Asp
                485                 490                 495

Ile Lys Thr Val Lys Glu Lys Gly Ala Gln Glu Val Gly Thr Val Ile
            500                 505                 510

Glu Thr Lys Ile Ser Gly Ala Ser Lys Tyr Lys Ile Phe Phe Leu Asn
        515                 520                 525

Asp Glu Ser Leu Leu Val Arg Lys Glu Leu Ser Ser Lys Gly Thr Leu
    530                 535                 540

Gln Glu Lys Glu Leu Ile Val Phe Ala Val Pro Gly Lys Trp Asn Lys
545                 550                 555                 560

Ser Asn Glu Lys Arg Val Ile Tyr Ser Gln Gly Pro Ser Leu Ile Gly
                565                 570                 575

Val Ser Arg Gly Ala Lys Pro Asp Arg Ala Ala Lys Asn Phe Ala Lys
            580                 585                 590

Phe Leu Thr Ser Leu Glu Lys Ile Asp Ile Thr Leu Ser Lys Tyr Asp
        595                 600                 605

Lys Asp Met Lys Lys Thr Lys Asp Ser Arg Asp Lys Pro Tyr Lys Gln
    610                 615                 620

Val Thr Pro Ala Gln Phe Ile Ser Asp Ala Ala Ser Tyr Val Phe Pro
625                 630                 635                 640

Val Lys Gly Phe Glu Lys Thr Asp Thr Ser Lys Ile Lys Asn Lys Tyr
                645                 650                 655

Ile Val His Thr Tyr Asn Glu Leu Lys Glu Ala Val Thr Asn Lys Asn
            660                 665                 670

Val Val Ile Tyr Glu Glu Pro Ala Gly Phe His Ser Ser Ser Phe Arg
        675                 680                 685

Glu Ser Leu Gly Ser Ala Phe Lys Ser Ala Tyr Leu Lys Ala Lys Asn
    690                 695                 700

Asp Gln Pro Leu Glu Asp Phe Asp Lys Glu Ile Ile Gly Ser Ile Ile
705                 710                 715                 720

Ala Ser Ser Ser Gln Ile Leu Lys
                725


<210> SEQ ID NO 44
<211> LENGTH: 735
<212> TYPE: PRT
<213> ORGANISM: Mycoplasma bovis

<400> SEQUENCE: 44

Met Ser Ile Phe Lys Lys Lys Lys Asn Arg Val Ile Phe Ala Thr Leu
1               5                   10                  15
```

```
Ala Phe Gly Ala Ile Ile Ser Ser Thr Ser Gly Val Leu Ile Tyr Arg
            20                  25                  30

Ser Ser Ser Asp Ile Asp Leu Ser Arg Val Ile Phe Ser Ser Ser Thr
        35                  40                  45

Asn Ser Glu Leu Ala Asn Asn Lys Asn Asn Ile Asn Lys Ala Ile Asp
    50                  55                  60

Ala Ile Lys Asp Asn Asn Val Val Glu Asn Glu Lys Pro Val Val Ile
65                  70                  75                  80

Lys Pro Ala Glu Val Pro Lys Ile Lys Ile Pro Asp Val Ala Lys Glu
                85                  90                  95

Thr Asn Pro Ser Pro Glu Val Asn Arg Asn Ser Ile Arg Pro Glu Lys
            100                 105                 110

Thr Glu Pro Leu Ile Ala Lys Pro Asn Val Val Thr Lys Glu Ile Phe
        115                 120                 125

Ile His Gly Val Lys Val Asn Ala Thr Ile Glu Val Thr Pro Asp Arg
    130                 135                 140

Val Ile Ser Asp Tyr Asp Lys Asp Arg Lys Ile Ser Asn Val Asn Pro
145                 150                 155                 160

Tyr Gln Asn Ile Ile Val Ser Lys Val Leu Asn Val Glu Val Thr Gln
                165                 170                 175

Glu Leu Arg Asp Lys Ser Val Lys Asn Ala Leu Asn Gly Asn Asp Gly
            180                 185                 190

Thr Gly Leu Phe Ala Gly Thr Phe Phe Val Phe Leu Asn Asn Ile Ile
        195                 200                 205

Thr Ser Ser Lys Asp Leu Lys Thr Ala Glu Asp Ala Val Met Asn Asn
    210                 215                 220

Pro Trp Ile Tyr Arg Asp Asn Ile His Arg Tyr Glu Arg Leu Leu Asn
225                 230                 235                 240

Asn Pro Asn Val Val Asn Phe Leu Lys Glu Asp Ala Lys Lys Glu Tyr
                245                 250                 255

Pro Asn Lys Asn Phe Asp Ser Ile Val Gln Arg Gln Ile Trp Leu Ile
            260                 265                 270

His Asn Leu Asp Gln Thr Lys Phe Thr Lys Leu Ala Lys Asp Ala Glu
        275                 280                 285

Ser Phe Leu Ser Gln Gly Leu Val Ile Ser Pro Arg Ala Ala Ile Ile
    290                 295                 300

Asn Glu Asp Gly Thr Ile Ser Ser His Gly Phe Ala Pro Asp Asp Gln
305                 310                 315                 320

Phe Asn Thr Val Thr Ser Arg Ile Ser Arg Asp Asn Arg Glu Arg Arg
                325                 330                 335

Val Phe Gly Tyr Asp Ser Pro Tyr Gly Arg Ser Pro Asp Asn Val Trp
            340                 345                 350

Glu Gly Ser Tyr Pro Gly Trp Lys Lys Glu Asp Val Thr Ser Asp Thr
        355                 360                 365

Lys Phe Gln Lys Tyr Asn Val Ser Ser Ala Asp Gly Ile Lys Leu Thr
    370                 375                 380

Lys Leu Thr Arg Glu Lys Pro Glu Lys Gly Ser Gly Ala Leu Asn Glu
385                 390                 395                 400

Gly Leu Val Val Glu Ile Asp Ala Ser Asn Thr Ser Gly Tyr Asp Lys
                405                 410                 415

Thr Leu Lys Leu Ile Asn Glu Leu Lys Lys Asp Lys Val Gln Val Thr
            420                 425                 430
```

```
Ser Tyr Arg Ile Lys Asn Met Gly Asn Asn Asp Pro Ser Gln Lys Phe
        435                 440                 445

Arg Asp Ile Leu Asn Ala Leu Pro Asp Asn Ile Pro Gln Leu Glu Leu
    450                 455                 460

Phe Phe Ser Ala Glu Ala Thr Asn Thr Ser Ser Leu Ile Ala Leu Glu
465                 470                 475                 480

Asn Lys Arg Ile Lys Glu Leu Ser Leu Tyr Thr Leu Gly Asn Ser Leu
                485                 490                 495

Leu His Lys Trp Ser Phe Asn Pro Leu Ala Leu Arg Asn Thr Glu Trp
            500                 505                 510

Ile Asn Thr Val Asp Tyr Asn Val Ser Arg Asp Phe Arg Pro Asn Thr
        515                 520                 525

Ser Ile Pro Thr Arg Ile Thr Phe Asp Thr Ile Ala Phe Asp Ser Asp
    530                 535                 540

Asp Phe Lys Asn Lys Ser Phe Glu Arg Ile Asn Asp Gly Leu Arg Met
545                 550                 555                 560

Val Tyr Phe Ala Arg Asn Asn Glu Pro Phe Phe Gln Ala Gly Leu Gly
                565                 570                 575

Pro Gly Leu Asn Pro Asp His Asn Glu Gly Asn Asn Ser Tyr Pro Met
            580                 585                 590

Gly Leu Asp Phe Ser Arg Val Glu Gly Ile Lys Ser Leu Arg Asn Leu
        595                 600                 605

Val Phe Asn Asp Val Val Lys Ser Asn Asn Thr Pro Arg Lys Ile Arg
    610                 615                 620

Arg Leu Thr Leu Phe Asn Asn Ser Glu Ala Phe Glu Ile Ser Ser Asp
625                 630                 635                 640

Glu Leu Ser Asn Ala Ser Phe Glu His Phe Ala Thr Asp Ser Met Asp
                645                 650                 655

Pro Tyr Ser Lys Pro Lys Ile Met Phe Ser Asn Gly Asp Thr Thr Asn
            660                 665                 670

Val Ile Lys Ile Ser Asp Ser Asn Glu Leu Asp Gln Lys Ala Val Trp
        675                 680                 685

Asn Leu Ser Lys Phe Phe Glu Tyr Asn Glu Lys Leu Lys Ala Ser Lys
    690                 695                 700

Arg Ile Asn Val Pro Lys Asp Ala Leu Lys Leu Lys Glu Gln Leu Glu
705                 710                 715                 720

Arg Leu Gly Tyr Lys Val Val Asn Gln Asp Gly Asn Ile Ile Tyr
                725                 730                 735


<210> SEQ ID NO 45
<211> LENGTH: 735
<212> TYPE: PRT
<213> ORGANISM: Mycoplasma bovis

<400> SEQUENCE: 45

Met Ser Ile Phe Lys Lys Lys Lys Asn Arg Val Ile Phe Ala Thr Leu
1               5                   10                  15

Ala Phe Gly Ala Ile Ile Ser Ser Thr Ser Gly Val Leu Ile Tyr Arg
            20                  25                  30

Ser Ser Ser Asp Ile Asp Leu Ser Arg Val Ile Phe Ser Ser Ser Thr
        35                  40                  45

Asn Ser Glu Leu Ala Asn Asn Lys Asn Asn Ile Asn Lys Ala Ile Asp
    50                  55                  60

Ala Ile Lys Asp Asn Asn Val Val Glu Asn Glu Lys Pro Val Val Ile
65                  70                  75                  80
```

-continued

```
Lys Pro Ala Glu Val Pro Lys Ile Lys Ile Pro Asp Val Ala Lys Glu
                85                  90                  95

Thr Asn Pro Ser Pro Glu Val Asn Arg Asn Ser Ile Arg Pro Glu Lys
            100                 105                 110

Thr Glu Pro Leu Ile Ala Lys Pro Asn Val Val Thr Lys Glu Ile Phe
        115                 120                 125

Ile His Gly Val Lys Val Asn Ala Thr Ile Glu Val Thr Pro Asp Arg
    130                 135                 140

Val Ile Ser Asp Tyr Asp Lys Asp Arg Lys Ile Ser Asn Val Asn Pro
145                 150                 155                 160

Tyr Gln Asn Ile Ile Val Ser Lys Val Leu Asn Val Glu Val Thr Gln
                165                 170                 175

Glu Leu Arg Asp Lys Ser Val Lys Asn Ala Leu Asn Gly Asn Asp Gly
            180                 185                 190

Thr Gly Leu Phe Ala Gly Thr Phe Phe Val Phe Leu Asn Asn Ile Ile
        195                 200                 205

Thr Ser Ser Lys Asp Leu Lys Thr Ala Glu Asp Ala Val Met Asn Asn
    210                 215                 220

Pro Trp Ile Tyr Arg Asp Asn Ile His Arg Tyr Glu Arg Leu Leu Asn
225                 230                 235                 240

Asn Pro Asn Val Val Asn Phe Leu Lys Glu Asp Ala Lys Lys Glu Tyr
                245                 250                 255

Pro Asn Lys Asn Phe Asp Ser Ile Val Gln Arg Gln Ile Trp Leu Ile
            260                 265                 270

His Asn Leu Asp Gln Thr Lys Phe Thr Lys Leu Ala Lys Asp Ala Glu
        275                 280                 285

Ser Phe Leu Ser Gln Gly Leu Val Ile Ser Pro Arg Ala Ala Ile Ile
    290                 295                 300

Asn Glu Asp Gly Thr Ile Ser Ser His Gly Phe Ala Pro Asp Asp Gln
305                 310                 315                 320

Phe Asn Thr Val Thr Ser Arg Ile Ser Arg Asp Asp Arg Glu Arg Arg
                325                 330                 335

Val Phe Gly Tyr Asp Ser Pro Tyr Gly Arg Ser Pro Asp Asn Val Trp
            340                 345                 350

Glu Gly Ser Tyr Pro Gly Trp Lys Lys Glu Asp Val Thr Ser Asp Thr
        355                 360                 365

Lys Phe Gln Lys Tyr Asn Val Ser Ser Ala Asp Gly Ile Lys Leu Thr
    370                 375                 380

Lys Leu Thr Arg Glu Lys Pro Glu Lys Gly Ser Gly Ala Leu Asn Glu
385                 390                 395                 400

Gly Leu Val Val Glu Ile Asp Ala Ser Asn Thr Ser Gly Tyr Asp Lys
                405                 410                 415

Thr Leu Lys Leu Ile Asn Glu Leu Lys Lys Asp Lys Val Gln Val Thr
            420                 425                 430

Ser Tyr Arg Ile Lys Asn Met Gly Asn Asn Asp Pro Ser Gln Lys Phe
        435                 440                 445

Arg Asp Ile Leu Asn Ala Leu Pro Asp Asn Ile Pro Gln Leu Glu Leu
    450                 455                 460

Phe Phe Ser Ala Glu Ala Thr Asn Thr Ser Ser Leu Ile Ala Leu Glu
465                 470                 475                 480

Asn Lys Arg Ile Lys Glu Leu Ser Leu Tyr Thr Leu Gly Asn Ser Leu
                485                 490                 495
```

```
Leu His Lys Trp Ser Phe Asn Pro Leu Ala Leu Arg Asn Thr Glu Trp
            500                 505                 510

Ile Asn Thr Val Asp Tyr Asn Val Ser Arg Asp Phe Arg Pro Asn Thr
        515                 520                 525

Ser Ile Pro Thr Arg Ile Thr Phe Asp Thr Ile Ala Phe Asp Ser Asp
    530                 535                 540

Asp Phe Lys Asn Lys Ser Phe Glu Arg Ile Asn Asp Gly Leu Arg Met
545                 550                 555                 560

Val Tyr Phe Ala Arg Asn Asn Glu Pro Phe Phe Gln Ala Gly Leu Gly
                565                 570                 575

Pro Gly Leu Asn Pro Asp His Asn Glu Gly Asn Asn Ser Tyr Pro Met
            580                 585                 590

Gly Leu Asp Phe Ser Arg Val Glu Gly Ile Lys Ser Leu Arg Asn Leu
        595                 600                 605

Val Phe Asn Asp Val Val Lys Ser Asn Asn Thr Pro Arg Lys Ile Arg
    610                 615                 620

Arg Leu Thr Leu Phe Asn Asn Ser Glu Ala Phe Glu Ile Ser Ser Asp
625                 630                 635                 640

Glu Leu Ser Asn Ala Ser Phe Glu His Phe Ala Thr Asp Ser Met Asp
                645                 650                 655

Pro Tyr Ser Lys Pro Lys Ile Met Phe Ser Asn Gly Asp Thr Thr Asn
            660                 665                 670

Val Ile Lys Ile Ser Asp Ser Asn Glu Leu Asp Gln Lys Ala Val Trp
        675                 680                 685

Asn Leu Ser Lys Phe Phe Glu Tyr Asn Glu Lys Leu Lys Ala Ser Lys
    690                 695                 700

Arg Ile Asn Val Pro Lys Asp Ala Leu Lys Leu Lys Glu Gln Leu Glu
705                 710                 715                 720

Arg Leu Gly Tyr Lys Val Val Asn Gln Asp Gly Asn Ile Ile Tyr
                725                 730                 735


<210> SEQ ID NO 46
<211> LENGTH: 317
<212> TYPE: PRT
<213> ORGANISM: Mycoplasma bovis

<400> SEQUENCE: 46

Met Glu Asn Glu Asn Leu Lys Val Glu Gln Ala Thr Thr Ala Glu Asn
1               5                   10                  15

Asn Ile Ala Glu Lys Ala Asp Asp Ser Lys Ala Ser Lys Glu Val Lys
            20                  25                  30

Pro Thr Ile Val Ser Arg Glu Lys Leu Leu Glu Ala Gly Thr Tyr Phe
        35                  40                  45

Gly His Lys Lys Ser Met Trp Asn Pro Lys Met Lys Glu Phe Leu Tyr
    50                  55                  60

Pro Gln Ser Lys Arg Gly Met His Met Ile Asn Thr Asn Val Thr Leu
65                  70                  75                  80

Gln Arg Leu Glu Phe Ala Tyr Asn Ile Leu Asn Lys Phe Val Ala Lys
                85                  90                  95

Asn Pro Arg Thr Thr Phe Ile Phe Val Gly Thr Lys Lys Gln Ala Lys
            100                 105                 110

Asp Thr Ile Lys Glu Asn Ala Leu Arg Thr Gly Ser Phe Tyr Val Ser
        115                 120                 125

Glu Arg Trp Leu Gly Gly Thr Leu Thr Asn Ala Ser Thr Ile Phe Lys
    130                 135                 140
```

-continued

```
Arg Val Lys Val Met Glu Glu Leu Glu Ala Gln Ala Ala Lys Lys Phe
145                 150                 155                 160

Gln Gly Tyr Thr Lys Lys Glu Gly Leu Ile Lys Gln Lys Glu Leu Asp
                165                 170                 175

Lys Leu His Lys Asn Leu Asp Gly Ile Arg Lys Met Gln Ser Leu Pro
            180                 185                 190

Ser Phe Met Ile Val Ala Asp Pro Asn Val Asp Ala Ile Ala Val Lys
        195                 200                 205

Glu Ala Arg Ser Lys Gly Val Lys Val Ile Gly Ile Leu Asp Ser Asn
    210                 215                 220

Ser Asn Pro Asp Ala Val Asp Phe Gly Ile Pro Ala Asn Asp Asp Ser
225                 230                 235                 240

Ala Lys Ser Ile Thr Leu Ile Met Thr Ile Leu Ala Asp Ala Ile Ala
                245                 250                 255

Thr Ala Arg Gly Gly Lys Ala Lys Phe Ala Tyr Gln Gly Asp Asp Lys
            260                 265                 270

Val Ile Leu Pro Glu Phe Lys Thr Asp Arg Val Gln Asn Pro Arg Phe
        275                 280                 285

Val Asn Gln Arg Arg Ser Phe Glu Gln Thr Gly Ala Gln Thr Val Arg
    290                 295                 300

Asn Val Glu Lys Thr Thr Thr Ser Ala Glu Val Thr Glu
305                 310                 315


<210> SEQ ID NO 47
<211> LENGTH: 954
<212> TYPE: DNA
<213> ORGANISM: Mycoplasma bovis

<400> SEQUENCE: 47

atggaaaacg aaaacttaaa agttgaacaa gctactacag ctgaaaataa tatagctgaa      60

aaagctgatg attctaaagc ttcaaaagaa gttaaaccta ctattgtttc tagagaaaaa     120

ttattagaag ctggaacata ttttggtcat aaaaaaagta tgtgaaatcc taaaatgaag     180

gaatttctat acccacaatc aaaacgtgga atgcatatga tcaacacaaa tgttacattg     240

caacgtttag aatttgcata caacattttg aacaaatttg ttgctaaaaa tcctagaaca     300

acatttattt ttgttggtac taagaagcaa gctaaagaca caattaaaga aaatgcgtta     360

agaactggca gtttctatgt atctgaaaga tgattaggtg gaacattaac taatgcttct     420

acaattttca aaagagttaa agtaatggaa gaattagaag ctcaagctgc taagaaattc     480

caaggatata ccaaaaaaga aggtctaatc aaacaaaaag aattagacaa attacacaaa     540

aatcttgatg gtataagaaa gatgcaaagc cttccatcat ttatgattgt tgctgaccct     600

aacgttgatg ctatagcagt taaagaagca agaagcaagg gtgtaaaagt tataggtatc     660

ttagactcaa actctaatcc tgatgctgtt gactttggta ttcctgcaaa tgatgattca     720

gctaaaagta ttactttaat tatgacaatt ttagctgacg caatcgctac tgctcgtggt     780

ggaaaagcta aatttgctta ccaaggagat gacaaagtta tattgcctga gttcaaaaca     840

gacagagttc aaaatccaag atttgttaac caaagaagaa gctttgaaca aactggtgcc     900

caaacagtta gaaatgtaga aaaaactaca acaagcgctg aagttacaga ataa           954


<210> SEQ ID NO 48
<211> LENGTH: 954
<212> TYPE: DNA
<213> ORGANISM: Mycoplasma bovis
```

<400> SEQUENCE: 48
atggaaaacg aaaacttaaa agttgaacaa gctactacag ctgaaaataa tatagctgaa 60
aaagctgatg attctaaagc ttcaaaagaa gttaaaccta ctattgtttc tagagaaaaa 120
ttattagaag ctggaacata ttttggtcat aaaaaaagta tgtgaaatcc taaaatgaag 180
gaatttctat acccacaatc aaaacgtgga atgcatatga tcaacacaaa tgttacattg 240
caacgtttag aatttgcata caacattttg aacaaatttg ttgctaaaaa tcctagaaca 300
acatttattt ttgttggtac taagaagcaa gctaaagaca caattaaaga aaatgcgtta 360
agaactggca gtttctatgt atctgaaaga tgattaggtg gaacattaac taatgcttct 420
acaattttca aaagagttaa agtaatggaa gaattagaag ctcaagctgc taagaaattc 480
caaggatata ccaaaaaaga aggtctaatc aaacaaaaag aattagacaa attacacaaa 540
aatcttgatg gtataagaaa gatgcaaagc cttccatcat ttatgattgt tgctgaccct 600
aacgttgatg ctatagcagt taaagaagca agaagcaagg gtgtaaaagt tataggtatc 660
ttagactcaa actctaatcc tgatgctgtt gactttggta ttcctgcaaa tgatgattca 720
gctaaaagta ttactttaat tatgacaatt ttagctgacg caatcgctac tgctcgtggt 780
ggaaaagcta aatttgctta ccaaggagat gacaaagtta tattacctga gttcaaaaca 840
gacagagttc aaaatccaag atttgttaac caaagaagaa gctttgaaca aactggtgcc 900
caaacagtta gaaatgtaga aaaaactaca acaagcgctg aagttacaga ataa 954

<210> SEQ ID NO 49
<211> LENGTH: 203
<212> TYPE: PRT
<213> ORGANISM: Mycoplasma bovis

<400> SEQUENCE: 49

Met Ile Ala Asp Gln Asn Ser Gly Lys Arg Ile Ser Phe Pro Val Glu
1 5 10 15

Gly Ser Ile Ile Asp Val Gln Ala Tyr Lys Tyr Asp Gly Thr Leu Tyr
20 25 30

Arg Gln Trp Asn Gly Val Lys Val Leu Arg Asn Thr Asn Lys His Tyr
35 40 45

Val Leu Leu Met Tyr Lys Thr Arg Val Ser Glu Gln Asn Asn His Asn
50 55 60

Trp Val Tyr Arg Asp Tyr Val Leu Trp Phe Leu Pro Lys His Ser Met
65 70 75 80

Tyr Asn Ala Leu Ile Leu Leu Lys Pro Ser Lys Lys Gln Asn Tyr Ser
85 90 95

Tyr Ile Asn Val Ala Ser Tyr Pro Ile Tyr Glu Asp Asn Thr Ile Lys
100 105 110

Phe Ile Asp Leu Asp Leu Asp Ile Lys Ala Tyr Pro Ser Asn Thr Val
115 120 125

Ser Ile Val Asp Ser Glu Glu Phe Lys Glu Asn Ser Lys Ile Tyr Asn
130 135 140

Tyr Pro Asp Lys Leu Lys Gln Leu Val Trp Glu Gly Thr Gln Glu Val
145 150 155 160

Met Gln His Tyr Glu Arg Gln Gly Tyr Phe Phe Asn Glu Glu Ile Ile
165 170 175

Asn Tyr Tyr Ile Asp Leu Gly Lys Lys Asp Cys Ser Ile Ala Lys Lys
180 185 190

```
Phe Arg Ala Ser Lys Tyr Lys Lys Lys Asn Lys
        195                 200


<210> SEQ ID NO 50
<211> LENGTH: 203
<212> TYPE: PRT
<213> ORGANISM: Mycoplasma bovis
<220> FEATURE:
<221> NAME/KEY: MOD_RES
<222> LOCATION: (16)..(16)
<223> OTHER INFORMATION: Any amino acid

<400> SEQUENCE: 50

Met Ile Ala Asp Gln Asn Ser Gly Lys Arg Ile Ser Phe Pro Val Xaa
1               5                   10                  15

Gly Ser Ile Ile Asp Val Gln Ala Tyr Lys Tyr Asp Gly Thr Leu Tyr
            20                  25                  30

Arg Gln Trp Asn Gly Val Lys Val Leu Arg Asn Thr Asn Lys His Tyr
        35                  40                  45

Val Leu Leu Met Tyr Lys Thr Arg Val Ser Glu Gln Asn Asn His Asn
    50                  55                  60

Trp Val Tyr Arg Asp Tyr Val Leu Trp Phe Leu Pro Lys His Ser Met
65                  70                  75                  80

Tyr Asn Ala Leu Ile Leu Leu Lys Pro Ser Lys Lys Gln Asn Tyr Ser
                85                  90                  95

Tyr Ile Asn Val Ala Ser Tyr Pro Ile Tyr Glu Asp Asn Thr Ile Lys
            100                 105                 110

Phe Ile Asp Leu Asp Leu Asp Ile Lys Ala Tyr Pro Ser Asn Thr Val
        115                 120                 125

Ser Ile Val Asp Ser Glu Glu Phe Lys Glu Asn Ser Lys Ile Tyr Asn
    130                 135                 140

Tyr Pro Asp Lys Leu Lys Gln Leu Val Trp Glu Gly Thr Gln Glu Val
145                 150                 155                 160

Met Gln His Tyr Glu Arg Gln Gly Tyr Phe Phe Asn Glu Glu Ile Ile
                165                 170                 175

Asn Tyr Tyr Ile Asp Leu Gly Lys Lys Asp Cys Ser Ile Ala Lys Lys
            180                 185                 190

Phe Arg Ala Ser Lys Tyr Lys Lys Lys Asn Lys
        195                 200


<210> SEQ ID NO 51
<211> LENGTH: 2707
<212> TYPE: PRT
<213> ORGANISM: Mycoplasma bovis

<400> SEQUENCE: 51

Met Trp Arg Leu Ser Lys Glu Val Phe Lys Ser Leu Ser Lys Asn Lys
1               5                   10                  15

Ile Met Val Ile Gly Leu Ser Ile Leu Ile Phe Ile Thr Ser Ala Val
            20                  25                  30

Phe Thr Leu Leu Ser Ser Leu Arg Ser Ser Ile Val Ser Gly Phe Glu
        35                  40                  45

Asn Tyr Lys Lys Leu Ser Val Lys His Asp Leu Ser Val Asp Leu Asn
    50                  55                  60

Leu Pro Ser Gln Gly Ser Ala Tyr Asn Gln Gly Tyr Phe Val Asn Gly
65                  70                  75                  80

Glu Val Leu Gly Gln Asn Gly Val Lys Glu Tyr Lys Pro Ile Lys Tyr
                85                  90                  95
```

```
Tyr Leu Ala Asn Glu Thr Gly Glu Tyr Arg Asp Ser Val Glu Asn Val
            100                 105                 110

Leu Tyr Leu Gln Asn Thr Glu Phe Ile Lys Leu Ser Asn Phe Thr Gly
        115                 120                 125

Ile Asp Gly Asn Asn Ser Asn Ser Asn Tyr Tyr Ile Arg Arg Asp Asp
    130                 135                 140

Leu Asp Ile Leu Tyr Ser Ile Tyr Ser Ser Asn Lys Asn Asn Ser Ile
145                 150                 155                 160

Val Glu Phe Lys Leu Gly Asn Asp Glu Asn Asp Ala Asn Lys Ala Ser
                165                 170                 175

Phe Lys Leu Lys Gln Ala Asp Arg Thr Phe Asn Ile Tyr Glu Lys Lys
            180                 185                 190

Asn Asp Lys Phe Glu Ile Val Thr Asp Thr Lys Ser Leu Asn Ser Ser
        195                 200                 205

Glu Lys Val Asn Phe Glu Lys Lys Asp Leu Thr Leu Ser Asp Leu Met
    210                 215                 220

Ile Leu Lys Lys Gly Thr Asp Ser Ser Asn Pro Asn Ile Val Tyr Ala
225                 230                 235                 240

Glu Gln Val Gln Pro Leu Phe Ile Asn Val Leu Asp Lys Lys Ile Thr
                245                 250                 255

Asn Glu Tyr Ser Val Gly Asn Asn Trp Val Ala Glu Lys Lys Gly Ile
            260                 265                 270

Ile Ile Pro Ala Asn Glu Trp Ile Glu Lys Phe Gly Phe Lys Lys His
        275                 280                 285

Gly Asp Asn Asp Phe Val Phe Ile Asn Glu Gly Asn Asn Lys Glu Ile
    290                 295                 300

Leu Ser Lys Phe Leu Asp Pro Val Glu Pro Asn Asn Ser Asp Leu Leu
305                 310                 315                 320

Asp Glu Lys Ser Lys Val Lys Ser Glu Trp Thr Ile Ser Asp Phe Tyr
                325                 330                 335

Gly Lys Ser Thr Ile Glu Val Lys Pro Ala Lys Thr Ile Thr Ile Lys
            340                 345                 350

Lys Asp Thr Glu Ile Thr Ile Asn Lys Asn Leu Ile Ala Lys Lys Ser
        355                 360                 365

Arg Asn Val Ser Phe Glu Arg Trp Asn Tyr His Thr Thr Tyr Val Gly
    370                 375                 380

Asp Lys Lys Asn Gln Trp Thr Gly Ala Phe Lys Thr Phe Val Asp Glu
385                 390                 395                 400

Leu Glu Lys Ser Lys Asp Asp His Asn Ser Asp Asn Tyr Arg Lys Trp
                405                 410                 415

Lys Asn Leu Lys Glu Phe Ser Asn Trp Thr Lys Asn Ile Lys Thr Val
            420                 425                 430

Phe Glu Pro Tyr Asp Ser Ser Lys Phe Pro Lys Lys Glu Val Lys Ile
        435                 440                 445

Ser Thr Leu Ile Asn Glu Leu Asp Val Lys Gln Lys Leu Tyr Asn Ser
    450                 455                 460

Asp Asp Thr Asn Asn Asn Ile Ser Glu Ser Arg Ser Asn Phe Pro Gly
465                 470                 475                 480

Gly Ser Ala Tyr Lys Ile Gly Lys Ser Gly Ala Lys Asn Ile Ala Glu
                485                 490                 495

Ile Glu Thr Phe Ile Asp Arg Lys Asp Pro Asn Tyr Glu Arg Lys Leu
            500                 505                 510
```

```
Leu Asp Ala Ile Asn Asp Lys Asp Leu Lys Asn Lys Asn Phe Asn Phe
        515                 520                 525

Ile Lys Gln Glu Ala Tyr Glu Val Thr Lys Asn Ile Ile Ile Asp Lys
    530                 535                 540

Ile Ala Lys Glu Val Gly Gly Arg Lys Asn Ile Gly Leu Arg Lys Thr
545                 550                 555                 560

Ile Thr Val Asp Ala Ile Asp Glu Lys Thr Lys Lys Gln Asn Val Phe
                565                 570                 575

His Phe Ile Asn Thr Gly Asp Glu Asn Gly Glu Val Asp Gly Ile Lys
            580                 585                 590

Leu Asn Val Gly Lys Leu Phe Gly Glu Gln Lys Asn Lys Ser Ala Leu
        595                 600                 605

Ile Pro Thr Asn Arg Phe Asp Glu Ser Val Tyr Arg Gln Asn Gln Leu
    610                 615                 620

Pro Pro Tyr Ile Ala Ser Leu Leu Ile Gln Thr Ile Gly Lys Asn Leu
625                 630                 635                 640

Phe Pro Asp Pro Lys Tyr Val Glu Pro Ile Tyr Glu Phe Ala Glu Val
                645                 650                 655

Thr Asp Met Asn Pro Val Thr Lys Ala Ile Arg Lys Glu Asn Ser Lys
            660                 665                 670

Ile Val Leu Leu Asn Lys Tyr Leu Val Asn Glu Asn Asn Arg Ser Ile
        675                 680                 685

Asp Gln Asn Thr Leu Asp Ser Glu Tyr Lys Lys Leu Asn Leu Gly Ile
    690                 695                 700

Thr Phe Arg Gly Asn Arg Tyr Lys Leu Val Thr Leu Val Asn Ser Asn
705                 710                 715                 720

Asn Gln Leu Phe Trp Lys Thr Val Tyr Ser Glu Gly Ile Asp Gln Leu
                725                 730                 735

Gly Phe Asp Lys Gly Leu Leu Thr Lys Trp Met Glu Gln Asn Lys Val
            740                 745                 750

Thr Leu Ala Thr Lys Phe Ile Lys Thr Asp Asp Glu Gly Trp Val Lys
        755                 760                 765

Lys Asp Gln Ser Leu Ala Asn Ile Ser Tyr Val Pro Thr Gln Phe Leu
    770                 775                 780

Ser Pro Lys Ala Glu Leu Ile Asn Asp Ile Leu Ala Thr Gly Lys Val
785                 790                 795                 800

Asp Phe Leu Ser Asn Ala Ile Glu Lys Glu Leu Leu Asp Ser Ala Leu
                805                 810                 815

Val Lys Glu Glu Phe Ile Ser Gln Glu Asn Val Phe Leu Ile Ala Asn
            820                 825                 830

Ala Leu Lys Lys Val Leu Asn Asn Asn Asn Phe Ala Ser Ala Phe Thr
        835                 840                 845

Ser Ser Lys Ile Asn Arg Glu Leu Leu Pro Lys Ile Gly Leu Asp Leu
    850                 855                 860

Leu Tyr Glu Leu Ser His Ser Asp Ser Gly Asn Ile Phe Lys Ser Val
865                 870                 875                 880

Leu Phe Asn Ile Phe Glu Lys Val Lys Ala Lys Ile Ser Glu Lys Gly
                885                 890                 895

Ser Leu Glu Asn Gln Lys Lys Tyr Val Ile Asp Glu Val Asn Asn Ile
            900                 905                 910

Tyr Ser Leu Ile Asn Gly Leu Ala Gly Ile Asp Ile Ser Lys Tyr Leu
        915                 920                 925

Ser Ala Glu Asp Ile Val Asn Phe Ser Lys Glu Pro Lys Lys Val Ile
```

```
    930                 935                 940

Asp Ala Phe Gln Asn Ile Ile Thr Ser Ile Asp Ala Tyr Lys Phe Ser
945                 950                 955                 960

Gln Tyr Ala Asn Asp Trp Tyr Lys Asn Glu Trp Arg Lys Gln Val Asp
                965                 970                 975

His Asn Lys Asp Lys Tyr Thr Asn Arg Leu Ser Ser Gly Leu Leu Ile
            980                 985                 990

Asn Trp Leu Phe Lys Ser Val Asp  Gln Lys Thr Leu Lys  Thr Gly Leu
        995                 1000                 1005

Lys Ile  Leu Ile Asn Asn Leu  Asp Phe Glu Lys Ile  Val Asn Leu
    1010                 1015                 1020

Asp Asp  Lys Asn Ser Phe Leu  Tyr Lys Lys Leu Asn  Ser Ser Val
    1025                 1030                 1035

Pro Ser  Leu Ile Asp Gly Ile  Asn Val Leu Leu Lys  Lys Ile Ser
    1040                 1045                 1050

Lys Asp  Gly Lys Phe Asp Asn  Ile Lys Glu Gly Leu  Asn Lys Ile
    1055                 1060                 1065

Leu Gln  Asn Ile Asp Phe Asn  Val Leu Ser Lys Tyr  Leu Asp Asp
    1070                 1075                 1080

His Leu  Glu Thr Asn Tyr Phe  Glu Tyr Lys Lys Ser  Thr Phe Asp
    1085                 1090                 1095

Tyr Glu  Leu Asn Lys Glu Lys  Val Leu Lys Glu Lys  Val Ala Leu
    1100                 1105                 1110

Lys Thr  Ile Arg Pro Lys Asp  Gly Met Met Ala Leu  Ile Tyr Gly
    1115                 1120                 1125

Leu Phe  Lys Asn Pro Gly Thr  Asn Arg Glu Phe Lys  Asp Asn Leu
    1130                 1135                 1140

Ile Lys  Met Phe Asn Leu Ser  Ser Lys Val Asn Glu  Ser Asn Val
    1145                 1150                 1155

Glu Asn  Gly Thr Gly Thr Ile  Ile Thr Pro Asp Ser  Asp Pro Asp
    1160                 1165                 1170

Lys Leu  Ser Phe Ser Asp Phe  Leu Ala Phe Phe Leu  Ala Leu Leu
    1175                 1180                 1185

Ser Ala  Asp Gln Ser Lys Ala  Ile Phe Lys Asn Gln  Gln Ile Phe
    1190                 1195                 1200

Asn Glu  Ile Asp Lys Ala Lys  Gln His Ile Ile Ser  Val Leu Leu
    1205                 1210                 1215

His Lys  Arg Asn Ser Ala Asn  Ile Phe Asp Leu Asp  Ile Lys Val
    1220                 1225                 1230

Val Glu  Thr Leu Lys Arg Phe  Asn Val Ile Ser Asn  Glu Thr Ile
    1235                 1240                 1245

Ile Asn  Gln Gln Val Ile Asp  Lys Leu Thr Asn Ile  Glu Asn Phe
    1250                 1255                 1260

Leu Lys  Gln Thr Thr Thr Ser  Ile Asn Glu Lys Ile  Lys Val Val
    1265                 1270                 1275

Asp Glu  Lys Asn Lys Thr Leu  Ala Asp Leu Ile Tyr  Asp Phe Asn
    1280                 1285                 1290

Asn Phe  Ser Asp Gly Asp Ala  Thr Trp Arg Thr Trp  Lys Ser Leu
    1295                 1300                 1305

Ile Gly  Ala Tyr Gly Gln Ala  Ser Ile Thr Asn Lys  Phe Ser Leu
    1310                 1315                 1320

Gly Ala  Gln Ala Phe Asp Leu  Leu Leu Pro Trp Ile  Asn Met Leu
    1325                 1330                 1335
```

Ala Phe Asn Lys Glu Ala Asn Gln Lys Glu Ala Leu Lys Phe Ile
1340 1345 1350

Asn Asp Phe Leu Lys Leu Ser Ile Asp Pro Asp Ile Leu Lys Asp
1355 1360 1365

Ile Asn Lys Leu Ala Glu Asp Glu Asn Leu Pro Ser Ser Ala Asp
1370 1375 1380

Asn Lys Phe Gly Leu Ser Ile Ala Leu His Arg Pro Glu Gln Val
1385 1390 1395

Thr Leu Phe Asn Gln Asn Asn Asp Lys Phe Thr Asn Ala Lys Val
1400 1405 1410

Glu Lys Leu Ala Ser Glu Asn Pro Lys Phe Arg Lys Tyr Leu Ile
1415 1420 1425

Ser Gln Lys Arg Ser Leu Ile Glu Leu Leu Gly Leu Ile Gly Ala
1430 1435 1440

Ser Gln Gln Tyr Ser Lys Tyr Glu Thr Lys Pro Thr Glu Glu Gly
1445 1450 1455

Lys Ile Tyr Ala Pro Tyr Gly Ile Tyr Tyr Glu Thr Ile Lys Lys
1460 1465 1470

Ser Val Asp Lys Tyr Phe Ser Thr Lys Glu Phe Trp Asp Ile Arg
1475 1480 1485

Asp Ile Ala Leu Ser Ile Thr Arg Ser Met Gln Ile Asn Phe Pro
1490 1495 1500

Ile Glu Leu Phe Asp Leu Ser Arg Ile Ile Ile Asn Pro Val Leu
1505 1510 1515

Arg Ser Met Tyr Pro Gln Leu Met Thr Ser Phe Val Ser Thr Gln
1520 1525 1530

Lys Lys Asn Leu Gly Ser Ile Asn Gly Asn Leu Ala Tyr Ile Val
1535 1540 1545

Leu Ser Arg Ile Gly Asn Phe Glu Glu Ile Ile Arg Asp Glu Ser
1550 1555 1560

Lys Lys Ser Glu Leu Glu Ala Tyr Phe Glu Gln Ile Trp Ser Asn
1565 1570 1575

Asn Asp Thr Ser Leu Val Pro Leu Asp Tyr Asn Glu Glu Ile Thr
1580 1585 1590

Leu Ser Leu Asp Gly Ala Arg Ile Asn Lys Leu Phe Asn Glu Asn
1595 1600 1605

Asn Lys Lys Thr Thr Val Phe Gly Ile Asp Phe Met Asn Leu Ala
1610 1615 1620

Gly Lys Val Ile Asn Gly Ile Val Glu Pro Lys Glu Leu Lys Asp
1625 1630 1635

Ile Val Phe Asn Asp Ile Asn Ser Tyr Tyr Ala Lys Val Asn Tyr
1640 1645 1650

Ala Tyr Leu Ala Lys Asn Asn Lys Ala Ile Tyr Asn Gly Thr Leu
1655 1660 1665

Pro Lys Asn Asn Val Glu Met Glu Ser Leu Ile Asn Thr Ile Asp
1670 1675 1680

Asp Lys Tyr Ile Leu Asp Val Asn Gly Ile Lys Phe Leu Ile Val
1685 1690 1695

Gly Glu Asp Thr Thr Ile Asp Tyr Ile Tyr Pro Val Ile Asp Glu
1700 1705 1710

Asn His Leu Gln Val Asn Thr Gln Asn Gln Ala Leu Val Tyr Leu
1715 1720 1725

```
Asn Asn  Tyr Gly Phe Ser Arg  Val Val Ala Ala Tyr  Gln Gly Asn
    1730                 1735                 1740

Val Ile  Lys Lys Asn Leu Leu  Val Val Asn Gly Ser  Lys Asn Ser
    1745                 1750                 1755

Asn Glu  Val Ala Lys Arg Asn  Ile Ile Asn Ile Val  Asp Ser Ser
    1760                 1765                 1770

Ile Ser  Asp Ala Asn Lys Leu  Lys Arg Val Phe Leu  Tyr Asn Glu
    1775                 1780                 1785

Leu Asp  Pro Ile Asn Pro Glu  Arg Ala Leu Arg Ile  Thr Thr Ile
    1790                 1795                 1800

Glu Arg  Met Ile Gly Val Ile  Ser Ser Ser Ile Ile  Ala Leu Met
    1805                 1810                 1815

Thr Leu  Phe Ile Ile Met Val  Ser Val Ala Ile Ile  Phe Ile Ile
    1820                 1825                 1830

Arg Arg  Tyr Ile Ala Asn Lys  Ala Lys Val Phe Gly  Ile Leu Leu
    1835                 1840                 1845

Ala Gln  Gly Tyr Lys Pro Ile  Glu Ile Ala Ile Ser  Leu Leu Ser
    1850                 1855                 1860

Phe Ala  Ala Val Thr Ser Leu  Ile Gly Gly Ile Leu  Gly Tyr Ser
    1865                 1870                 1875

Ile Gly  Phe Arg Thr Gln Ile  Leu Leu Gln Asn Val  Phe Ser Asn
    1880                 1885                 1890

Tyr Trp  Thr Leu Pro Lys Ser  Ala Ile Pro Phe Asp  Phe Phe Ala
    1895                 1900                 1905

Leu Phe  Phe Asn Val Phe Ile  Pro Phe Ile Gly Met  Ser Leu Leu
    1910                 1915                 1920

Ile Ile  Val Val Ala Leu Ile  Ser Leu Arg Lys Ser  Ser Ile Asp
    1925                 1930                 1935

Leu Ile  Thr Gly Val Asp Glu  Ala Pro Lys Gly Lys  Leu Phe Thr
    1940                 1945                 1950

Phe Met  Lys Lys Lys Phe Ile  Asn Lys Lys Asn Val  Lys Lys Arg
    1955                 1960                 1965

Phe Arg  Phe Thr Leu Ala Tyr  Ser Gly Phe Trp Lys  Leu Ala Ser
    1970                 1975                 1980

Phe Gly  Gly Ser Val Leu Leu  Thr Ser Ile Ala Thr  Met Phe Gly
    1985                 1990                 1995

Leu Ala  Asn Phe Lys Ser Phe  Asn Lys Thr Ile Asn  Asp Thr Tyr
    2000                 2005                 2010

Lys Asn  Arg Asp Tyr Lys Phe  Lys Val Asp Leu Glu  Ser Pro Thr
    2015                 2020                 2025

Val Glu  Gly Gly Asp Tyr Ser  Leu Tyr Asn Pro Lys  Glu Leu Asn
    2030                 2035                 2040

Asn Leu  Ile Tyr Thr Pro Ile  Gly Ser Leu Asn Glu  Gly Asn Arg
    2045                 2050                 2055

Glu Thr  Ala Asp Tyr Phe Lys  Pro Gly Lys Ser Ser  Ile Ile Asn
    2060                 2065                 2070

Pro Asn  Asn Asn Asp Asn Gly  Met Pro Ser Asp Lys  Ser Pro His
    2075                 2080                 2085

Ile Leu  Ser Gln Phe Ser Val  Asn Val Thr Val Asp  Ala Gly Val
    2090                 2095                 2100

Ser Ala  Asp Pro Trp Leu Ile  Ala Tyr Asn Gly Met  Pro Asp Ser
    2105                 2110                 2115

Gln Lys  Ala Lys Ile Asp Lys  Ile Arg Asp Leu Val  Gly His Gln
```

```
    2120                2125                2130

Leu Glu  Trp Thr Gln Ser Leu  Asp Asp Asn Gly Glu  Leu Ile Thr
    2135                2140                2145

Asp Pro  Asn Lys Pro Ile Ile  Lys Val Asp Ser Asn  Gly Leu Met
    2150                2155                2160

Ser Tyr  Glu Asp Gly Thr Gly  Lys Lys Tyr Asp Phe  Phe Lys Tyr
    2165                2170                2175

Tyr Lys  Ser Pro Asn Asp Lys  Gln Gly Ser Phe Arg  Leu Ala His
    2180                2185                2190

Trp Asp  Glu Val Asn Lys Glu  Tyr Val Met Lys Ile  Ile Lys Thr
    2195                2200                2205

Gly Asn  Ser Gly Gly Arg Asn  Glu Tyr Arg Asp Phe  Leu Val Arg
    2210                2215                2220

Ala Tyr  Lys Lys Asn Asp Val  Ile Arg Lys Gln His  Glu Lys Met
    2225                2230                2235

Ile Ala  Ser Gly Lys Ser Ile  Thr Asn Pro Ile Ser  Asn Trp Thr
    2240                2245                2250

Lys Ser  Asn Asn Ser Ser Asp  Phe Trp Leu Ile Asp  Lys Ser Asp
    2255                2260                2265

Leu Asn  Arg Gln Trp Val Asn  Asp Tyr Phe Ile Gly  Phe Gly Gly
    2270                2275                2280

Val Leu  Phe Asp Lys Ser Tyr  Asp Glu Thr Tyr Thr  Tyr Leu Ser
    2285                2290                2295

Gly Thr  Tyr Asn Asn Val Ser  Ala Lys Ile Tyr Gly  Tyr Arg Lys
    2300                2305                2310

Pro Val  Asp Phe Lys Asn Ala  Lys Val Lys Leu Ile  Asp Lys Ala
    2315                2320                2325

Gly Asn  Asn Leu Tyr Glu Val  Leu Asp Lys Tyr Glu  Val Lys Asn
    2330                2335                2340

Asn Val  Tyr Pro Leu Val Val  Asn Asp Val Phe Ala  Lys Lys His
    2345                2350                2355

Lys Leu  Gly Ile Asn Asp Leu  Ile Asp Phe Lys Val  Trp Asn Arg
    2360                2365                2370

Val Asp  Arg Tyr Lys Gln Lys  Ile Ile Glu Lys Ile  Tyr Ala Asn
    2375                2380                2385

Asp Pro  Val Lys Gln Ala Asp  Leu Lys Asn Glu Tyr  Asn Lys Lys
    2390                2395                2400

Thr Asn  Ala Lys Phe Gln Ile  Val Gly Ile Asn Pro  Thr Tyr Ile
    2405                2410                2415

Asn Asp  Glu Leu Ile Thr Thr  His Lys Ala Ala Asn  Leu Leu Ile
    2420                2425                2430

Gly Met  Thr Asp Ile Asp Asn  Gly Phe Asn Gly Val  Leu Thr Gln
    2435                2440                2445

Asn Ala  Asn Pro Val Gln Val  Thr Glu Ser Ala Gly  Leu Tyr Ser
    2450                2455                2460

Val Ser  Gly Tyr Trp Ala Gly  Leu Asp Gly Phe Asp  Val Ser Ser
    2465                2470                2475

Leu Asp  Asn Gly Thr Val Glu  Lys Met Phe Asp Glu  Ile Phe Gly
    2480                2485                2490

Ser Pro  Asp Lys Lys Gly Val  Leu Glu Thr Gln His  Gly Leu Thr
    2495                2500                2505

Lys Asn  Glu Ile Ala Lys Phe  Leu Asp Ser Ser Ala  Asn Glu Phe
    2510                2515                2520
```

Ser Lys Ser Leu Tyr Glu Ser Ala Lys Ser Ser Ala Lys Leu His
2525 2530 2535

Ile Asp Glu Phe Ser Lys Ile Tyr Asn Asn Lys Leu Tyr Ile Ala
2540 2545 2550

Leu Ser Ser Ser Ile Asp Ser Lys Asp Ile Glu Val Gly Phe Val
2555 2560 2565

Leu Gln Val Gly Ser Thr Ile Glu Gln Ile Ser Ile Phe Ile Ile
2570 2575 2580

Val Ile Asn Phe Val Ile Ser Leu Ile Ile Leu Ile Ile Met Ser
2585 2590 2595

Ser Ile Ile Val Ser Glu Asn Glu Arg Asn Ile Ala Ile Trp Ser
2600 2605 2610

Ile Leu Gly Tyr Ser Gln Lys Glu Lys Leu Met Met Phe Phe Gly
2615 2620 2625

Ala Phe Ile Pro Phe Leu Val Ser Ala Ile Val Ile Ser Ile Pro
2630 2635 2640

Ile Val Ile Ala Leu Ile Ser Val Phe Ser Gly Phe Leu Leu Ser
2645 2650 2655

Ser Ser Ser Ile Ala Leu Leu Leu Ser Leu Lys Trp Trp His Val
2660 2665 2670

Leu Ile Thr Ser Gly Leu Met Leu Thr Ile Phe Ala Ile Thr Ser
2675 2680 2685

Ile Ser Val Trp Ile Thr Ile Asn Lys Met Lys Pro Val Asp Leu
2690 2695 2700

Leu Lys Gly Lys
2705

<210> SEQ ID NO 52
<211> LENGTH: 2707
<212> TYPE: PRT
<213> ORGANISM: Mycoplasma bovis

<400> SEQUENCE: 52

Met Trp Arg Leu Ser Lys Glu Val Phe Lys Ser Leu Ser Lys Asn Lys
1 5 10 15

Ile Met Val Ile Gly Leu Ser Ile Leu Ile Phe Ile Thr Ser Ala Val
20 25 30

Phe Thr Leu Leu Ser Ser Leu Arg Ser Ser Ile Val Ser Gly Phe Glu
35 40 45

Asn Tyr Lys Lys Leu Ser Val Lys His Asp Leu Ser Val Asp Leu Asn
50 55 60

Leu Pro Ser Gln Gly Ser Ala Tyr Asn Gln Gly Tyr Phe Val Asn Gly
65 70 75 80

Glu Val Leu Gly Gln Asn Gly Val Lys Glu Tyr Lys Pro Ile Lys Tyr
85 90 95

Tyr Leu Ala Asn Glu Thr Gly Glu Tyr Arg Asp Ser Val Glu Asn Val
100 105 110

Leu Tyr Leu Gln Asn Thr Glu Phe Ile Lys Leu Ser Asn Phe Thr Gly
115 120 125

Ile Asp Gly Asn Asn Ser Asn Ser Asn Tyr Tyr Ile Arg Arg Asp Asp
130 135 140

Leu Asp Ile Leu Tyr Ser Ile Tyr Ser Ser Asn Lys Asn Asn Ser Ile
145 150 155 160

Val Glu Phe Lys Leu Gly Asn Asp Glu Asn Asp Ala Asn Lys Ala Ser

-continued

```
                165                 170                 175

Phe Lys Leu Lys Gln Ala Asp Arg Thr Phe Asn Ile Tyr Glu Lys Lys
            180                 185                 190

Asn Asp Lys Phe Glu Ile Val Thr Asp Thr Lys Ser Leu Asn Ser Ser
        195                 200                 205

Glu Lys Val Asn Phe Glu Lys Lys Asp Leu Thr Leu Ser Asp Leu Met
    210                 215                 220

Ile Leu Lys Lys Gly Thr Asp Ser Ser Asn Pro Asn Ile Val Tyr Ala
225                 230                 235                 240

Glu Gln Val Gln Pro Leu Phe Ile Asn Val Leu Asp Lys Lys Ile Thr
                245                 250                 255

Asn Glu Tyr Ser Val Gly Asn Asn Trp Val Ala Glu Lys Lys Gly Ile
            260                 265                 270

Ile Ile Pro Ala Asn Glu Trp Ile Glu Lys Phe Gly Phe Lys Lys His
        275                 280                 285

Gly Asp Asn Asp Phe Val Phe Ile Asn Glu Gly Asn Asn Lys Glu Ile
    290                 295                 300

Leu Ser Lys Phe Leu Asp Pro Val Glu Pro Asn Asn Ser Asp Leu Leu
305                 310                 315                 320

Asp Glu Lys Ser Lys Val Lys Ser Glu Trp Thr Ile Ser Asp Phe Tyr
                325                 330                 335

Gly Lys Ser Thr Ile Glu Val Lys Pro Ala Lys Thr Ile Thr Ile Lys
            340                 345                 350

Lys Asp Thr Glu Ile Thr Ile Asn Lys Asn Leu Ile Ala Lys Lys Ser
        355                 360                 365

Arg Asn Val Ser Phe Glu Arg Trp Asn Tyr His Thr Thr Tyr Val Gly
    370                 375                 380

Asp Lys Lys Asn Gln Trp Thr Gly Ala Phe Lys Thr Phe Val Asp Glu
385                 390                 395                 400

Leu Glu Lys Ser Lys Asp Asp His Asn Ser Asp Asn Tyr Arg Lys Trp
                405                 410                 415

Lys Asn Leu Lys Glu Phe Ser Asn Trp Thr Lys Asn Ile Lys Thr Val
            420                 425                 430

Phe Glu Pro Tyr Asp Ser Ser Lys Phe Pro Lys Lys Glu Val Lys Ile
        435                 440                 445

Ser Thr Leu Ile Asn Glu Leu Asp Val Lys Gln Lys Leu Tyr Asn Ser
    450                 455                 460

Asp Asp Thr Asn Asn Asn Ile Ser Glu Ser Arg Ser Asn Phe Pro Gly
465                 470                 475                 480

Gly Ser Ala Tyr Lys Ile Gly Lys Ser Gly Ala Lys Asn Ile Ala Glu
                485                 490                 495

Ile Glu Thr Phe Ile Asp Arg Lys Asp Pro Asn Tyr Glu Arg Lys Leu
            500                 505                 510

Leu Asp Ala Ile Asn Asp Lys Asp Leu Lys Asn Lys Asn Phe Asn Phe
        515                 520                 525

Ile Lys Gln Glu Ala Tyr Glu Val Thr Lys Asn Ile Ile Asp Lys
    530                 535                 540

Ile Ala Lys Glu Val Gly Gly Arg Lys Asn Ile Gly Leu Arg Lys Thr
545                 550                 555                 560

Ile Thr Val Asp Ala Ile Asp Glu Lys Thr Lys Lys Gln Asn Val Phe
                565                 570                 575

His Phe Ile Asn Thr Gly Asp Glu Asn Gly Glu Val Asp Gly Ile Lys
            580                 585                 590
```

-continued

```
Leu Asn Val Gly Lys Leu Phe Gly Glu Gln Lys Asn Lys Ser Ala Leu
        595                 600                 605

Ile Pro Thr Asn Arg Phe Asp Glu Ser Val Tyr Arg Gln Asn Gln Leu
    610                 615                 620

Pro Pro Tyr Ile Ala Ser Leu Leu Ile Gln Thr Ile Gly Lys Asn Leu
625                 630                 635                 640

Phe Pro Asp Pro Lys Tyr Val Glu Pro Ile Tyr Glu Phe Ala Glu Val
                645                 650                 655

Thr Asp Met Asn Pro Val Thr Lys Ala Ile Arg Lys Glu Asn Ser Lys
            660                 665                 670

Ile Val Leu Leu Asn Lys Tyr Leu Val Asn Glu Asn Asn Arg Ser Ile
        675                 680                 685

Asp Gln Asn Thr Leu Asp Ser Glu Tyr Lys Lys Leu Asn Leu Gly Ile
    690                 695                 700

Thr Phe Arg Gly Asn Arg Tyr Lys Leu Val Thr Leu Val Asn Ser Asn
705                 710                 715                 720

Asn Gln Leu Phe Trp Lys Thr Val Tyr Ser Glu Gly Ile Asp Gln Leu
                725                 730                 735

Gly Phe Asp Lys Gly Leu Leu Thr Lys Trp Met Glu Gln Asn Lys Val
            740                 745                 750

Thr Leu Ala Thr Lys Phe Ile Lys Thr Asp Asp Glu Gly Trp Val Lys
        755                 760                 765

Lys Asp Gln Ser Leu Ala Asn Ile Ser Tyr Val Pro Thr Gln Phe Leu
    770                 775                 780

Ser Pro Lys Ala Glu Leu Ile Asn Asp Ile Leu Ala Thr Gly Lys Val
785                 790                 795                 800

Asp Phe Leu Ser Asn Ala Ile Glu Lys Glu Leu Leu Asp Ser Ala Leu
                805                 810                 815

Val Lys Glu Glu Phe Ile Ser Gln Glu Asn Val Phe Leu Ile Ala Asn
            820                 825                 830

Ala Leu Lys Lys Val Leu Asn Asn Asn Asn Phe Ala Ser Ala Phe Thr
        835                 840                 845

Ser Ser Lys Ile Asn Arg Glu Leu Leu Pro Lys Ile Gly Leu Asp Leu
    850                 855                 860

Leu Tyr Glu Leu Ser His Ser Asp Ser Gly Asn Ile Phe Lys Ser Val
865                 870                 875                 880

Leu Phe Asn Ile Phe Glu Lys Val Lys Ala Lys Ile Ser Glu Lys Gly
                885                 890                 895

Ser Leu Glu Asn Gln Lys Lys Tyr Val Ile Asp Glu Val Asn Asn Ile
            900                 905                 910

Tyr Ser Leu Ile Asn Gly Leu Ala Gly Ile Asp Ile Ser Lys Tyr Leu
        915                 920                 925

Ser Ala Glu Asp Ile Val Asn Phe Ser Lys Glu Pro Lys Lys Val Ile
    930                 935                 940

Asp Ala Phe Gln Asn Ile Ile Thr Ser Ile Asp Ala Tyr Lys Phe Ser
945                 950                 955                 960

Gln Tyr Ala Asn Asp Trp Tyr Lys Asn Glu Trp Arg Lys Gln Val Asp
                965                 970                 975

His Asn Lys Asp Lys Tyr Thr Asn Arg Leu Ser Ser Gly Leu Leu Ile
            980                 985                 990

Asn Trp Leu Phe Lys Ser Val Asp  Gln Lys Thr Leu Lys  Thr Gly Leu
        995                 1000                1005
```

Lys Ile Leu Ile Asn Asn Leu Asp Phe Glu Lys Ile Val Asn Leu
1010 1015 1020

Asp Asp Lys Asn Ser Phe Leu Tyr Lys Lys Leu Asn Ser Ser Val
1025 1030 1035

Pro Ser Leu Ile Asp Gly Ile Asn Val Leu Leu Lys Lys Ile Ser
1040 1045 1050

Lys Asp Gly Lys Phe Asp Asn Ile Lys Glu Gly Leu Asn Lys Ile
1055 1060 1065

Leu Gln Asn Ile Asp Phe Asn Val Leu Ser Lys Tyr Leu Asp Asp
1070 1075 1080

His Leu Glu Thr Asn Tyr Phe Glu Tyr Lys Lys Ser Thr Phe Asp
1085 1090 1095

Tyr Glu Leu Asn Lys Glu Lys Val Leu Lys Glu Lys Val Ala Leu
1100 1105 1110

Lys Thr Ile Arg Pro Lys Asp Gly Met Met Ala Leu Ile Tyr Gly
1115 1120 1125

Leu Phe Lys Asn Pro Gly Thr Asn Arg Glu Phe Lys Asp Asn Leu
1130 1135 1140

Ile Lys Met Phe Asn Leu Ser Ser Lys Val Asn Glu Ser Asn Val
1145 1150 1155

Glu Asn Gly Thr Gly Thr Ile Ile Thr Pro Asp Ser Asp Pro Asp
1160 1165 1170

Lys Leu Ser Phe Ser Asp Phe Leu Ala Phe Phe Leu Ala Leu Leu
1175 1180 1185

Ser Ala Asp Gln Ser Lys Ala Ile Phe Lys Asn Gln Gln Ile Phe
1190 1195 1200

Asn Glu Ile Asp Lys Ala Lys Gln His Ile Ile Ser Val Leu Leu
1205 1210 1215

His Lys Arg Asn Ser Ala Asn Ile Phe Asp Leu Asp Ile Lys Val
1220 1225 1230

Val Glu Thr Leu Lys Arg Phe Asn Val Ile Ser Asn Glu Thr Ile
1235 1240 1245

Ile Asn Gln Gln Val Ile Asp Lys Leu Thr Asn Ile Glu Asn Phe
1250 1255 1260

Leu Lys Gln Thr Thr Thr Ser Ile Asn Glu Lys Ile Lys Val Val
1265 1270 1275

Asp Glu Lys Asn Lys Thr Leu Ala Asp Leu Ile Tyr Asp Phe Asn
1280 1285 1290

Asn Phe Ser Asp Gly Asp Ala Thr Trp Arg Thr Trp Lys Ser Leu
1295 1300 1305

Ile Gly Ala Tyr Gly Gln Ala Ser Ile Thr Asn Lys Phe Ser Leu
1310 1315 1320

Gly Ala Gln Ala Phe Asp Leu Leu Leu Pro Trp Ile Asn Met Leu
1325 1330 1335

Ala Phe Asn Lys Glu Ala Asn Gln Lys Glu Ala Leu Lys Phe Ile
1340 1345 1350

Asn Asp Phe Leu Lys Leu Ser Ile Asp Pro Asp Ile Leu Lys Asp
1355 1360 1365

Ile Asn Lys Leu Ala Glu Asp Glu Asn Leu Pro Ser Ser Ala Asp
1370 1375 1380

Asn Lys Phe Gly Leu Ser Ile Ala Leu His Arg Pro Glu Gln Val
1385 1390 1395

Thr Leu Phe Asn Gln Asn Asn Asp Lys Phe Thr Asn Ala Lys Val

```
    1400                1405                1410

Glu Lys  Leu Ala Ser Glu Asn  Pro Lys Phe Arg Lys  Tyr Leu Ile
    1415                1420                1425

Ser Gln  Lys Arg Ser Leu Ile  Glu Leu Leu Gly Leu  Ile Gly Ala
    1430                1435                1440

Ser Gln  Gln Tyr Ser Lys Tyr  Glu Thr Lys Pro Thr  Glu Glu Gly
    1445                1450                1455

Lys Ile  Tyr Ala Pro Tyr Gly  Ile Tyr Tyr Glu Thr  Ile Lys Lys
    1460                1465                1470

Ser Val  Asp Lys Tyr Phe Ser  Thr Lys Glu Phe Trp  Asp Ile Arg
    1475                1480                1485

Asp Ile  Ala Leu Ser Ile Thr  Arg Ser Met Gln Ile  Asn Phe Pro
    1490                1495                1500

Ile Glu  Leu Phe Asp Leu Ser  Arg Ile Ile Ile Asn  Pro Val Leu
    1505                1510                1515

Arg Ser  Met Tyr Pro Gln Leu  Met Thr Ser Phe Val  Ser Thr Gln
    1520                1525                1530

Lys Lys  Asn Leu Gly Ser Ile  Asn Gly Asn Leu Ala  Tyr Ile Val
    1535                1540                1545

Leu Ser  Arg Ile Gly Asn Phe  Glu Glu Ile Ile Arg  Asp Glu Ser
    1550                1555                1560

Lys Lys  Ser Glu Leu Glu Ala  Tyr Phe Glu Gln Ile  Trp Ser Asn
    1565                1570                1575

Asn Asp  Thr Ser Leu Val Pro  Leu Asp Tyr Asn Glu  Glu Ile Thr
    1580                1585                1590

Leu Ser  Leu Asp Gly Ala Arg  Ile Asn Lys Leu Phe  Asn Glu Asn
    1595                1600                1605

Asn Lys  Lys Thr Thr Val Phe  Gly Ile Asp Phe Met  Asn Leu Ala
    1610                1615                1620

Gly Lys  Val Ile Asn Gly Ile  Val Glu Pro Lys Glu  Leu Lys Asp
    1625                1630                1635

Ile Val  Phe Asn Asp Ile Asn  Ser Tyr Tyr Ala Lys  Val Asn Tyr
    1640                1645                1650

Ala Tyr  Leu Ala Lys Asn Asn  Lys Ala Ile Tyr Asn  Gly Thr Leu
    1655                1660                1665

Pro Lys  Asn Asn Val Glu Met  Glu Ser Leu Ile Asn  Thr Ile Asp
    1670                1675                1680

Asp Lys  Tyr Ile Leu Asp Val  Asn Gly Ile Lys Phe  Leu Ile Val
    1685                1690                1695

Gly Glu  Asp Thr Thr Ile Asp  Tyr Ile Tyr Pro Val  Ile Asp Glu
    1700                1705                1710

Asn His  Leu Gln Val Asn Thr  Gln Asn Gln Ala Leu  Val Tyr Leu
    1715                1720                1725

Asn Asn  Tyr Gly Phe Ser Arg  Val Val Ala Ala Tyr  Gln Gly Asn
    1730                1735                1740

Val Ile  Lys Lys Asn Leu Leu  Val Val Asn Gly Ser  Lys Asn Ser
    1745                1750                1755

Asn Glu  Val Ala Lys Arg Asn  Ile Ile Asn Ile Val  Asp Ser Ser
    1760                1765                1770

Ile Ser  Asp Ala Asn Lys Leu  Lys Arg Val Phe Leu  Tyr Asn Glu
    1775                1780                1785

Leu Asp  Pro Ile Asn Pro Glu  Arg Ala Leu Arg Ile  Thr Thr Ile
    1790                1795                1800
```

```
Glu Arg  Met Ile Gly Val Ile  Ser Ser Ser Ile Ile  Ala Leu Met
    1805                 1810                 1815

Thr Leu  Phe Ile Ile Met Val  Ser Val Ala Ile Ile  Phe Ile Ile
    1820                 1825                 1830

Arg Arg  Tyr Ile Ala Asn Lys  Ala Lys Val Phe Gly  Ile Leu Leu
    1835                 1840                 1845

Ala Gln  Gly Tyr Lys Pro Ile  Glu Ile Ala Ile Ser  Leu Leu Ser
    1850                 1855                 1860

Phe Ala  Ala Val Thr Ser Leu  Ile Gly Gly Ile Leu  Gly Tyr Ser
    1865                 1870                 1875

Ile Gly  Phe Arg Thr Gln Ile  Leu Leu Gln Asn Val  Phe Ser Asn
    1880                 1885                 1890

Tyr Trp  Thr Leu Pro Lys Ser  Ala Ile Pro Phe Asp  Phe Phe Ala
    1895                 1900                 1905

Leu Phe  Phe Asn Val Phe Ile  Pro Phe Ile Gly Met  Ser Leu Leu
    1910                 1915                 1920

Ile Ile  Val Val Ala Leu Ile  Ser Leu Arg Lys Ser  Ser Ile Asp
    1925                 1930                 1935

Leu Ile  Thr Gly Val Asp Glu  Ala Pro Lys Gly Lys  Leu Phe Thr
    1940                 1945                 1950

Phe Met  Lys Lys Lys Phe Ile  Asn Lys Lys Asn Val  Lys Lys Arg
    1955                 1960                 1965

Phe Arg  Phe Thr Leu Ala Tyr  Ser Gly Phe Trp Lys  Leu Ala Ser
    1970                 1975                 1980

Phe Gly  Gly Ser Val Leu Leu  Thr Ser Ile Ala Thr  Met Phe Gly
    1985                 1990                 1995

Leu Ala  Asn Phe Lys Ser Phe  Asn Lys Thr Ile Asn  Asp Thr Tyr
    2000                 2005                 2010

Lys Asn  Arg Asp Tyr Lys Phe  Lys Val Asp Leu Glu  Ser Pro Thr
    2015                 2020                 2025

Val Glu  Gly Gly Asp Tyr Ser  Leu Tyr Asn Pro Lys  Glu Leu Asn
    2030                 2035                 2040

Asn Leu  Ile Tyr Thr Pro Ile  Gly Ser Leu Asn Glu  Gly Asn Arg
    2045                 2050                 2055

Glu Thr  Ala Asp Tyr Phe Lys  Pro Gly Lys Ser Ser  Ile Ile Asn
    2060                 2065                 2070

Pro Asn  Asn Asn Asp Asn Gly  Met Pro Ser Asp Lys  Ser Pro His
    2075                 2080                 2085

Ile Leu  Ser Gln Phe Ser Val  Asn Val Thr Val Asp  Ala Gly Val
    2090                 2095                 2100

Ser Ala  Asp Pro Trp Leu Ile  Ala Tyr Asn Gly Met  Pro Asp Ser
    2105                 2110                 2115

Gln Lys  Ala Lys Ile Asp Lys  Ile Arg Asp Leu Val  Gly His Gln
    2120                 2125                 2130

Leu Glu  Trp Thr Gln Ser Leu  Asp Asp Asn Gly Glu  Leu Ile Thr
    2135                 2140                 2145

Asp Pro  Asn Lys Pro Ile Ile  Lys Val Asp Ser Asn  Gly Leu Met
    2150                 2155                 2160

Ser Tyr  Glu Asp Gly Thr Gly  Lys Lys Tyr Asp Phe  Phe Lys Tyr
    2165                 2170                 2175

Tyr Lys  Ser Pro Asn Asp Lys  Gln Gly Ser Phe Arg  Leu Ala His
    2180                 2185                 2190
```

-continued

Trp Asp Glu Val Asn Lys Glu Tyr Val Met Lys Ile Ile Lys Thr
2195 2200 2205

Gly Asn Ser Gly Gly Arg Asn Glu Tyr Arg Asp Phe Leu Val Arg
2210 2215 2220

Ala Tyr Lys Lys Asn Asp Val Ile Arg Lys Gln His Glu Lys Met
2225 2230 2235

Ile Ala Ser Gly Lys Ser Ile Thr Asn Pro Ile Ser Asn Trp Thr
2240 2245 2250

Lys Ser Asn Asn Ser Ser Asp Phe Trp Leu Ile Asp Lys Ser Asp
2255 2260 2265

Leu Asn Arg Gln Trp Val Asn Asp Tyr Phe Ile Gly Phe Gly Gly
2270 2275 2280

Val Leu Phe Asp Lys Ser Tyr Asp Glu Thr Tyr Thr Tyr Leu Ser
2285 2290 2295

Gly Thr Tyr Asn Asn Val Ser Ala Lys Ile Tyr Gly Tyr Arg Lys
2300 2305 2310

Pro Val Asp Phe Lys Asn Ala Lys Val Lys Leu Ile Asp Lys Ala
2315 2320 2325

Gly Asn Asn Leu Tyr Glu Val Leu Asp Lys Tyr Glu Val Lys Asn
2330 2335 2340

Asn Val Tyr Pro Leu Val Val Asn Asp Val Phe Ala Lys Lys His
2345 2350 2355

Lys Leu Gly Ile Asn Asp Leu Ile Asp Phe Lys Val Trp Asn Arg
2360 2365 2370

Val Asp Arg Tyr Lys Gln Lys Ile Ile Glu Lys Ile Tyr Ala Asn
2375 2380 2385

Asp Pro Val Lys Gln Ala Asp Leu Lys Asn Glu Tyr Asn Lys Lys
2390 2395 2400

Thr Asn Ala Lys Phe Gln Ile Val Gly Ile Asn Pro Thr Tyr Ile
2405 2410 2415

Asn Asp Glu Leu Ile Thr Thr His Lys Ala Ala Asn Leu Leu Ile
2420 2425 2430

Gly Met Thr Asp Ile Asp Asn Gly Phe Asn Gly Val Leu Thr Gln
2435 2440 2445

Asn Ala Asn Pro Val Gln Val Thr Glu Ser Ala Gly Leu Tyr Ser
2450 2455 2460

Val Ser Gly Tyr Trp Ala Gly Leu Asp Gly Phe Asp Val Ser Ser
2465 2470 2475

Leu Asp Asn Gly Thr Val Glu Lys Met Phe Asp Glu Ile Phe Gly
2480 2485 2490

Ser Pro Asp Lys Lys Gly Val Leu Glu Thr Gln His Gly Leu Thr
2495 2500 2505

Lys Asn Glu Ile Ala Lys Phe Leu Asp Ser Ser Ala Asn Lys Phe
2510 2515 2520

Ser Lys Ser Leu Tyr Glu Ser Ala Lys Ser Ser Ala Lys Leu His
2525 2530 2535

Ile Asp Glu Phe Ser Lys Ile Tyr Asn Asn Lys Leu Tyr Ile Ala
2540 2545 2550

Leu Ser Ser Ser Ile Asp Ser Lys Asp Ile Glu Val Gly Phe Val
2555 2560 2565

Leu Gln Val Gly Ser Thr Ile Glu Gln Ile Ser Ile Phe Ile Ile
2570 2575 2580

Val Ile Asn Phe Val Ile Ser Leu Ile Ile Leu Ile Ile Met Ser

-continued

```
    2585                2590                2595

Ser Ile  Ile Val Ser Glu Asn  Glu Arg Asn Ile Ala  Ile Trp Ser
    2600                2605                2610

Ile Leu  Gly Tyr Ser Gln Lys  Glu Lys Leu Met Met  Phe Phe Gly
    2615                2620                2625

Ala Phe  Ile Pro Phe Leu Val  Ser Ala Ile Val Ile  Ser Ile Pro
    2630                2635                2640

Ile Val  Ile Ala Leu Ile Ser  Val Phe Ser Gly Phe  Leu Leu Ser
    2645                2650                2655

Ser Ser  Ser Ile Ala Leu Leu  Leu Ser Leu Lys Trp  Trp His Val
    2660                2665                2670

Leu Ile  Thr Ser Gly Leu Met  Leu Thr Ile Phe Ala  Ile Thr Ser
    2675                2680                2685

Ile Ser  Val Trp Ile Thr Ile  Asn Lys Met Lys Pro  Val Asp Leu
    2690                2695                2700

Leu Lys  Gly Lys
    2705
```

MODIFIED LIVE VACCINE OF *MYCOPLASMA BOVIS*, METHODS OF PRODUCING MODIFIED LIVE *MYCOPLASMA BOVIS* VACCINES, COMBINATION VACCINES AND METHODS OF TREATMENT

RELATED APPLICATIONS

This application claims the priority benefit of U.S. Provisional Patent Application Ser. No. 61/172,543, filed on Apr. 24, 2009.

SEQUENCE LISTING

The instant application contains a Sequence Listing which has been submitted via EFS-Web and is hereby incorporated by reference in its entirety. Said ASCII copy, created on Apr. 20, 2010, is named 100118US.txt and is 103,855 bytes in size.

BACKGROUND OF THE INVENTION

*Mycoplasma bovis* (*M. bovis*) is considered to be one of the more pathogenic species of *Mycoplasma* and causes significant economic losses worldwide. Mycoplamsas cause severe clinical signs in cattle of all ages. *M. bovis* is the most frequent *Mycoplasma* pathogen found to cause pneumonia, mastitis, and arthritis in cattle and its etiological role has also been associated with otitis, keratoconjuctivitis, synovitis, and reproductive disorders in cows and bulls. In general, Mycoplasmas are difficult to treat since they lack a cell wall or membrane, which tends to make them resistant to several classes of commonly used broad-spectrum antibiotic treatments. Mycoplasmas differ from viruses in that Mycoplasmas are larger than most viruses and damage tissue cells by attaching to the surface of cells and destroying them, rather than by entering the cells. Animals infected with *M. bovis* have depressed immune responses and may exhibit signs of *M. bovis* infection such as fever, depression, anorexia, labored breathing, nasal and ocular discharge, coughing, sneezing, gasping, grunting, lameness and swollen joints, mastitis, middle ear infections, abortions, recumbence and death. The organism persists in unsanitary, warm, moist environments. Mycoplasmas may survive in milk, and even seem to thrive in the presence of large numbers of leukocytes, which are produced in response to the infection.

U.S. Pat. No. 6,548,069 discloses a vaccine composition that incorporates a whole cell inactivated bacterin containing at least two killed *M. bovis* strains and that an isolate may rapidly alter its antigens in culture. The patent teaches that high passage strains of greater than about 50 passages may lose infectivity and elicit a poorer immune response when used in a bacterin. It teaches use of a *Mycoplasma* strain which has been passed no more than about ten times or less before mass scale production because the antigens are believed to retain their natural state and thus will elicit a protective immune response against the infectious microorganism.

Killed *M. bovis* is not as effective or efficient as desired in lessening the severity of clinical symptoms associated with a *Mycoplasma bovis* infection. Even passage at a low level does not produce a *Mycoplasma* vaccine with high efficacy such that clinical symptoms are greatly reduced in animals when compared to animals not receiving such a vaccine. The few low passage, inactivated, *M. bovis* vaccines that are available do not show a large reduction in the severity of clinical symptoms in animals when compared to animals not receiving such vaccine.

The nature of the market requires that farmers be able to effectively immunize their animals for a wide variety of conditions in an efficient way. Other conditions that would be suitable for efficient immunization include, but are not limited to, Bovine viral diarrhea virus (BVDV), Parainfluenza-3 virus (PI-3), Bovine Respiratory Syncytial Virus (BRSV), Bovine Herpesvirus (BHV-1), Bovine rotavirus, Breda virus, a calici-like virus, Adenovirus, Astrovirus and Parvovirus, *Mannheimia haemolytica* (formerly *Pasteurella haemolytica*), *Pasteurella multocida, Actinomyces* (*Arcanobacterium*) *pyogenes, Haemophilus somnus* (reclassified as *Histophilus somni*), Chlamydiae, Bovine genital campylobacteriosis, Leptospirosis, Brucellosis, *Clostridia, Escherichia coli, Cryptosporidium parvum, Mycobacterium avium paratuberculosis, Salmonella, Mycobacterium avium paratuberculosis*, Cryptosporidiosis, mastitis, Dermatomycoses, lower respiratory tract infections, Trichomoniases, *Neospora Canum*, Babesiosis and the like.

There remains a need for an immunogenic composition effective for eliciting an immunological response against *M. bovis* for lessening the severity of or reducing the incidence of signs of *M. bovis* infection, and for reducing or eliminating the incidence of signs of *M. bovis* infection.

SUMMARY OF THE INVENTION

The present invention provides an immunogenic composition or vaccine which uses high passage attenuated *M. bovis* strains, such that signs of *M. bovis* infection and/or the *M. bovis* infection itself and/or incidence or severity, are reduced in animals receiving the immunogenic composition or vaccine as compared to those animals with infection by wild-type *M. bovis* strains. The immunological composition of the present invention provides rapid onset of protection and long-lasting protection to an animal in need thereof.

The invention provides for attenuated and avirulent strains or isolates of *M. bovis* which have been passaged at least 110 times that provoke or elicit an immune response when administered to an animal. According to another aspect, the present invention also relates to attenuated *M. bovis* bacteria having the same characteristics as the *M. bovis* bacteria strain deposited with the ATCC under accession numbers PTA-9666 and PTA-9667.

An *M. bovis* strain of the present invention, attenuated through multiple passage or serial attenuation as described above, may be used as a medicine, preferably as a veterinary medicine. Further, the attenuated *M. bovis* strains of the present invention may be used for the preparation of veterinary compositions, for the prophylaxis or treatment of infections caused by *M. bovis* in animals susceptible to infection by *M. bovis*.

Such an immunological composition would be suitable as either a one dose or two dose or multi-dose (initial dose followed by booster(s)) immunization regimen, an immunological composition suitable and convenient for administration by several routes, and an immunological composition that is compatible with other immunogens and immunological compositions for preparation of combination vaccines.

In another embodiment of the present invention, the *M. bovis* strains of the present invention may be combined with other medicaments, therapies or vaccines.

The present invention also provides for a method of making the immunogenic composition of the present invention. The method comprises obtaining a virulent strain of *M. bovis* and passaging said strain at least 110 times, such that it becomes attenuated and avirulent. The high passage strain may then be mixed with an additional components including but not limited to, pharmaceutically acceptable carriers, diluents, other medicaments, therapeutic compositions or vaccines, and combinations thereof.

The present invention also provides for a method of treatment or prophylaxis of animals having an *M. Bovis* infection to reduce signs of *M. bovis* infection, reduce the severity of or incidence of clinical signs of *M. bovis* infection, reduce the mortality of animals from *M. bovis* infection, and combinations thereof.

DETAILED DESCRIPTION OF THE INVENTION

Definitions

Figure 1:
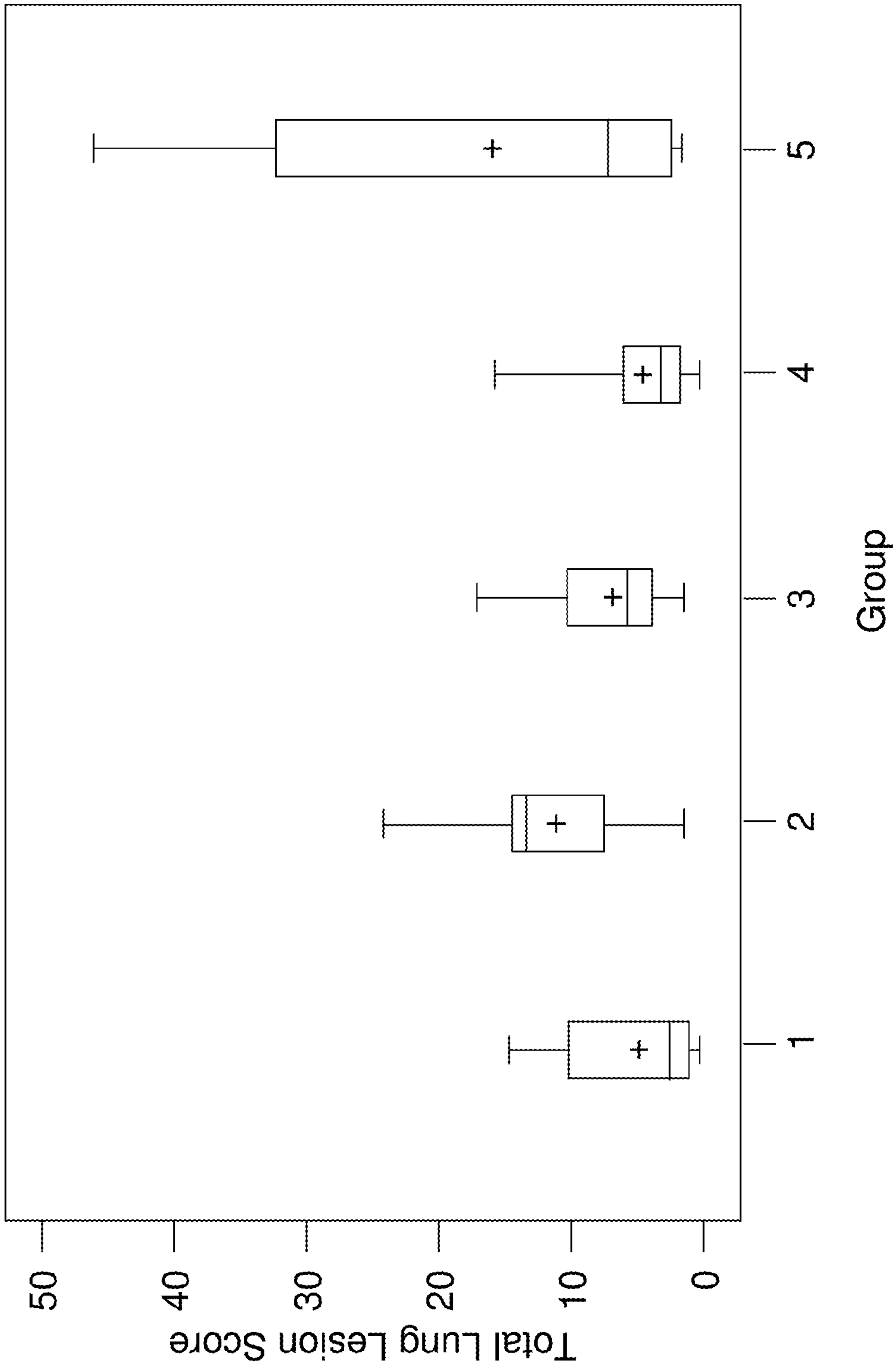
FIG. 1 is a graph illustrating lung lesion scores for animals receiving an *M. bovis* isolate passaged 135 times in accordance with the present invention isolate.

For purposes of the present invention, the terms "isolate" and "strain" are used interchangeably and that differences between individual strains or isolates may be detected using DNA fingerprinting (i.e. different strains or isolates will have differing fingerprints). For purposes of the present invention, the terms "vaccine" and "composition" are used interchangeably.

The following terms and expressions are used herein:

"Attenuation" means reducing the virulence of a pathogen. In the present invention "attenuation" is synonymous with "avirulent". In the present invention, an attenuated bacterium is one in which the virulence has been reduced so that it does not cause clinical signs of a *M. bovis* infection but is capable of inducing an immune response in the target mammal, but may also mean that the clinical signs are reduced in incidence or severity in animals infected with the attenuated *M. bovis* in comparison with a "control group" of animals infected with non-attenuated *M. bovis* and not receiving the attenuated bacterium. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent *M. bovis* strain is one that suitable for incorporation into an immunogenic composition comprising a modified live *M. bovis* bacterium.

"Diluents" may include water, saline, dextrose, ethanol, glycerol, and the like. Isotonic agents may include sodium chloride, dextrose, mannitol, sorbitol, and lactose, among others. Stabilizers include albumin and alkali salts of ethylendiamintetracetic acid, among others.

An "effective amount" for purposes of the present invention, means an amount of an immunogenic composition capable of inducing an immune response that reduces the incidence of or lessens the severity of *M. bovis* infection in an animal. Particularly, an effective amount refers to colony forming units (CFU) per dose. The preferred immunogenic composition or vaccine of the present invention has at least 1.0 E7 CFU of the live bacteria of the attenuated, avirulent *M. bovis* bacteria per dose, more preferably 8.4 E7 CFU or 9.4 E7 CFU of the live bacteria of the attenuated, avirulent *M. bovis* bacteria per dose. An example (but not meant to be limited to such example) of an effective amount would be an *M. bovis* vaccine administered via a simultaneous intranasal and subcutaneous route administered 2 times with a 2 week interval at a high dose level (1E9 CFU).

"High passage strain" as well as the term "passaged at least 110 times" for purposes of the present invention, refers to an *M. bovis* strain that has been passaged more than 110 times, more preferably, more than 115 times, more preferably, more than 120 times, even more preferably, more than 125, even more preferably, more than 130 times, more preferably, more than 133 times, even more preferably, more than 135 times, and still more preferably between 135 and 145 times, specifically more preferably more than 140 times, and more preferably more than 145 times, and further more preferably more than 150 times.

The term "having the characteristics as the *M. bovis* bacteria strain deposited with the ATCC under accession numbers PTA-9666 and PTA-9667" means that such a bacteria strain is attenuated, and is capable to reduce the mortality and euthanization rate in a group of animals of at least 83% as compared to a non-vaccinated control group of animals. Furthermore, the term also means that such a bacteria strain is attenuated, and is cable to reduce the mortality and euthanization rate in a group of animals at least 56% when compared to a non-vaccinated control group of animals after the administration of a single dose of said vaccine. Additionally, the term also means that such a bacteria strain is attenuated, and is cable to reduce the mortality and euthanization rate in a group of animals at least 65% when compared to a non-vaccinated control group of animals after the administration of a single dose of said vaccine.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "Immunogenic testing" means infecting cattle with the passaged *M. bovis* bacteria and monitoring the development of the humoral antibody response against *M. bovis* in the infected cattle.

The term "Improved efficacy such that clinical signs associated with *M. bovis* infection and/or the *M. bovis* infection itself were reduced in comparison to currently available vaccines when vaccinates are exposed to *M. bovis* or suffer infection by wild-type *M. bovis* strains" refers to a reduction in either the incidence of or severity of clinical signs of *M. bovis* infection when comparing vaccines made from strains passaged as taught by the present invention with *M. bovis* vaccines that were available prior to this invention. In this context, animals not vaccinated, or vaccinated with *M. bovis* vaccines available prior to the present invention will have clinical signs of *M. bovis* infection that are at least 30%, and possibly up to more preferably at least 40%, still more preferably at least 50%, even more preferably at least 60%, still more preferably at least 70%, even more preferably at least 75%, still more preferably at least 80%, even more preferably at least 85%, still more preferably at least 90%, and most preferably at least 95% more severe or prevalent than in animals receiving an administration of an *M. bovis* immunogenic composition in accordance with the present invention.

The term "in need of such administration" or "in need of such administration treatment", means that the administration or treatment is associated with the boosting or improvement in health or any other positive medicinal effect on health of the animals which receive the immunogenic composition in accordance with the present invention.

The term "Long-lasting protection" refers to improved efficacy that persists for at least 3 weeks, but more preferably at least 6 months, still more preferably at least 1 year, even more preferably at least 2 years for beef animals, and at least 6 months, more preferably at least 1 year, still more preferably at least 2 years, still more preferably at least 3 years, and even more preferably at least 4 years for dairy animals. For both dairy animals and beef animals, it is most preferred that the long lasting protection shall persist until the average age at which beef animals are marketed for meat and the age at which dairy animals conclude their productive life of milking.

The term "Lung Pathology Assessment" refers to observation of the lungs after necropsy, including, but not limited to, assessment of consolidation, lesions, and nodular formations as well as assessment of the thoracic cavity including pleuritis and fluid accumulation.

The term "Mortality" refers to death caused by *M. bovis* infection. This includes the situation where the infection is so severe that an animal is euthanized to prevent suffering and provide a humane ending to their life.

The term "Signs of *M. bovis* infection" refers to the manifestations of infection or disease caused by *M. bovis* including both the clinical symptom(s) and pathology typically experienced by cattle infected with wild type *M. bovis*. These manifestations of infection or disease may take many forms including, but not limited to, fever, depression, anorexia, labored breathing, nasal and ocular discharge, coughing, sneezing, gasping, grunting, lameness and swollen joints, middle ear infections, discharge from inflammation of the inner ear, abortions and other reproductive disorders, recumbence, respiratory infection, head tilt, ataxia, arthritis, mastitis, otitis, keratoconjunctivitis, synovitis, pleuritis, lung lesions, lung consolidation and nodular formation in the lungs, increased synovial fluid, thickened joint capsules, and death.

The term a "veterinary acceptable carrier" "pharmaceutically acceptable carrier" or "carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

The present invention provides an immunogenic composition or vaccine which overcomes the problems inherent in previous vaccines and provides a safe, efficacious vaccine utilizing high passage attenuated *M. bovis* strains, such that signs of *M. bovis* infection and/or the *M. bovis* infection itself and/or incidence or severity, are reduced in animals receiving the immunogenic composition or vaccine comparison with infection by wild-type *M. bovis* strains. Additionally, the lethal effect of *M. bovis* is reduced when the immunogenic composition of the present invention is administered to an animal (e.g., calves given a vaccine in accordance with the present invention are at a lower risk of developing signs of *M. bovis* infection, as well as death associated with *M. bovis* infection, and any clinical signs that result would be less severe or prevalent than in animals not receiving any vaccine, but were infected with *M. bovis* or receiving a vaccine not in accordance with the present invention).

Additionally, herds would experience a smaller number of infected and deceased animals in a herd when animals are administered the vaccine in accordance with the present invention as compared to non-vaccinated but infected animals, and preferably even as compared to animals vaccinated with conventionally available vaccine(s). The high passage, attenuated strains of the present invention provide added efficacy when compared to other vaccines currently on the market.

The present invention provides for attenuated and avirulent strains or isolates of *M. bovis* which have been passaged at least 110 times that provoke or elicit an immune response when administered to an animal. Advantageously, such attenuated and avirulent strains or isolates of *M. bovis* which have been passaged at least 110 times provokes or elicits an immune response that protects the animals receiving the immunogenic composition of the present invention and reduces the risk of the animals dying or having to be euthanized as a result of *M. bovis* infection. The immunogenic composition also has the benefit of reducing the number of animals in a herd experiencing death or euthanasia as a result of *M. bovis* infection. Further, the composition has been shown to lessen the incidence and severity of clinical signs of *M. bovis* infections in individual animals and herds.

In one embodiment, an immunogenic composition is disclosed which comprises one or more high passage *M. bovis* strain(s) which have been passaged at least 110 times and a pharmaceutically acceptable carrier. The immunogenic composition of the present invention elicits an immune or immunogenic response against *M. bovis* infection in animals, and preferably cattle. Generation of the immunogenic response has the effect of lessening the incidence and severity of clinical signs of *M. bovis* infection as well as reducing mortality and euthanization as a result of *M. bovis* infection.

Another embodiment provides for a method of making the immunogenic composition of the present invention. The method comprises obtaining a virulent strain of *M. bovis* and passaging said strain at least 110 times, such that it becomes attenuated and avirulent. The high passage strain may optionally then be mixed with additional components including but not limited to, adjuvants, pharmaceutically acceptable carriers, diluents, and combinations thereof. The method generally comprises (a) passaging *M. bovis* bacteria more than 110 times to produce a cultured *M. bovis* bacteria; (b) obtaining the cultured *M. bovis* bacteria; and (c) propagating the non-pathogenic, but immunogenic *M. bovis* bacteria to obtain the attenuated *M. bovis* bacteria.

In preferred forms of this method, an additional step of testing the cultured *M. bovis* bacteria obtained under step (b) for its pathogenicity and immunogenicity. Preferably, this step is done prior to step (c). Pathogenicity testing comprises infecting cattle with the passaged *M. bovis* bacteria and monitoring the infected cattle for developing clinical symptoms of an *M. bovis* infection.

The present invention also provides for a method of reducing the incidence of death or euthanasia resulting from *M. bovis* infection in an individual cow or within a herd of cattle. The method comprises administration of a high passage strain of *M. bovis*, passaged at least 110 times, to a bovine. The immunogenic composition of the present invention has been shown to reduce mortality in cattle and in herds when compared to those animals not receiving a vaccine as well as compared to those strains passaged less than 110 times. Preferably, mortality in cattle and in herds is reduced by at least 10%, more preferably, mortality is reduced by at least 20%, even more preferably, mortality is reduced by at least 25%, more preferably, mortality is reduced by at least 30%, even more preferably, mortality is reduced by at least 40%, still more preferably, mortality is reduced by at least 50%, even more preferably, mortality is reduced by at least 56%, still more preferably mortality is reduced by at least 60%, even more preferably, mortality is reduced by at least 70%, still more preferably, mortality is reduced by at least 75%, even more preferably, mortality is reduced by at least 80%, still more preferably, mortality is reduced by at least 83%, and, most preferably, mortality is reduced by at least 90% as compared to those animals not receiving a vaccine.

Additionally, mortality in cattle and in herds is reduced by at least 10%, more preferably, mortality is reduced by at least 20%, even more preferably, mortality is reduced by at least 25%, more preferably, mortality is reduced by at least 30%, even more preferably, mortality is reduced by at least 40%, still more preferably, mortality is reduced by at least 48% as compared to those strains passaged less than 110 times as compared to other *M. bovis* stains, including for example, *M. bovis* bacteria strains deposited with the ATCC under accession numbers PTA-8694; PTA 8695; or PTA 8696.

Another embodiment includes a method for the treatment or prophylaxis of infections caused by *M. bovis*. The method comprises administering an effective amount of the immunogenic composition of the present invention to an animal, wherein said treatment or prophylaxis is selected from the group consisting of reducing signs of *M. bovis* infection, reducing the severity of or incidence of clinical signs of *M. bovis* infection, reducing the mortality of animals from *M. bovis* infection, and combinations thereof.

A further embodiment includes a method of reducing the incidence and/or severity of clinical symptoms of *M. bovis* infection. The method generally comprises administration of a high passage strain of *M. bovis*, passaged at least 110 times, to animals, preferably cattle. More particularly, the method may be used to reduce lung consolidation due to *M. bovis* infection. The effectiveness of the administration of a high passage strain of *M. bovis* to an animal in need thereof may be verified in a number of conventional ways, including lung pathology assessment. Preferably, lung pathology assessment, specifically the percentage of lung consolidation attributed to lesions due to *M. bovis* as customarily scored for various species may be made post-necropsy. Still more preferably, such lung pathology will be reduced when compared to the non-vaccinated group, by at least 33%, more preferably at least 50%, even more preferably at least 70%, still more preferably at least 80%, even more preferably at least 90%, and most preferably by at least 95%.

A surprising result of the present invention found that further passaging of the *M. bovis* strain led to increased efficacy of the vaccine. When results of efficacy studies for previous high passage strains, i.e. those passaged less than 110 times (e.g., *M. bovis* bacteria strains deposited with the ATCC under accession numbers PTA-8694; PTA 8695 or PTA 8696), were compared to the results of those studies using the higher passage strain of the present invention, it was surprisingly found that there was a reduction in mortality or euthanasia for humanitarian reasons for cattle resulting from *M. bovis* infection using the strain of the present invention.

It was an additionally surprising result that administration of one dose of the higher passaged strain of the present invention was as or more efficient and efficacious as the two dose administration of the previous high passage strain, passaged less than 110 times, in reducing of the number of cattle experiencing death or euthanasia as a result of *M. bovis* infection. While a reduction in mortality of about 56%, as compared to a non-vaccinated animals, was provided by a single administration of the attenuated *M. bovis* strains of the present invention passaged more than 110 times, two administrations of attenuated *M. bovis* strains passaged not more 106 times were needed to obtain the same reduction in mortality.

In a preferred embodiment, the high passage strain of *M. bovis* is passaged at least 110 times in vitro in cell culture, more preferably, between 110 times and 200 times, even more preferably, between about 110 and 180 times, still more preferably, at least 115 times, even more preferably at least 120 times, still more preferably, between 120 and 170 times, even more preferably at least 125 times, still more preferably between 125 and 160 times, even more preferably, at least 130 times, still more preferably, between 130 and 150 times, even more preferably at least 131 times, more preferably, at least 132 times, even more preferably, at least 133 times, more preferably, at least 134 times, and even more preferably, at least 135 times, and most preferably between 135 and 145 times.

The strains of *M. bovis* useful in the vaccine or immunogenic composition may be any strain or isolate of *M. bovis* having the same properties like inventive strains as described herein. Representative strains include those deposited with the ATCC in Manassas, Va. on Dec. 18, 2008, under the terms of the Budapest Treaty and designated as ATCC deposit numbers PTA-9666 and PTA-9667. These strains are pathogenic prior to passaging, but after passaging the strain as described above, and particularly after passaging more than 110 times, the resultant passaged strains were attenuated, avirulent, and produced an immune response in an animal receiving an administration of the immunogenic composition of the strain. In particular, these strains led to increased efficacy and show a reduced mortality in cattle and in herds when used as a modified live vaccine. Advantageously, the vaccine or immunogenic composition of the present invention utilizing such deposited strains exhibited effective cross-protection against *M. bovis* strains other than the strain passaged to attenuation and then used as an antigenic component.

Combination Compositions

In another embodiment of the present invention, the *M. bovis* strains of the present invention may be combined with other medicaments, therapies or vaccines. Conditions that would be suitable for efficient immunization include, but are not limited to, Bovine viral diarrhea virus (BVDV), Parainfluenza-3 virus (PI-3), Bovine Respiratory Syncytial Virus (BRSV), Bovine Herpesvirus (BHV-1), Bovine rotavirus, Breda virus, a calici-like virus, Adenovirus, Astrovirus and Parvovirus, *Mannheimia haemolytica* (formerly *Pasteurella haemolytica*), *Pasteurella multocida, Actinomyces* (*Arcanobacterium*) *pyogenes, Haemophilus somnus* (reclassified as *Histophilus somni*), Chlamydiae, Bovine genital campylobacteriosis, Leptospirosis, Brucellosis, *Clostridia, Escherichia coli, Cryptosporidium parvum, Mycobacterium avium paratuberculosis, Salmonella, Mycobacterium avium paratuberculosis*, Cryptosporidiosis, mastitis, Dermatomycoses, lower respiratory tract infections, Trichomoniases, *Neospora Canum*, Babesiosis and the like.

Bovine viral diarrhea virus (BVDV) type 1 (BVDV-1) and type 2 (BVDV-2) cause bovine viral diarrhea (BVD) and mucosal disease (MD) in cattle (Baker, 1987; Moennig and Plagemann, 1992; Thiel et al., 1996, hereby entirely incorporated by reference). The division of BVDV into 2 serotypes is based on significant differences at the level of genomic sequences (summarized in Heinz et al., 2000, hereby entirely incorporated by reference) which are also obvious from limited cross neutralizing antibody reactions (Ridpath et al. 1994, entirely incorporated by reference). Inactivation of the RNase activity residing within the $E^{rns}$ results in an attenuated apathogenic BVDV which may be used as a modified live vaccine (WO 99/64604, hereby entirely incorporated by reference). The international patent application WO2005/111201 (hereby entirely incorporated by reference) provides a further generation of an attenuated BVDV suitable for MLV vaccines, which comprises a multiple modified BVDV having at least one mutation in the coding sequence for glycoprotein $E^{rns}$ and at least another mutation in the coding sequence for $N^{pro}$, wherein said mutation in the coding sequence for glycoprotein $E^{rns}$ leads to inactivation of RNase activity residing in $E^{rns}$ and/or said mutation in the coding sequence for $N^{pro}$ leads to inactivation of said $N^{pro}$. Furthermore, various conventional attenuated BVDV viruses are known in the art, which are also suitable candidates for vaccine development.

Parainfluenza-3 virus (PI-3) is an RNA virus classified in the paramyxovirus family. Infections caused by PI-3 are common in cattle. Although PI-3 is capable of causing disease, it is usually associated with mild to subclinical infections. The most important role of PI-3 is to serve as an initiator that may lead to the development of secondary bacterial pneumonia. Clinical signs include pyrexia, cough, serous nasal and lacrimal discharge, increased respiratory rate, and increased breath sounds. The severity of clinical signs worsen with the onset of bacterial pneumonia. Fatalities from uncomplicated PI-3 pneumonia are rare. Lesions include cranioventral lung consolidation, bronchiolitis, and alveolitis with marked congestion and haemorrhage. Inclusion bodies may be identified. Most fatal cases will also have a concurrent bacterial bronchopneumonia.

Bovine Respiratory Syncytial Virus (BRSV) is an RNA virus classified as a pneumovirus in the paramyxovirus family. In addition to cattle, sheep and goats may also be infected by respiratory syncytial viruses. This virus was named for its characteristic cytopathic effect—the formation of syncytial cells. BRSV is distributed worldwide, and the virus is indigenous in the cattle population. BRSV infections associated with respiratory disease occur predominantly in young beef and dairy cattle. Passively derived immunity does not appear to prevent BRSV infections but will reduce the severity of disease. Initial exposures to the virus are associated with severe respiratory disease; subsequent exposures result in mild to subclinical disease. BRSV appears to be an important virus in the bovine respiratory disease complex because of its frequency of occurrence, predilection for the lower respiratory tract, and its ability to predispose the respiratory tract to secondary bacterial infection. In outbreaks, morbidity tends to be high, and case fatality may be 0-20%. Signs include increased rectal temperature 40-42° C., depression, decreased feed intake, increased respiratory rate, cough, and nasal and lacrimal discharge. Generally, respiratory signs predominate. Dyspnea may become pronounced in the later stages of the disease. Subcutaneous emphysema is sometimes reported. Secondary bacterial pneumonia is a frequent occurrence. A biphasic disease pattern has been described but is not consistent. Gross lesions include a diffuse interstitial pneumonia with subpleural and interstitial emphysema along with interstitial edema. These lesions are similar to and must be differentiated from other causes of interstitial pneumonia. Histologic examination reveals syncytial cells in bronchiolar epithelium and lung parenchyma, intracytoplasmic inclusion bodies, proliferation and/or degeneration of bronchiolar epithelium, alveolar epithelialization, edema, and hyaline membrane formation.

Bovine Herpesvirus (BHV-1) is associated with several diseases and symptoms in cattle: Infectious bovine rhinotracheitis (IBR), infectious pustular vulvovaginitis (IPV), balanoposthitis, conjunctivitis, abortion, encephalomyelitis, and mastitis. Only a single serotype of BHV-1 is recognized; however, three subtypes of BHV-1 have been described on the basis of endonuclease cleavage patterns of viral DNA. These types are referred to as BHV-1.1 (respiratory subtype), BHV-1.2 (genital subtype), and BHV-1.3 (encephalitic subtype). Recently, BHV-1.3 has been reclassified as a distinct herpesvirus designated BHV-5. BHV-1 infections are widespread in the cattle population. In feedlot cattle, the respiratory form is most common. The viral infection alone is not life-threatening but predisposes cattle to secondary bacterial pneumonia, which may result in death. In breeding cattle, abortion or genital infections are more common. Genital infections may occur in bulls (infectious pustular balanoposthitis) and cows (IPV) within 1-3 days of mating or close contact with an infected animal. Transmission may occur in the absence of visible lesions and through artificial insemination with semen from subclinically infected bulls. Cattle with latent BHV-1 infections generally show no clinical signs when the virus is reactivated, but they do serve as a source of infection for other susceptible animals and thus perpetuate the disease. The incubation period for the respiratory and genital forms is 2-6 days. In the respiratory form, clinical signs range from mild to severe, depending on the presence of secondary bacterial pneumonia. Clinical signs include pyrexia, anorexia, coughing, excessive salivation, nasal discharge that progresses from serous to mucopurulent, conjunctivitis with lacrimal discharge, inflamed nares (hence the common name "red nose"), and dyspnea if the larynx becomes occluded with purulent material. Pustules may develop on the nasal mucosa and later form diphtheritic plaques. Conjunctivitis with corneal opacity may develop as the only manifestation of BHV-1 infection. In the absence of bacterial pneumonia, recovery generally occurs 4-5 days after the onset of clinical signs. Abortions may occur concurrently with respiratory disease but may also occur up to 100 days after infection. Abortions may occur regardless of the severity of disease in the dam. Abortions generally occur during the second half of pregnancy, but early embryonic death may also occur. The first signs of genital infections in cows are frequent urination, elevation of the tailhead, and a mild vaginal discharge. The vulva is swollen, and small papules, then erosions and ulcers, are present on the mucosal surface. If secondary bacterial infections do not occur, animals recover in 10-14 days. If bacterial infection occurs, there may be inflammation of the uterus and transient infertility, with purulent vaginal discharge for several weeks. In bulls, similar lesions occur on the penis and prepuce. BHV-1 infection may be severe in young calves and cause a generalized disease. Pyrexia, ocular and nasal discharges, respiratory distress, diarrhea, incoordination, and eventually convulsions and death may occur in a short period after generalized viral infection. IBR is rarely fatal in cattle unless complicated by bacterial pneumonia. In uncomplicated IBR infections, most lesions are restricted to the upper respiratory tract and trachea. Petechial to ecchymotic hemorrhages may be found in the mucous membranes of the nasal cavity and the paranasal sinuses. Focal areas of necrosis develop in the nose, pharynx, larynx, and trachea. The lesions may coalesce to form plaques. The sinuses are often filled with a serous or serofibrinous exudate. As the disease progresses, the pharynx becomes covered with a serofibrinous exudate, and blood-tinged fluid may be found in the trachea. The pharyngeal and pulmonary lymph nodes may be acutely swollen and hemorrhagic. The tracheitis may extend into the bronchi and bronchioles; when this occurs, epithelium is sloughed in the airways. The viral lesions are often masked by secondary bacterial infections. In young animals with generalized BHV-1 infection, erosions and ulcers overlaid with debris may be found in the nose, esophagus, and forestomachs. In addition, white foci may be found in the liver, kidney, spleen, and lymph nodes. Aborted fetuses may have pale, focal, necrotic lesions in all tissues, but which are especially visible in the liver.

A number of other Bovine Respiratory Viruses have been identified as being involved in BRD. Bovine herpesvirus-4 has been implicated in several diseases, including BRD. Bovine adenovirus has been associated with a wide spectrum of diseases, with bovine adenovirus type 3 being the serotype most often associated with BRD. Two serotypes of bovine rhinovirus have been recognized to cause respiratory tract infections in cattle. Other viruses reported to be associated with BRD include bovine reovirus, enterovirus, and coronavirus. These viruses have a role similar to the other viruses previously discussed in that, in combination with other stressors, they may serve as initiators of bacterial pneumonia. Bovine coronavirus is also commonly associated with diarrhea in calves. It replicates in the epithelium of the upper respiratory tract and in the enterocytes of the intestine, where it produces similar lesions to rotavirus but also infects the epithelial cells of the large intestine to produce atrophy of the colonic ridges. Vaccines are not available for prevention of these viral respiratory diseases.

Bovine rotavirus is the most common viral cause of diarrhea in calves. Group A and B rotavirus are involved, but group A is the most prevalent and clinically important and contains several serotypes of differing virulence. Rotavirus replicates in the mature absorptive and enzyme-producing enterocytes on the villi of the small intestine, leading to rupture and sloughing of the enterocytes with release of virus to infect adjacent cells. Rotavirus does not infect the immature cells of the crypts. With virulent strains of rotavirus, the loss of enterocytes exceeds the ability of the intestinal crypts to replace them; hence, villous height is reduced, with a consequent decrease in intestinal absorptive surface area and intestinal digestive enzyme activity.

Other viruses, including Breda virus, a calici-like virus, Adenovirus, Astrovirus and Parvovirus, have been demonstrated in the feces of calves with diarrhea and may produce diarrhea in calves experimentally. However, these agents may also be demonstrated in the feces of healthy calves. The importance of these agents in the syndrome of neonatal diarrhea has yet to be determined. *Mannheimia haemolytica* (formerly *Pasteurella haemolytica*) biotype A, serotype 1 is the bacterium most frequently isolated from the lungs of cattle with BRD. Although less frequently cultured than *M. haemolytica, Pasteurella multocida* is also an important cause of bacterial pneumonia. When pulmonary abscessation occurs, generally in association with chronic pneumonia, *Actinomyces* (*Arcanobacterium*) *pyogenes* is frequently isolated. Under normal conditions, *M. haemolytica* generally remains confined to the upper respiratory tract, in particular the tonsillar crypts, and is difficult to culture from healthy cattle. After stress or viral infection, the replication rate of *M. haemolytica* in the upper respiratory tract increases rapidly, as does the likelihood of culturing the bacterium. The increased bacterial growth rate and colonization of the lungs may be due to suppression of the host's defense mechanism related to environmental stressors or viral infections. It is during this log phase of growth that virulence factors are elaborated by *M. haemolytica*, such as an exotoxin that has been referred to as leukotoxin. The interaction between the virulence factors of the bacteria and host defenses results in tissue damage and development of pneumonia. Clinical signs of bacterial pneumonia are often preceded by signs of viral infection of the respiratory tract. With the onset of bacterial pneumonia, the severity of clinical signs increases and are characterized by depression and toxemia. There will be pyrexia (40-41° C.); serous to mucopurulent nasal discharge; moist cough; and a rapid, shallow respiratory rate. Auscultation of the cranioventral lung field reveals increased bronchial sounds, crackles, and wheezes. In severe cases, pleurisy may develop, which is characterized by an irregular breathing pattern and grunting on expiration. The animal will become unthrifty in appearance if the pneumonia becomes chronic, which is usually associated with the formation of pulmonary abscesses. *M. haemolytica* causes a severe, acute fibrinous pneumonia or fibrinonecrotic pneumonia. The pneumonia has a bronchopneumonic pattern. Grossly, there is extensive reddish black to greyish brown cranioventral regions of consolidation with gelatinous thickening of interlobular septa and fibrinous pleuritis. There are extensive thromboses, foci of lung necrosis, and limited evidence of bronchitis and bronchiolitis. *P. multocida* is associated with a less fulminating fibrinous to fibrinopurulent bronchopneumonia. In contrast to *M. haemolytica, P. multocida* is associated with only small amounts of fibrin exudation, some thromboses, limited lung necrosis, and suppurative bronchitis and bronchiolitis.

*Haemophilus somnus* (recently reclassified as *Histophilus somni*) is being increasingly recognized as an important pathogen in BRD; these bacteria are normal inhabitants of the nasopharynx of cattle. *H. somnus* infection of the lungs results in purulent bronchopneumonia that may be followed by septicemia and infection of multiple organs. Occasionally, *H. somnus* is associated with extensive pleuritis. *H. somnus* may cause an acute, usually fatal, septicemic disease that may involve the nervous, musculoskeletal, circulatory, and respiratory systems, either singly or together. The reproductive system is often affected but usually without the other systems being clinically involved. The disease may be characterized by fever, severe depression, ataxia, weakness, blindness, coma, and death within several hours to several days. It occurs sporadically in individual beef and dairy cattle and is found nearly worldwide. *H. somnus* is a gram-negative, nonmotile, nonsporeforming, pleomorphic coccobacillus that requires an enriched medium and a microaerophilic atmosphere for culture. It appears to be identical to *Histophilus ovis* and *Haemophilus agni*, etiologic agents of ovine septicemia, mastitis, and epididymitis; however, transmission of *H. somnus* between sheep and cattle has not been demonstrated. Pathogenic and nonpathogenic strains have been differentiated by intracisternal inoculation of young calves with organisms from various sources. Pathogenic and nonpathogenic strains of *H. somnus* are carried in the sheath and prepuce of males, the vagina of female cattle, and in the nasal passages of both sexes. The organism may colonize the respiratory tract, presumably after inhalation, and is frequently found in urine. Prevalence of the organism in cattle is probably high because high titers of specific antibodies are found in a large proportion of tested cattle. Several disease syndromes caused by *H. somnus* have been recognized, including thrombomeningoencephalitis, fibrinopurulent bronchopneumonia, fibrinous pleuritis, and polyarthritis. Myocardial and skeletal muscle necroses occur. Suppurative vaginitis, cervicitis, and endometritis have been documented in cows infected experimentally and naturally after breeding, and the organism is a cause of sporadic abortion. Strains of *H. somnus* that cause disease adhere to the endothelium of vessels, resulting in contraction, exposure of collagen, platelet adhesion, and thrombosis. TME results when this occurs in the brain and associated membranes, after invasion of the organism into the bloodstream of susceptible cattle. Strains may adhere to endothelium in vessels of the pleura, myocardium, synovium, or a variety of other tissues and produce inflammation in those sites (e.g., infections of the larynx and middle ear have been recorded). The susceptibility of individual animals and variations in the preference of strains of the organism for vessels in different tissues may be important in the development of the form of disease, but the mechanisms involved are incompletely understood. Reproductive problems may not necessarily be preceded by bacteremia, but the pathogenesis is poorly defined. A fever as high as 42° C. is often the first sign of disease; however, this usually falls to normal or subnormal within hours. Other findings are determined by the system(s) involved and may include rapid respiration, stiffness, knuckling at the fetlocks, severe depression, ataxia, paralysis, and opisthotonos, followed by coma and death within several hours. Affected animals may be blind, and retinal hemorrhages with grey foci of retinal necrosis are sometimes seen. Signs such as hypersensitivity, convulsions, excitement, nystagmus, and circling occur inconsistently and may be related to the regions of the CNS affected in the course of disease development. Occasionally, animals are found dead, indicating a rapidly fatal course. A marked change in the total and differential WBC count is common; leukopenia and neutropenia occur in severe, usually acute, fatal disease, while neutrophilia may be present in less severe disease. In TME, the total cell count of the CSF is markedly increased, and neutrophils predominate. During septicemia, the organism may be recovered from blood, synovial fluid, CSF, brain, kidneys, urine, and a variety of other organs. The lesions are characterized by vascular thrombosis and infarction of the surrounding tissue. Randomly distributed red to brown foci of necrosis with hemorrhage on the surface and cut sections of the brain and spinal cord, retina, skeletal muscle, myocardium, kidney, intestine, and spleen are characteristic. A fibrinopurulent meningitis with cloudy CSF may sometimes be seen on the surface of the brain and spinal cord, and a polyserositis, especially of joints and pleura, may occur. An acute fibrinous bronchopneumonia with tissue necrosis may develop after airborne infections.

Except for *M. bovis*, the exact role of mycoplasmas and ureaplasmas in BRD requires better definition. Mycoplasmas may be recovered from the respiratory tract of nonpneumonic calves, but the frequency of isolation is greater in those with respiratory tract disease. The mycoplasmas commonly recovered from the lungs of pneumonic calves include *Mycoplasma dispar, Ureaplasma* spp. Experimental infections usually result in unapparent to mild signs of respiratory disease. This does not preclude a synergistic role for mycoplasmas in conjunction with viruses and bacteria in BRD. Lesions described include peribronchial and peribronchiolar lymphoid cuffing and alveolitis. Culture of these organisms requires special media and conditions and may take up to a week for growth of the organisms.

Chlamydiae have been identified in various parts of the world as a cause of enzootic pneumonia in calves. The causative agent is *Chlamydia psittaci*. Some respiratory isolates from calves have properties of immunotypes 1 and 6 and are similar to strains recovered from intestinal infections and abortions of cattle and sheep. Immunotype 6 has been recovered from pneumonic lungs of calves and pigs. Thus, the GI tract must be considered as an important site in the pathogenesis of chlamydial infections and as a natural reservoir and source of the organisms. Chlamydial pneumonia has affected calves under a whole range of conditions, including dairy farms. A synergism between *Chlamydia* and *P. haemolytica* has been demonstrated experimentally. Calves with chlamydial pneumonia are usually febrile, lethargic, and dyspneic, and have a serous and later mucopurulent nasal discharge and a dry hacking cough. Calves of weanling age are affected most frequently, but older cattle may also show signs of infection. The acute pulmonary lesion is a bronchointerstitial pneumonia. The anteroventral parts of the lungs are affected but, in severe cases, entire lobes may be involved. The dry cough is attributed to tracheitis. Microscopic changes in the lungs include suppurative bronchitis and alveolitis progressing to type II pneumocyte hyperplasia and interstitial thickening.

Bovine genital campylobacteriosis is a venereal disease of cattle characterized primarily by early embryonic death, infertility, a protracted calving season, and occasionally, abortion. Distribution is probably worldwide. The cause is the motile, gram-negative, curved or spiral, polar flagellated bacterium *Campylobacter fetus venerealis* or *Campylobacter fetus fetus*. For many years, it was thought that *C. fetus fetus* (formerly *C. fetus intestinalis*) was generally an intestinal organism, only occasionally caused abortion in cattle, and was not a cause of infertility. However, it has been shown that *C. fetus fetus* may also be a significant cause of the classic infertility syndrome usually attributed to *Campylobacter fetus venerealis*. There are several strains of *C. fetus fetus*, and the only way to determine if a strain is a cause of infertility is to test that possibility in a group of heifers. *Campylobacter* spp are very labile and are destroyed quickly by heating, drying, and exposure to the atmosphere. Unless cultured quickly after collection from the animal and grown under microaerophilic or anaerobic conditions, campylobacters will not grow. *Campylobacter fetus* is transmitted venereally and also by contaminated instruments, bedding, or by artificial insemination using contaminated semen. Individual bulls vary in their susceptibility to infection because some become permanent carriers, while others appear to be resistant to infection. Bulls may also transmit the infection mechanically for several hours after copulating with an infected cow. In cows, the duration of the carrier state is also variable; some clear the infection rapidly, while others may carry *C. fetus* for ≥2 yr. IgA antibodies are shed in cervical mucus in significant amounts in ~50% of cows for several months after infection and are useful diagnostically. Although most of the genital tract may be free of infection when a cow eventually conceives, the vagina may remain chronically infected, even through pregnancy. Cows are systemically normal, but there is are variable degrees of mucopurulent endometritis that causes early embryonic death, prolonged luteal phases, irregular estrous cycles, repeat breeding and, as a result, protracted calving periods. Observed abortions are not common. In herds not managed intensively, disease may be noticed only when pregnancy examinations reveal low or marginally low pregnancy rates but, more importantly, great variations in gestation lengths, especially when the disease has recently been introduced to the herd. In subsequent years, infertility is usually confined to replacement heifers and a few susceptible cows. Bulls are asymptomatic and produce normal semen.

Leptospirosis is a contagious disease of animals, including man, caused by various immunologically distinct leptospiral serovars, most of which are regarded as subgroups of *Leptospira interrogans*. Infections may be asymptomatic or cause various signs, including fever, icterus, hemoglobinuria, renal failure, infertility, abortion, and death. After acute infection, leptospires frequently localize in the kidneys or reproductive organs and are shed in the urine, sometimes in large numbers for months or years. Because the organisms survive in surface waters for extended periods, the disease is often waterborne.

In the U.S. the disease is primarily due to the serovars *Leptospira hardjo, Leptospira interrogans* serovar *hardjo* (*hardjo Prajitno*), *L. borgpetersenii* serovar *hardjo* (*hardjo Bovis*), *Leptospira pomona*, and *Leptospira grippotyphosa*. However, *Leptospira canicola* and *Leptospira icterohaemorrhagiae* serovars also have been isolated. Calves may have fever, anorexia, and dyspnea, and in *Leptospira pomona* infections, icterus, hemoglobinuria, and anemia. Body temperature may rise suddenly to 40.5-41° C. Hemoglobinuria rarely lasts longer than 48-72 hrs. Icterus clears rapidly and is followed by anemia. The RBC's begin to increase in number by 4-5 days and return to normal 7-10 days later. However, *Leptospira hardjo* infections usually do not cause hemolytic anemia, which makes diagnosis more difficult. Morbidity and mortality are higher in calves than in adult cattle. In older cattle, signs vary greatly and diagnosis is more difficult. Enzootic *Leptospira hardjo* infections, which usually result in abnormal milk, are more obvious in dairy than in beef cattle. Signs usually are restricted to lowered milk and calf production; a hemolytic crisis does not occur. The milk is thick, yellow, and blood-tinged; it may contain clots, although there is little evidence of mammary inflammation. Milk production returns to normal in 10-14 days, even in the absence of treatment. Abortion and stillbirths, which are common in *Leptospira pomona* infections and sporadic in *Leptospira hardjo* infections, generally occur 3-10 weeks after initial infection. The abortions are more common during the third trimester. An abortion storm in a breeding herd is often the first indication that leptospirosis exists, because the mild initial signs often pass unnoticed. In endemically infected herds, abortions occur mostly in younger animals and are sporadic, rather than being manifested as abortion storms. Calves reared by previously infected cows are protected by colostral antibodies for up to 6 months. The calves generally have an antibody titer similar to that of their dams. In the acute form, anemia, icterus, hemoglobinuria, and submucosal hemorrhages are prominent. The kidneys are swollen, with multifocal petechial and ecchymotic hemorrhages that become pale with time. The liver may be swollen, with minute areas of focal necrosis. Petechiae in other organs are seen in fulminating cases; however, in the more prevalent *Leptospira hardjo* infections, the lesions are primarily restricted to the kidneys.

Brucellosis is caused by bacteria of the genus *Brucella* and is characterized by abortion, retained placenta, and to a lesser extent, orchitis and infection of the accessory sex glands in males. The disease in cattle, water buffalo, and bison is caused almost exclusively by *Brucella abortus*; however, *Brucella suis* or *Brucella melitensis* is occasionally implicated in some cattle herds. *Brucella suis* does not appear to be contagious from cow to cow. *Brucella abortus* Infection spreads rapidly and causes many abortions in unvaccinated herds. Typically, in a herd in which disease is endemic, an infected cow aborts only once after exposure; subsequent gestations and lactations appear normal. After exposure, many cattle become bacteremic for a short period and develop agglutinins and other antibodies; others resist infection, and a small percentage of infected cows recover. A positive serum agglutination test usually precedes abortion or a normal parturition but may be delayed in ~15% of animals. The incubation period may be variable and is related to the stage of gestation at the time of exposure. Organisms are shed in milk and uterine discharges, and the cow may become temporarily sterile. Bacteria may be found in the uterus during pregnancy, uterine involution, and infrequently, for a prolonged time in the nongravid uterus. Shedding from the vagina largely disappears with reduction of the fluids after parturition. Some infected cows that aborted previously shed brucellae from the uterus at subsequent normal parturitions. Organisms are shed in milk for a variable length of time—in most cattle for life. Natural transmission occurs by ingestion of organisms, which are present in large numbers in aborted fetuses, fetal membranes, and uterine discharges. Cattle may ingest contaminated feed and water, or lick contaminated genitals of other animals. Venereal transmission by infected bulls to susceptible cows appears to be rare. Transmission may occur by artificial insemination when *Brucella*-contaminated semen is deposited in the uterus but, reportedly, not when deposited in the midcervix. Brucellae may enter the body through mucous membranes, conjunctivae, wounds, or even intact skin. Mechanical vectors (eg, other animals, including man) may spread infection. Brucellae have been recovered from fetuses and from manure that has remained in a cool environment for >2 mo. Exposure to direct sunlight kills the organisms within a few hours. Abortion is the most obvious manifestation. Infections may also cause stillborn or weak calves, retained placentas, and reduced milk yield. Usually, general health is not impaired in uncomplicated abortions. Seminal vesicles, ampullae, testicles, and epididymides may be infected in bulls; therefore, organisms are in the semen. Agglutinins may be demonstrated in seminal plasma from infected bulls. Testicular abscesses may occur. Long-standing infections may result in arthritic joints in some cattle.

Clostridia are relatively large, anaerobic, spore-forming, rod-shaped organisms. The spores are oval, sometimes spherical, and are central, subterminal, or terminal in position. The vegetative forms of clostridia in tissue fluids of infected animals occur singly, in pairs, or rarely in chains. Differentiation of the various pathogenic and related species is based on cultural characteristics, spore shape and position, biochemical reactions, and the antigenic specificity of toxins or surface antigens. The natural habitats of the organisms are the soil and intestinal tract of animals, including man. Pathogenic strains may be acquired by susceptible animals either by wound contamination or by ingestion. Diseases thus produced are a constant threat to successful livestock production in many parts of the world.

*Clostridium haemolyticum* is a soil-borne organism that may be found naturally in the GI tract of cattle. It may survive for long periods in contaminated soil or in bones from carcasses of animals that had been infected. After ingestion, latent spores ultimately become lodged in the liver. The incubation period is extremely variable, and the onset depends on the presence of a locus of anaerobiosis in the liver. Such a nidus for germination is most often caused by fluke infection, much less often by high nitrate content of the diet, accidental liver puncture, liver biopsy, or any other cause of localized necrosis. When conditions for anaerobiosis are favorable, the spores germinate, and the resulting vegetative cells multiply and produce β toxin (phospholipase C), which causes intravascular hemolysis and its sequelae, including hemolytic anemia and hemoglobinuria. Cattle may be found dead without premonitory signs. Usually, there is a sudden onset of severe depression, fever, abdominal pain, dyspnea, dysentery, and hemoglobinuria. Anemia and jaundice are present in varying degrees. Edema of the brisket may occur. Hgb and RBC levels are quite low. The duration of clinical signs varies from ~12 hr in pregnant cows to ~3-4 days in other cattle. The mortality in untreated animals is ~95%. Some cattle suffer from subclinical attacks of the disease and thereafter act as immune carriers. Dehydration, anemia, and sometimes subcutaneous edema are present. There is bloody fluid in the abdominal and thoracic cavities. The lungs are not grossly affected, and the trachea contains bloody froth with hemorrhages in the mucosa. The small intestine and occasionally the large intestine are hemorrhagic; their contents often contain free or clotted blood. An anemic infarct in the liver is virtually pathognomonic; it is slightly elevated, lighter in color than the surrounding tissue, and outlined by a bluish red zone of congestion. The kidneys are dark, friable, and usually studded with petechiae. The bladder contains purplish red urine. After death, rigor mortis sets in more rapidly than usual.

*Clostridium chauvoei* occurs naturally in the intestinal tract of animals. It probably may remain viable in the soil for many years, although it does not actively grow there. Contaminated pasture appears to be a source of organisms. Outbreaks of blackleg have occurred in cattle on farms in which recent excavations have occurred, which suggests that disturbance of soil may activate latent spores. The organisms probably are ingested, pass through the wall of the GI tract, and after gaining access to the bloodstream, deposited in muscle and other tissues. In cattle, blackleg infection is endogenous, in contrast to malignant edema. Lesions develop without any history of wounds, although bruising or excessive exercise may precipitate some cases. Commonly, the animals that contract blackleg are of the beef breeds, in excellent health, gaining weight, and usually the best animals of their group. Outbreaks occur in which a few new cases are found each day for several days. Most cases occur in cattle from 6 months to 2 years old, but thrifty calves as young as 6 weeks and cattle as old as 10-12 years may be affected. The disease usually occurs in summer and fall and is uncommon during the winter. In sheep, the disease is not restricted to the young, and most cases follow some form of injury such as shearing cuts, docking, crutching, or castration. Usually, onset is sudden and a few cattle may be found dead without premonitory signs. Acute lameness and marked depression are common. Initially, there is a fever but, by the time clinical signs are obvious, the temperature may be normal or subnormal. Characteristic edematous and crepitant swellings develop in the hip, shoulder, chest, back, neck, or elsewhere. At first, the swelling is small, hot, and painful. As the disease rapidly progresses, the swelling enlarges, there is crepitation on palpation, and the skin becomes cold and insensitive as the blood supply to the area diminishes. General signs include prostration and tremors. Death occurs in 12-48 hrs. In some cattle, the lesions are restricted to the myocardium and the diaphragm, with no reliable ante mortem evidence of the localized lesion.

*Clostridium novyi* has been suspected but not yet confirmed as a cause of sudden death in cattle and pigs fed high-level grain diets, and in which pre-existing lesions of the liver were not detectable. The lethal and necrotizing toxins (primarily a toxin) damage hepatic parenchyma, thereby permitting the bacteria to multiply and produce a lethal amount of toxin. Usually, death is sudden with no well-defined signs. Affected animals tend to lag behind the flock, assume sternal recumbency, and die within a few hours. Most cases occur in the summer and early fall when liver fluke infection is at its height. The disease is most prevalent in 1- to 4-year-old sheep and is limited to animals infected with liver flukes. Differentiation from acute fascioliasis may be difficult, but peracute deaths of animals that show typical lesions on necropsy should arouse suspicion of infectious necrotic hepatitis. The most characteristic lesions are the greyish yellow necrotic foci in the liver that often follow the migratory tracks of the young flukes. Other common findings are an enlarged pericardial sac filled with straw-colored fluid, and excess fluid in the peritoneal and thoracic cavities. Usually, there is extensive rupture of the capillaries in the subcutaneous tissue, which causes the adjacent skin to turn black (hence the common name, black disease).

*Clostridium septicum* is found in soil and intestinal contents of animals (including man) throughout the world. Infection ordinarily occurs through contamination of wounds containing devitalized tissue, soil, or some other tissue-debilitant. Wounds caused by accident, castration, docking, unsanitary vaccination, and parturition may become infected. General signs, such as anorexia, intoxication, and high fever, as well as local lesions, develop within a few hours to a few days after predisposing injury. The local lesions are soft swellings that pit on pressure and extend rapidly because of the formation of large quantities of exudate that infiltrates the subcutaneous and intramuscular connective tissue of the affected areas. The muscle in such areas is dark brown to black. Accumulations of gas are uncommon. Severe edema of the head of rams occurs after infection of wounds inflicted by fighting. Malignant edema associated with lacerations of the vulva at parturition is characterized by marked edema of the vulva, severe toxemia, and death in 24-48 hours. Similarity to blackleg is marked, and differentiation made on necropsy is unreliable; laboratory confirmation is the only certain procedure. Horses and pigs are susceptible to malignant edema but not to blackleg.

Infectious disease caused by *Clostridium sordellii* is also manifested as malignant edema in cattle, and also characterized by a nongaseous, nonhemorrhagic, edematous swelling of the head, face, and neck of young rams. This infection is initiated in young rams by their continual butting of one another. The bruised and battered subcutaneous tissues provide conditions suitable for growth of pathogenic clostridia, and the breaks in the skin offer an opportunity for their entrance Infection with *C. perfringens* types A, B and C causes severe enteritis, dysentery, toxemia, and high mortality in young calves. Types B and C both produce the highly necrotizing and lethal β toxin that is responsible for the severe intestinal damage. This toxin is sensitive to proteolytic enzymes, and disease is associated with inhibition of proteolysis in the intestine. Sow colostrum, which contains a trypsin inhibitor, has been suggested as a factor in the susceptibility of young piglets. Type C also causes enterotoxemia in adult cattle. In calves, there is acute diarrhea, dysentery, abdominal pain, convulsions, and opisthotonos. Death may occur in a few hours, but less severe cases survive for a few days, and recovery over a period of several days is possible. Hemorrhagic enteritis with ulceration of the mucosa is the major lesion in all species. Grossly, the affected portion of the intestine is deep blue-purple and appears at first glance to be an infarction associated with mesenteric torsion. Smears of intestinal contents may be examined for large numbers of gram-positive, rod-shaped bacteria, and filtrates made for detection of toxin and subsequent identification by neutralization with specific antiserum.

This classic enterotoxemia caused by *C. perfringens* type D rarely occurs in cattle. It is worldwide in distribution and may occur in animals of any age. The disease has been suspected in well-nourished beef calves nursing high-producing cows grazing lush pasture and in sudden death syndrome in feedlot cattle; however, supportive laboratory evidence in the latter is lacking. Acutely affected calves not found dead show mania, convulsions, blindness, and death in a few hours. Subacutely affected calves are stuporous for a few days and may recover.

Tetanus toxemia is caused by a specific neurotoxin produced by *Clostridium tetani* in necrotic tissue. Almost all mammals are susceptible to this disease. Although tetanus is worldwide in distribution, there are some areas, such as the northern Rocky Mountain section of the USA, where the organism is rarely found in the soil and where tetanus is almost unknown. In general, the occurrence of *C. tetani* in the soil and the incidence of tetanus in man and horses is higher in the warmer parts of the various continents. *Clostridium tetani*, an anaerobe with terminal, spherical spores, is found in soil and intestinal tracts. In most cases, it is introduced into the tissues through wounds, particularly deep puncture wounds, which provide a suitable anaerobic environment.

Infection with *Salmonella* spp may produce diarrhea in animals of all ages, especially those that are stressed, closely stocked, or exposed to a heavily contaminated feed or water supply. Salmonellosis is caused by many species of salmonellae and characterized clinically by one or more of three major syndromes—septicemia, acute enteritis, and chronic enteritis. The incidence has increased with the intensification of livestock production. Young calves usually develop the septicemic form. Adult cattle develop acute enteritis. Chronic enteritis may develop occasionally in cattle. Pregnant animals may abort. In older animals, the disease is manifested by dysentery and toxemia, and mortality may be significant. While many other *Salmonella* spp may cause disease, the more relevant in cattle are *S. typhimurium, S. dublin*, and *S. newport*. Although their resulting clinical patterns are not distinct, different species of salmonellae tend to differ in their epidemiology. Plasmid profile and drug-resistance patterns are sometimes useful markers for epidemiologic studies. Feces of infected animals may contaminate feed and water, milk, fresh and processed meats from abattoirs, plant and animal products used as fertilizers or feedstuffs, pasture and rangeland, and many inert materials. The organisms may survive for months in wet, warm areas such as in feeder pig barns or in water dugouts but survive less than 1 week in composted cattle manure. Rodents and wild birds also are sources of infection. The prevalence of infection varies among species and countries and is much higher than the incidence of clinical disease, which is commonly precipitated by stressful situations such as sudden deprivation of feed, transportation, drought, crowding, parturition, and the administration of some drugs.

Further relevant gastro-intestinal pathogens that may be used in the present invention include *Escherichia coli, Cryptosporidium parvum* and *Mycobacterium avium paratuberculosis. Escherichia coli* infection causes severe intestinal disease in young animals characterized as neonatal diarrhea, post weaning diarrhea, edema disease, and/or septicemia depending upon the virulence factors present in the strain causing the infection. Calves infected with pathogenic *E. coli* may develop severe diarrhea causing fatal dehydration, or fatal septicemic infections. Paratuberculosis is a chronic contagious enteritis characterized by persistent and progressive diarrhea, weight loss, debilitation, and eventually death. It affects cattle, sheep, goats, llamas, camels, farmed deer, and other domestic, exotic, and wild ruminants. It has also been recognized in wild rabbits; horses and pigs may be infected experimentally. Distribution is worldwide.

Animals with paratuberculosis should be considered as potential zoonotic risks until the situation is clarified. The causative organism is *Mycobacterium avium paratuberculosis*, formerly known as *M. paratuberculosis* or *M. johnei*. Occasionally, other *M. avium* subspecies are isolated from cases. The organism is quite resistant and may survive on pasture for more than 1 year, but sunlight, alkaline soils, and drying reduce its survival rate. It is shed in large numbers in feces of infected animals, and infection is acquired by ingestion of contaminated feed and water. Introduction of the disease into a clean herd is usually by subclinically infected carriers. Infection is acquired early in life, but clinical signs rarely develop in cattle <2 years old. Resistance increases with age, and cattle first exposed as adults are unlikely to become infected. Most calves are infected soon after birth either by nursing udders contaminated with feces from infected animals or by being housed in contaminated pens. The organism may also be present in colostrum and milk of infected cows, and intrauterine infections have also been described. After ingestion, the bacteria infect macrophages in the mucosa of the lower small intestine and in associated lymph nodes. Most animals will eliminate infection by an early cell-mediated immune response that encourages microbicidal activity in macrophages. In susceptible animals, the organisms multiply and provoke a chronic enteritis that leads to clinical disease. This may take months to years to develop and is usually paralleled by a decline in cell-mediated immunity and a rise in ineffective serum antibody. However, fecal shedding begins before clinical signs are apparent. *Mycobacterium avium* paratuberculosis may be isolated from feces, mesenteric and ileocecal lymph nodes, thickened intestinal walls, and less frequently the udder and the reproductive tracts of both sexes.

Cryptosporidiosis is an enterocolitis of cosmopolitan distribution caused by the coccidian parasite *Cryptosporidium parvum*. It is not host-specific and is common in young ruminants, particularly calves; it is also found in man and pigs and is rare in dogs, cats, and horses. Other cryptosporidia cause disease in reptiles and birds. The disease in calves, characterized by weight loss and watery diarrhea, is clinically indistinguishable from many other causes of calf diarrhea. *Cryptosporidium parvum* is a minute protozoan that is transmitted by the fecal-oral route. Oocysts are sporulated (four sporozoites) when shed in the feces and, therefore, are immediately infective. The mean incubation period is ~4 days. Calves 1-3 weeks old seem to be most susceptible. Signs such as anorexia, weight loss, diarrhea, and tenesmus, resemble those caused by several other intestinal pathogens; however, infections without signs do occur. Uncomplicated cryptosporidiosis is seldom fatal. Disease may be severe in immunocompromised individuals. If severe disease in calves is seen, other disease agents or concurrent infections should be ruled out. Although *C. parvum* may infect virtually the entire intestinal tract, the distal small intestine usually is affected most severely. Infection in horses is limited to the small intestine.

Gross lesions may consist of hyperemic intestinal mucosa and yellowish intestinal contents. Microscopically, mild to severe villous atrophy with spherical organisms in the brush border is evident. Unlike *Eimeria* and *Isospora* spp, which are intracellular parasites, *C. parvum* is intramembranous and resides within the brush border of the intestinal epithelial cells.

Inflammation of the mammary gland (mastitis) is almost always due to the effects of infection by bacterial or mycotic pathogens. Mastitis may be associated with infection by many other organisms, including *Streptococcus uberis, Streptococcus dysgalactiae, Streptococcus agalactiae, Staphylococcus aureus, Escherichia coli, Klebsiella* spp. *Pseudomonas aeruginosa, Actinomyces pyogenes, Mycoplasma* spp, *Nocardia asteroides, Serratia, Mycobacterium* spp, *Clostridium perfringens, Pasteurella* spp, yeasts, and *Prototheca* spp.

Dermatomycoses (Dermatophytosis) in animals are anthropozoonotic diseases of the skin and related tissue. Clinical symptoms are characterized by loss of hair in the affected area, hyperemia, scaling and asbestos-like scabs. Inflammation is often accompanied by suppuration. Dermatomycoses are often also characterized by localized infection of the skin. Dermatomycoses in animals carry a substantial socioeconomic impact. Diseased animals required prolonged treatment and may spread infection to both animals and humans. Dermatophytosis are caused by mycosis infections of *Trichophyton* spp. or *Microsporum* spp. Most relevant causes for cattle are *Trichophyton verrucosum, Trichophyton mentagrophytes* or *Trichophyton sarkisovii.*

An infection of the lower respiratory tract, usually resulting in bronchitis or pneumonia, may be caused by any of several parasitic nematodes, including *Dictyocaulus viviparus* in cattle. This lungworm belongs to the superfamily Trichostrongyloidea and has direct life cycles. The cattle lungworm is common in northwest Europe and is the cause of severe outbreaks of "husk" or "hoose" in young grazing cattle. Because *D. viviparus* infection in cattle is the most economically important, it has been most investigated and many of the observations from it are applicable to the other species. Clinical disease usually develops on first exposure to sufficient infective larvae. In cattle, this usually occurs during their first season at pasture; however, an increase in the number of older cattle affected has been reported. Signs of lungworm infection range from moderate coughing with slightly increased respiratory rates to severe persistent coughing and respiratory distress and even failure. Reduced weight-gains, reduced milk yields, and weight loss accompany many infections in cattle. Patent subclinical infections may occur in all species. The most consistent signs in cattle are tachypnea and coughing.

Trichomoniasis is a venereal protozoal disease of cattle characterized primarily by early fetal death and infertility, resulting in extended calving intervals. Distribution is probably worldwide. The causative protozoan, *Trichomonas* (*Tritrichomonas*) *foetus*, is pyriform and ordinarily 10-15×5-10 μm, but there is considerable pleomorphism. It may become spherical when cultured in artificial media. At its anterior end, there are three flagella about the same length as the body of the parasite. An undulating membrane extends the length of the body and is bordered by a marginal filament that continues beyond the membrane as a posterior flagellum. Although *T. foetus* may survive the process used for freezing semen, it is killed by drying or high temperatures. *Trichomonas foetus* is found in the genital tracts of cattle. When cows are bred naturally by an infected bull, 30-90% become infected, suggesting that strain differences exist. Variation in breed susceptibility to trichomoniasis may also exist. Bulls of all ages may remain infected indefinitely but this is less likely in younger males. By contrast, most cows are free of infection within 3 months after breeding. However, immunity is not long lasting and reinfection does occur. Transmission may also occur when the semen from infected bulls is used for artificial insemination. The most common sign is infertility caused by embryonic death. This results in repeat breeding and a prolonged calving season. Fetal death and abortions may also occur but are not as common as losses earlier in gestation. *Trichomonas foetus* has been found in vaginal cultures taken as late as 8 months of gestation and, apparently, live calves may be born to infected dams. Pyometra occasionally develops after breeding.

*Neospora caninum* is an obligate intracellular protozoan parasite that has been confused previously with *Toxoplasma gondii*. Only asexual stages are known, and they resemble *T. gondii*. The complete life cycle of *N. caninum* is unknown, but it may be transmitted transplacentally in dogs, cattle, goats, sheep, and cats, and subsequent offspring may be affected. Tachyzoites are 5-7×1-5 μm, depending on the stage of division. They divide by endodyogeny. Tachyzoites are found in myocytes, neural cells, dermal cells, macrophages, and other cells. Tissue cysts up to 100 μm in diameter are found in neural cells; the cyst wall is amorphous and up to 4 μm thick. Cysts have no septa and enclose slender 7×1.5 μm bradyzoites. In dairy cattle, *N. caninum* is a major cause of abortion in many countries, particularly in the USA. Calves may be aborted, stillborn, born underweight, weak, or paralyzed, or they may become paralyzed within 4 weeks of birth. Nonsuppurative encephalitis is the main lesion in aborted fetal tissues. Abortion may occur throughout gestation, and some cows may abort again; dams of these calves are clinically normal.

Babesiosis is caused by intraerythrocytic protozoan parasites of the genus *Babesia*. A wide range of domestic and wild animals and occasionally man is affected by the disease, which is transmitted by ticks and has a worldwide distribution. Two important species in cattle—*Babesia bigemina* and *Babesia bovis*—are widespread in tropical and subtropical areas and are the focus of this discussion. In endemic areas, two features are important in determining the risk of clinical disease: 1) calves have a degree of immunity (related both to colostral-derived antibodies and to age) that persists for ~6 months, and 2) animals that recover from *Babesia* infections are immune for life. Thus, at high levels of tick transmission, all newborn calves will become infected with *Babesia* by 6 mos. of age, show few if any clinical signs, and subsequently be immune. This situation of endemic stability may be upset by either a natural (eg, climatic) or artificial (eg, acaricide treatment) reduction in tick numbers to levels where tick transmission of *Babesia* to calves is insufficient to ensure all are infected during this critical early period. Other circumstances that may lead to clinical outbreaks include the introduction of susceptible cattle to endemic areas and the incursion of *Babesia*-infected ticks into previously tick-free areas. Strain variation in immunity has been demonstrated but is probably not of significance in the field. The acute disease generally runs a course of ~1 week. The first sign is fever (frequently 41° C. or higher), which persists throughout, and is accompanied later by inappetence, increased respiratory rate, muscle tremors, anemia, jaundice, and loss of weight with hemoglobinemia and hemoglobinuria in the final stages. CNS involvement due to sludging of parasitized erythrocytes in brain capillaries occurs frequently with *B. bovis* infection. Either constipation or diarrhea may be present. Pregnant cows often abort. With virulent strains of *B. bovis*, a hypotensive shock syndrome, combined with generalized non-specific inflammation, coagulation disturbances, and erythrocytic stasis in capillaries, contribute to the pathogenesis. With most strains of *B. bigemina*, the pathogenic effects relate more directly to erythrocyte destruction. Animals that recover from the acute disease remain infected for a number of years with *B. bovis* and for a few months in the case of *B. bigemina*. No signs are apparent during this carrier state. Lesions include an enlarged and friable spleen; a swollen liver with an enlarged gallbladder containing thick granular bile; congested, dark-colored kidneys; and generalized anemia and jaundice. The urine is often, but not invariably, red. Other organs, including the brain and heart, may show congestion or petechial hemorrhages. The susceptibility of cattle breeds to *Babesia* infections varies; for example, Brahman cattle are more resistant to *B. bovis* infection than are British breeds.

As described above, the present invention also relates to combination vaccines and/or the combined use of immunogenic compositions for the treatment and/or prophylaxis of cattle against microbiological infections, wherein the infections are caused by *M. bovis* and at least one further relevant cattle pathogen. The combination vaccine as described herein comprises at least one *M. bovis* antigen, preferably the attenuated, avirulent *M. bovis* as provided herewith and one or more further immunologically active components effective for the treatment and/or prophylaxis of infections caused by one or more further relevant pathogen of cattle. The combined use or the method of co-administration of two or more antigens of pathogens affecting cattle comprises administering a first immunogenic composition comprising *M. bovis* antigen, preferably the attenuated, avirulent *M. bovis* as provided herewith and at least one further immunologically active component effective for the treatment and/or prophylaxis of infections caused by a further relevant pathogen of cattle.

Relevant cattle pathogens other than *M. bovis* include those listed in the background section above but are not limited to: i) pathogens of viral origin such as Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), and Adenovirus and Astrovirus; ii) pathogens of bacterial origin, such as *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Eschericia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Staphylococcus aureus, Streptococcus dysgalactiae, Mycoplasma dispar*, and *Ureaplasma* spp., and *Streptococcus uberis* iii) pathogens of other origin, such as *Tritrichomonas foetus, Trichophyton verrucosum, Trichophyton mentagrophytes, Trichophyton sarkisovii, Neospora caninum* (formerly *Toxoplasma gondii*), *Cryptsporidium parvum, Cryptsporidium hominis, Babesia bigemina* and *Babesia bovis*, and *Dictyocaulus viviparous* (Lungworm disease).

The combined use or the method of co-administration of two or more antigens of pathogens affecting cattle comprises administering a first immunogenic composition comprising *M. bovis* antigen, preferably the attenuated, avirulent *M. bovis* as provided herewith and at least one further immunologically active component effective for the treatment and/or prophylaxis of infections caused by a further pathogen of cattle, wherein said further pathogen of cattle is selected from the group consisting of: i) pathogens of viral origin such as Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), and Adenovirus and Astrovirus; ii) pathogens of bacterial origin, such as *Mannheimia haemolytica* (formerly *Pasteurella haemolytica*), *Pasteurella multocida, Haemophilus somnus* (*Histophilus ovis* and *Haemophilus* agni), *Actinomyces* (*Corynebacterium*), *Actinomyces pyogenes, Chlamydia psittaci, Campylobacter fetus venerealis* and *Campylobacter fetus* fetus (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Staphylococcus aureus, Streptococcus dysgalactiae, Mycoplasma dispar*, and *Ureaplasma* spp., and *Streptococcus uberis* and iii) pathogens of other origin, such as *Tritrichomonas foetus, Trichophyton verrucosum, Trichophyton mentagrophytes, Trichophyton sarkisovii, Neospora caninum* (formerly *Toxoplasma gondii*), *Cryptsporidium parvum, Cryptsporidium hominis, Babesia bigemina* and *Babesia bovis*, and *Dictyocaulus viviparous* (Lungworm disease) or any other pathogen listed in the background section or known to be pathogenic in cattle.

The present invention relates to combination vaccines and/or the combined use of immunogenic compositions for the treatment and/or prophylaxis of cattle against microbiological infections, wherein the infections are caused by *M. bovis* and at least one further cattle relevant pathogen, wherein said vaccine or combined use comprises or makes use of an *M. bovis* antigen, preferably the avirulent, attenuated *M. bovis*, as described herein, and a further immunologically active component effective for the treatment and/or prophylaxis of infections caused by Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Lep-*

*tospira grippotyphosa, Leptospira hardjo* (*Leptospira hardjoprajitno* and *Leptospira hardjo-bovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Mycoplasma* spp, *Mycoplasma dispar*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis*, and *Dictyocaulus viviparous* (Lungworm disease) and/or any other pathogen known to be pathogenic in cattle, including the pathogens discussed in the background.

The combined use or the method of co-administration of two or more antigens of pathogens affecting cattle comprises administering a first immunogenic composition comprising *M. bovis* antigen, preferably the attenuated, avirulent *M. bovis*, as provided herewith, and at least one further immunogenic composition comprising one or more further immunologically active components effective for the treatment and/or prophylaxis of infections caused by a further pathogen of cattle, wherein said further pathogen of cattle is selected from the group consisting of: Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (PPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Mycoplasma* spp, *Mycoplasma dispar, Mycoplasma bovis*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis*, and *Dictyocaulus viviparous* (Lungworm disease) and/or any other pathogen listed in the background section or known to be pathogenic in cattle. Preferably, the further immonogenic composition comprises an antigen of one or more of any of the cattle relevant pathogens as listed above.

According to a further embodiment, the present invention relates to a combination vaccine or the combined use of immunogenic compositions for the treatment and/or prophylaxis of cattle against infections of the respiratory and/or reproductive systems in cattle, wherein the combination vaccine or combined use comprises a *M. bovis* antigen, preferably the attenuated and avirulent *M. bovis* as described herein, and at least one further immunologically active component effective for the treatment and/or prophylaxis of infections caused by IBR [combo 001]. According to a preferred embodiment, the combination vaccine comprises *M. bovis*, preferably the attenuated and avirulent *M. bovis*, as described herein, and at least one antigen of IBR [combo 002]. According to a preferred embodiment, the IBR antigen is a live modified virus [combo 003]. According to a further embodiment, the combination vaccine of attenuated *M. bovis* and IBR contains an antibiotic, e.g. neomycin, for preservation [combo 004].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by PI-3 [combo 005]. According to a preferred embodiment, the combination vaccine comprises *M. bovis*, preferably the attenuated and avirulent *M. bovis* as described herein, and at least one antigen of PI-3 [combo 006]

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by BVDV (type 1 and/or type 2), preferably attenuated BVDV (type 1 and/or type 2) [combo 007]. According to a more preferred embodiment, the combination vaccine comprises *M. bovis*, preferably the attenuated and avirulent *M. bovis* as described herein and at least one antigen of BVDV (type 1 and/or type 2), preferably attenuated BVDV (type 1 and/or type 2) [combo 008].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by BHV [combo 009]. According to a preferred embodiment, the combination vaccine comprises *M. bovis*, preferably the attenuated and avirulent *M. bovis* as described herein, and at least one antigen of BHV [combo 010].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and PI-3 [combo 011]. According to a preferred embodiment, the combination vaccine comprises *M. bovis*, preferably the attenuated and avirulent *M. bovis* as described herein, and at least one antigen each of IBR and PI-3 [combo 012].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and BVDV (type 1 and/or type 2), preferably attenuated BVDV (type 1 and/or type 2) [combo 013]. According to a preferred embodiment, the combination vaccine comprises *M. bovis*, preferably the attenuated and avirulent *M. bovis* as described herein, and at least one antigen each of IBR and BVDV (type 1 and/or type 2), preferably attenuated BVDV (type 1 and/or type 2) [combo 014].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and BHV [combo 015]. According to a preferred embodiment, the combination vaccine comprises *M. bovis*, preferably the attenuated and avirulent *M. bovis* as described herein, and at least one antigen each of IBR and BHV [combo 016].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3 and BVDV (type 1 and/or type 2), preferably attenuated BVDV (type 1 and/or type 2) [combo 017]. According to a preferred embodiment, the combination vaccine comprises *M. bovis*, preferably the attenuated and avirulent *M. bovis* as described herein, and at least one antigen each of PI-3 and BVDV (type 1 and/or type 2), preferably attenuated BVDV (type 1 and/or type 2) [combo 018].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3 and BHV [combo 019]. According to a preferred embodiment, the combination vaccine comprises *M. bovis*, preferably the attenuated and avirulent *M. bovis* as described herein, and at least one antigen each of PI-3 and BHV [combo 020].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and BVDV (type 1 and/or type 2), preferably attenuated BVDV (type 1 and/or type 2) [combo 021]. According to a preferred embodiment, the combination vaccine comprises *M. bovis*, preferably the attenuated and avirulent *M. bovis* as described herein and at least one antigen each of IBR, PI-3 and BVDV (type 1 and/or type 2), preferably attenuated BVDV (type 1 and/or type 2) [combo 022]. Preferably, all viral antigens are modified live viruses [combo 023].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by BRSV and BVDV (type 1 and/or type 2), preferably attenuated BVDV (type 1 and/or type 2) [combo 024]. According to a preferred embodiment, the combination vaccine comprises *M. bovis*, preferably the attenuated and avirulent *M. bovis* as described herein, and at least one antigen of each BRSV and BVDV (type 1 and/or type 2), preferably attenuated BVDV (type 1 and/or type 2 [combo 025].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, BVDV (type 1 and/or type 2), preferably attenuated BVDV (type 1 and/or type 2 and BHV [combo 026]. According to a preferred embodiment, the combination vaccine comprises *M. bovis*, preferably the attenuated and avirulent *M. bovis* as described herein, and at least one antigen each of IBR BHV, and BVDV (type 1 and/or type 2), preferably attenuated BVDV (type 1 and/or type 2 [combo 027].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3, BVDV (type 1 and/or type 2), preferably attenuated BVDV (type 1 and/or type 2 and BHV [combo 028]. According to a preferred embodiment, the combination vaccine comprises *M. bovis*, preferably the attenuated and avirulent *M. bovis* as described herein, and at least one antigen each of PI-3 and BVDV (type 1 and/or type 2), preferably attenuated BVDV (type 1 and/or type 2 and BHV [combo 029].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and BHV [combo 030]. According to a preferred embodiment, the combination vaccine comprises *M. bovis*, preferably the attenuated and avirulent *M. bovis* as described herein, and at least one antigen each of IBR, BHV and PI-3 [combo 031].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, BVDV (type 1 and/or type 2), preferably attenuated BVDV (type 1 and/or type 2 and BHV [combo 032]. According to a more preferred embodiment, the combination vaccine comprises *M. bovis*, preferably the attenuated and avirulent *M. bovis* as described herein, and at least one antigen each of IBR BHV PI-3, and BVDV (type 1 and/or type 2), preferably attenuated BVDV (type 1 and/or type 2) [combo 033].

According to a further embodiment, the present invention relates to a combination vaccine for the treatment and/or prophylaxis of cattle against bacterial infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by *H. somnus* [combo 034]. According to a more preferred embodiment, the combination vaccine comprises *M. bovis*, preferably the attenuated and avirulent *M. bovis* as described herein, and at least one antigen of *H. somnus* [combo 035].

According to a further embodiment, the present invention relates to a combination vaccine for the treatment and/or prophylaxis of cattle against viral and bacterial infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and *H. somnus* [combo 036]. According to a more preferred embodiment, the combination vaccine comprises *M. bovis*, preferably the attenuated and avirulent *M. bovis* as described herein, and at least one antigen each of *H. somnus* and IBR [combo 037].

According to a further embodiment, the present invention relates to a combination vaccine for the treatment and/or prophylaxis of cattle against viral and bacterial infections of the respiratory and reproductive systems in cattle, wherein the combination vaccine comprises *M. bovis*, preferably the attenuated and avirulent *M. bovis* as described herein, and at least one further immunologically active components effective for the treatment and/or prophylaxis of infections caused by IBR, PI-3, and *H. somnus* [combo 038]. According to a more preferred embodiment, the combination vaccine comprises *M. bovis*, preferably the attenuated and avirulent *M. bovis* as described herein, and at least one antigen each of IBR, PI-3, and *H. somnus* [combo 039].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2) and *H. somnus* [combo 040]. According to a more preferred embodiment, the combination vaccine comprises *M. bovis*, preferably the attenuated and avirulent *M. bovis* as described herein, and at least one antigen each of IBR, PI-3 and BVDV (type 1 and/or type 2), preferably attenuated BVDV (type 1 and/or type 2) and one antigen of *H. somnus* [combo 041]. According to a further embodiment of said combination vaccine, the IBR, PI-3 antigens are killed viruses [combo 042]. According to a further embodiment, any of said combination vaccines, preferably the combination vaccine that comprises killed IBR and killed PI-3 antigens, contains neomycin and thimerosal as preservatives [combo 043].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and *H. somnus* [combo 044]. According to a more preferred embodiment, the combination vaccine comprises *M. bovis*, preferably the attenuated and avirulent *M. bovis* as described herein, and at least one antigen each of IBR, BHV, PI-3, and BVDV (type 1 and/or type 2), preferably attenuated BVDV (type 1 and/or type 2) and one antigen of *H. somnus* [combo 045].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 046]. According to a more preferred embodiment, the combination vaccine comprises *M. bovis*, preferably the attenuated and avirulent *M. bovis* as described herein and one or more antigens of at least one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 047].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 048]. According to a more preferred embodiment, the combination vaccine comprises *M. bovis*, preferably the attenuated and avirulent *M. bovis* as described herein and at least one antigen each of IBR and one or more pathogenic specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 049].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and *Leptospira pomona* [combo 050]. According to a more preferred embodiment, the combination vaccine comprises *M. bovis*, preferably the attenuated and avirulent *M. bovis* as described herein, and at least one antigen of IBR, preferably a live modified virus, and at least one *Leptospira pomona* bacterin [combo 51].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 052]. According to a more preferred embodiment, the combination vaccine comprises *M. bovis*, preferably the attenuated and avirulent *M. bovis* as described herein, and at least one antigen each of IBR, and PI-3, and one or more antigens each of one or more pathogenic specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 053].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae*, and *Leptospira pomona* [combo 054]. According to a more preferred embodiment, the combination vaccine comprises *M. bovis*, preferably the attenuated and avirulent *M. bovis* as described herein, and at least one antigen each of IBR, PI-3, *Leptospira canicola, Leptospira grippotyphosa, Leptospira hardjo, Leptospira icterohaemorrhagiae* and *Leptospira pomona* [combo 055].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2) and one or more pathogenic species of *Leptospira*, preferably selected from the grpup consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 056]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2) and one or more antigens each of one or more pathogenic species of *Leptospira*, preferably selected from the group consisting of *Leptospira canicola, Leptospira grippotyphosa, Leptospira borgpetersenii, Leptospira prajitno, Leptospira icterohaemmorrhagiae, Leptospira bovis, Leptospira interrogans* and *Leptospira pomona* [combo 057].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira* canicola, *Leptospira grippotyphosa, Leptospira hardjo* (*Leptospira hardjoprajitno* and/or *Leptospira hardjo-bovis*), *Leptospira icterohaemorrhagiae*, and *Leptospira pomona* [combo 058]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of *Leptospira canicola, Leptospira grippotyphosa, Leptospira hardjo* (*Leptospira hardjoprajitno* and/or *Leptospira hardjo-bovis*), *Leptospira icterohaemorrhagiae*, and *Leptospira pomona* [combo 059]. According to a preferred embodiment, the viral antigens are killed viruses and the bacterial antigens are bacterins [combo 060]. Preferably, said combination vaccines as described in this paragraph further contain neomycin and thimerosal as preservatives [combo 061].

According to a further embodiment, the combination vaccine comprises *M. bovis*, preferably the attenuated and avirulent *M. bovis* as described herein, live modified viruses of IBR, PI-3, BVDV (type 1 and/or type 2), preferably attenuated BVDV (type 1 and/or type 2), and bacterin of *Leptospira canicola, Leptospira grippotyphosa, Leptospira hardjo* (*Leptospira hardjoprajitno* and/or *Leptospira hardjo-bovis*), *Leptospira icterohaemorrhagiae* and *Leptospira pomona* [combo 062]. According to a further preferred embodiment, the combination vaccine described in this paragraph comprises neomycin as a preservative [combo 063].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira*

*interrogans* and *Leptospira pomona*. [combo 064]. According to a more preferred embodiment, the combination vaccine comprises *M. bovis*, preferably the attenuated and avirulent *M. bovis* as described herein, and at least one antigen each of IBR BHV, PI-3, and BVDV (type 1 and/or type 2), preferably attenuated BVDV (type 1 and/or type 2), and one or more antigens each of one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 065].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic species of *Leptospira*, as mentioned above, and *H. somnus* [combo 066]. According to a more preferred embodiment, the combination vaccine comprises *M. bovis*, preferably the attenuated and avirulent *M. bovis* as described herein, and at least one antigen of one or more pathogenic species of *Leptospira*, as mentioned above, and at least one antigen of *H. somnus* [combo 067].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic specie(s) of *Leptospira*, as mentioned above, and *H. somnus* [combo 068]. According to a more preferred embodiment, the combination vaccine comprises *M. bovis*, preferably the attenuated and avirulent *M. bovis* as described herein, and at least one antigen of IBR and at least one antigen each of one or more pathogenic species of *Leptospira*, as mentioned above, and at least one antigen of *H. somnus* [combo 069].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and one or more pathogenic specie(s) of *Leptospira*, as mentioned above, and *H. somnus* [combo 070]. According to a more preferred embodiment, the combination vaccine comprises *M. bovis*, preferably the attenuated and avirulent *M. bovis* as described herein, and at least one antigen each of IBR, PI-3, and at least one antigen each of one or more pathogenic species of *Leptospira*, as mentioned above, and at least one antigen of *H. somnus* [combo 071].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona* and *H. somnus* [combo 072]. According to a more preferred embodiment, the combination vaccine comprises *M. bovis*, preferably the attenuated and avirulent *M. bovis* as described herein, and at least one antigen each of IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona*, and *H. somnus* [combo 073].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, and *H. somnus* [combo 074]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of one or more pathogenic species of *Leptospira*, as mentioned above, and at least one antigen of *H. somnus* [combo 075].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira canicola, Leptospira grippotyphosa, Leptospira hardjo* (*Leptospirahardjo prajitno* and/or *Leptospira hardjo-bovis*), *Leptospira icterohaemorrhagiae, Leptospira pomona* and *H. somnus* [combo 076]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *Leptospira canicola, Leptospira grippotyphosa, Leptospira hardjo, Leptospira icterohaemorrhagiae, Leptospira pomona* and *H. somnus* [combo 077].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic specie(s) of *Leptospira*, as mentioned above, and *H. somnus* [combo 078]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV and one or more antigens each of one or more pathogenic species of *Leptospira*, as mentioned above, and at least one antigen of *H. somnus* [combo 079].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic specie(s) of *Leptospira*, as mentioned above, and *Campylobacter fetus* [combo 080]. According to a more preferred embodiment, the combination vaccine comprises *M. bovis*, preferably the attenuated and avirulent *M. bovis* as described herein, and at least one or more antigens each of one or more pathogenic species of *Leptospira*, as mentioned above, and at least one antigen of *Campylobacter fetus* [combo 081].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Leptospira canicola, Leptospira grippotyphosa, Leptospira hardjo* (*Leptospira hardjoprajitno* and/or *Leptospira hardjo-bovis*), *Leptospira lcterohaemorrhagiae, Leptospira pomona* and *Campylobacter fetus* [combo 082]. According to a preferred embodiment, the combination vaccine comprises *M. bovis*, preferably the attenuated and avirulent *M. bovis* as described herein, and at least antigen each of *Leptospira canicola, Leptospira grippotyphosa, Leptospira hardjo* (*Leptospira hardjoprajitno* and *Leptospira hardjo-bovis*), *Leptospira lcterohaemorrhagiae, Leptospira pomona* and *Campylobacter fetus* [combo 083]. According to a more preferred embodiment, the bacterial antigens are chemically inactivated, aluminum hydroxide adsorbed, whole cultures of said bacteria [combo 084]. According to a further preferred embodiment, said combination vaccine comprises gentamicin and Amphotericin B as preservatives [combo 085].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic specie(s) of *Leptospira*, as mentioned above, and *Campylobacter fetus* [combo 086]. According to a more preferred embodiment, the combination vaccine comprises *M. bovis*, preferably the attenuated and avirulent *M. bovis* as described herein, and at least one antigen of IBR and one or more antigens each of one or more pathogenic species of *Leptospira*, as mentioned above, and at least one antigen of *Campylobacter fetus* [combo 087].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and one or more pathogenic specie(s) of *Leptospira*, as mentioned above, and *Campylobacter fetus* [combo 088]. According to a more preferred embodiment, the combination vaccine comprises *M. bovis*, preferably the attenuated and avirulent *M. bovis* as described herein, and at least one antigen each of IBR, PI-3, and one or more antigens each of one or more pathogenic species of *Leptospira*, as mentioned above, and at least one antigen of *Campylobacter fetus* [combo 089].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, and *Campylobacter fetus* [combo 090]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of one or more pathogenic species of *Leptospira*, as mentioned above, and at least one antigen of *Campylobacter fetus* [combo 091].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV, one or more pathogenic specie(s) of *Leptospira*, as mentioned above, and *Campylobacter fetus* [combo 092]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV and one or more antigens each of one or more pathogenic species of *Leptospira*, as mentioned above, and at least one antigen of *Campylobacter fetus* [combo 093].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic specie(s) of *Leptospira*, as mentioned above, *H. somnus* and *Campylobacter fetus* [combo 094]. According to a more preferred embodiment, the combination vaccine comprises *M. bovis*, preferably the attenuated and avirulent *M. bovis* as described herein, and one or more antigens each of one or more pathogenic species of *Leptospira*, as mentioned above, and at least one antigen each of *H. somnus* and *Campylobacter fetus* [combo 095].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, one or more pathogenic specie(s) of *Leptospira*, as mentioned above, *H. somnus* and *Campylobacter fetus* [combo 096]. According to a more preferred embodiment, the combination vaccine comprises *M. bovis*, preferably the attenuated and avirulent *M. bovis* as described herein, and at least one antigen each of IBR, *H. somnus* and *Campylobacter fetus*, and one or more antigens each of one or more pathogenic species of *Leptospira*, as mentioned above, [combo 097].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, and one or more pathogenic specie(s) of *Leptospira*, as mentioned above, *H. somnus* and *Campylobacter fetus* [combo 098]. According to a preferred embodiment, the combination vaccine comprises *M. bovis*, preferably the attenuated and avirulent *M. bovis* as described herein, and at least one antigen each of IBR, PI-3, *H. somnus* and *Campylobacter fetus* and one or more atingens each of one or more pathogenic species of *Leptospira*, as mentioned above, [combo 099].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola, Leptospira grippotyphosa, Leptospira hardjo, Leptospira icterohaemorrhagiae, Leptospira pomona, H. somnus* and *Campylobacter fetus* [combo 100]. According to a further embodiment, the combination vaccine comprises *M. bovis*, preferably the attenuated and avirulent *M. bovis* as described herein, and at least one antigen each of IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona, H. somnus* and *Campylobacter fetus* [combo 101].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, *H. somnus* and *Campylobacter fetus* [combo 102]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *H. somnus* and *Campylobacter fetus* and one or more antigens each of one or more pathogenic species of *Leptospira*, as mentioned above [combo 100].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira Pomona, H. somnus* and *Campylobacter fetus* [combo 103]. According to a further embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona, H. somnus* and *Campylobacter fetus* [combo 104].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic specie(s) of *Leptospira*, as mentioned above, *H. somnus* and *Campylobacter fetus* [combo 105]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV, *H. somnus* and *Campylobacter fetus*, and one or more antigens each of one or more pathogenic species of *Leptospira*, as mentioned above, [combo 106].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by BHV, BVDV (type 1 and/or type 2), preferably attenuated BVDV (type 1 and/or type 2), PI-3, IBR, *Leptospira canicola, Leptospira grippotyphosa, Leptospira borgpetersenii Leptospira hardjo* (*Leptospira hardjoprajitno* and/or *Leptospira hardjo-bovis*), *Leptospira prajitno, Leptospira icterohaemmorrhagiae, Leptospira bovis, Leptospira interrogans* and *Campylobacter fetus* [combo 107]. According to a more preferred embodiment, the combination vaccine comprises attenuated *M. bovis*, as described herein, and at least one antigen each of BHV, BVDV (type 1 and/or type 2), preferably attenuated BVDV (type 1 and/or type 2), IBR, PI-3, *Leptospira canicola, Leptospira grippotyphosa, Leptospira borgpetersenii Leptospira hardjo* (*Leptospira hardjoprajitno* and/or *Leptospira hardjo-bovis*), *Leptospira prajitno, Leptospira icterohaemmorrhagiae, Leptospira borgpetersenii, Leptospira bovis, Leptospira* interrogans and *Campylobacter fetus* [combo 108].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica* and *Pasteurella multocida* [combo 109]. According to a preferred embodiment, the combination vaccine comprises *M. bovis*, preferably the attenuated and avirulent *M. bovis* as described herein, and at least one antigen each of *Pasteurella haemolytica* bacterin and *Pasteurella multocida* bacterin. [combo 110] According to a further preferred embodiment, said combination vaccine comprises neomycin and thimerosal as preservatives [combo 111].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica* and *Pasteurella multocida* [combo 112]. According to a preferred embodiment, the combination vaccine comprises *M. bovis*, preferably the attenuated and avirulent *M. bovis* as described herein, and at least one antigen of each of IBR, preferably as live modified viruses, *Pasteurella haemolytica* bacterin and *Pasteurella multocida* bacterin [combo 113]. According to a further preferred embodiment, said combination vaccine comprises neomycin and thimerosal as preservatives [combo 114].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica* and *Pasteurella multocida* [combo 115]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica* bacterin and *Pasteurella multocida* bacterin [combo 116]. According to a further preferred embodiment, said combination vaccine comprises neomycin and thimerosal as preservatives [combo 117].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica* and *Pasteurella multocida* [combo 118]. According to a preferred embodiment, the combination vaccine comprises *M. bovis*, preferably the attenuated and avirulent *M. bovis* as described herein, and at least one antigen each of IBR, PI-3, preferably as live modified viruses, BVDV (type 1 and/or type 2), preferably attenuated BVDV (type 1 and/or type 2), *Pasteurella haemolytica* bacterin and *Pasteurella multocida* bacterin [combo 119]. According to a further preferred embodiment, said combination vaccine comprises neomycin and thimerosal as preservatives [combo 120].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, BVDV (type 1 and/or type 2), preferably attenuated BVDV (type 1 and/or type 2), BHV, *Pasteurella haemolytica* and *Pasteurella multocida* [combo 121]. According to a preferred embodiment, the combination vaccine comprises *M. bovis*, preferably the attenuated and avirulent *M. bovis*, as described herein, and at least one antigen each of IBR, PI-3, BVDV (type 1 and/or type 2), preferably attenuated BVDV (type 1 and/or type 2), BHV, preferably as live modified viruses, *Pasteurella haemolytica* bacterin and *Pasteurella multocida* bacterin [combo 122]. According to a further preferred embodiment, said combination vaccine comprises neomycin and thimerosal as preservatives [combo 123].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and at least one further immunologically active component effective for the treatment and/or prophylaxis of infections caused by BRSV [combo 124]. According to a preferred embodiment, the combination vaccine comprises *M. bovis*, preferably the attenuated and avirulent *M. bovis* as described herein, and at least antigen of BRSV [combo 125].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, and BRSV [combo 126]. According to a preferred embodiment, the combination vaccine comprises *M. bovis*, preferably the attenuated and avirulent *M. bovis* as described herein, and at least antigen of each IBR, preferably as live modified viruses, and BRSV [combo 127].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, and BRSV [combo 128]. According to a preferred embodiment, the combination vaccine comprises *M. bovis*, preferably the attenuated and avirulent *M. bovis* as described herein, and at least one antigen eaxh of IBR, PI-3, preferably as live modified viruses, and BRSV [combo 129].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BRSV, and BVDV (type 1 and/or type 2), preferably attenuated BVDV (type 1 and/or type 2) [combo 130]. According to a preferred embodiment, the combination vaccine comprises *M. bovis*, preferably the attenuated and avirulent *M. bovis* as described herein, and at least one antigen each of IBR, PI-3, BRSV, preferably as live modified viruses, and BVDV (type 1 and/or type 2), preferably attenuated BVDV (type 1 and/or type 2) [combo 131].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BRSV, BHV, and BVDV (type 1 and/or type 2), preferably attenuated BVDV (type 1 and/or type 2) [combo 132].

According to a preferred embodiment, the combination vaccine comprises *M. bovis*, preferably the attenuated and avirulent *M. bovis* as described herein, and at least one antigen each of IBR, PI-3, BRSV, BHV, preferably as live modified viruses, and BVDV (type 1 and/or type 2), preferably attenuated BVDV (type 1 and/or type 2) [combo 133].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida* and BRSV [combo 134]. According to a preferred embodiment, the combination vaccine comprises *M. bovis*, preferably the attenuated and avirulent *M. bovis* as described herein, and at least one antigen each of *Pasteurella haemolytica, Pasteurella multocida* and BRSV [combo 135].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica, Pasteurella multocida* and BRSV [combo 136]. According to a preferred embodiment, the combination vaccine comprises *M. bovis*, preferably the attenuated and avirulent *M. bovis* as described herein, and at least one antigen each of IBR, preferably as live modified viruses, *Pasteurella haemolytica, Pasteurella multocida* and BRSV [combo 137].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica, Pasteurella multocida* and BRSV [combo 138]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica, Pasteurella multocida* and BRSV [combo 139].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica, Pasteurella multocida* and BRSV [combo 140]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably as live modified viruses, *Pasteurella haemolytica, Pasteurella multocida* and BRSV [combo 141].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV, *Pasteurella haemolytica, Pasteurella multocida* and BRSV [combo 140]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV, preferably as live modified viruses, *Pasteurella haemolytica, Pasteurella multocida* and BRSV [combo 141].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida* and *H. somnus* [combo 142]. According to a preferred embodiment, the combination vaccine comprises *M. bovis*, preferably the attenuated and avirulent *M. bovis* as described herein, and at least one antigen each of *Pasteurella haemolytica, Pasteurella multocida* and *H. somnus* [combo 143].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica, Pasteurella multocida* and *H. somnus* [combo 144]. According to a preferred embodiment, the combination vaccine comprises *M. bovis*, preferably the attenuated and avirulent *M. bovis* as described herein, and at least one antigen each of IBR, preferably as live modified virus, *Pasteurella haemolytica, Pasteurella multocida* and *H. somnus* [combo 145].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica, Pasteurella multocida* and *H. somnus* [combo 146]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica, Pasteurella multocida* and *H. somnus* [combo 147].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica, Pasteurella multocida* and *H. somnus* [combo 148]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), preferably as live modified viruses, and *Pasteurella haemolytica, Pasteurella multocida* and *H. somnus* [combo 149].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV, *Pasteurella haemolytica, Pasteurella multocida* and *H. somnus* [combo 150]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), BHV, preferably as live modified viruses, *Pasteurella haemolytica, Pasteurella multocida* and *H. somnus* [combo 151].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises immunologically active components effective for the treatment and/or prophylaxis of infections caused by one or more pathogenic species of *Leptospira*, preferably selected from the group consisting of *Leptospira canicola, Leptospira grippotyphosa, Leptospira borgpetersenii, Leptospira hardjo, Leptospira prajitno, Leptospira icterohaemmorrhagiae, Leptospira bovis, Leptospira interrogans* and *Leptospira pomona* [combo 152]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises one or more antigens each of one or more specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 153].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises an immunologically active component effective for the treatment and/or prophylaxis of infections caused by *Campylobacter fetus* [combo 154]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises antigen of *Campylobacter fetus* [combo 155].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises an immunologically active component effective for the treatment and/or prophylaxis of infections caused by one or more pathogenic specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*, and *Campylobacter fetus* [combo 156]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises one or more antigen each of *Campylobacter fetus* and of one or more specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*, and. [combo 157].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Clostridium perfringens*, preferably Types A, C and/or D [combo 158]. According to a preferred embodiment, the combination vaccine comprises *M. bovis*, preferably the attenuated and avirulent *M. bovis* as described herein, and toxins of *Clostridium perfringens* Types C and D [combo 254]. According to a more preferred embodiment, said vaccine comprises antigens, preferably toxins, of *Clostridium perfringens*, preferably Types A, B, C, and/or D [combo 159].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises an immunologically active component effective for the treatment and/or prophylaxis of infections caused by infections caused by *Clostridium perfringens*, preferably Types A, C and/or D [combo 160]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium perfringens*, preferably, Types A, C, and/or D [combo 161]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium* perfringens Types, B, C, and/or D [combo 162].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium perfringens* Types A, C and/or D, and *Clostridium tetani* [combo 163]. According to a preferred embodiment, the combination vaccine comprises *M. bovis*, preferably the attenuated and avirulent *M. bovis* as described herein, and toxins of *Clostridium perfringens* Types A, C and/or D, and *Clostridium tetani* [combo 164]. According to a more preferred embodiment, said vaccine comprises antigens, preferably toxins, of *Clostridium perfringens* Types A, B, C, and/or D, and *Clostridium tetani* [combo 165].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises immunologically active components effective for the treatment and/or prophylaxis of infections caused by infections caused by *Clostridium perfringens* Types A, C and/or D, and *Clostridium tetani* [combo 166]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium perfringens* Types A, C, and/or D, and *Clostridium tetani* [combo 167]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens of *Clostridium perfringens* Types A, B, C, and/or D, and *Clostridium tetani* [combo 168].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii*, and *Clostridium perfringens* Types A, C and/or D [combo 169]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D [combo 170].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises immunologically active components effective for the treatment and/or prophylaxis of infections caused by infections caused by *Clostridium chauvoei, Clostridium septicum, Clostridium novyi, Clostridium sordellii*, and *Clostridium perfringens* Types A, C and/or D [combo 171]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens each of *Clostridium chauvoei, Clostridium septicum, Clostridium novyi, Clostridium sordellii*, and *Clostridium perfringens* Types A, C and/or D [combo 172]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens each of *Clostridium perfringens* Types, A, B, C, and/or D, *Clostridium chauvoei, Clostridium septicum, Clostridium novyi, Clostridium sordellii* and *Clostridium tetani* [combo 173].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii, Clostridium perfringens* Types A, C and/or D and BRSV [combo 174]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D and *Mycoplasma bovis* [combo 175].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii, Clostridium perfringens* Types A, C and/or D, and *H. somnus*. [combo 176]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium* septicum, *Clostridium novyi, Clostridium sordellii*, and *Clostridium perfringens* Types C and D and *H. somnus*. [combo 177].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium* septicum, *Clostridium novyi, Clostridium sordellii, Clostridium perfringens* Types A, C and/or D, BRSV, and *H. somnus* [combo 178]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D, *Mycoplasma bovis*, and *H. somnus* [combo 179].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Salmonella*, preferably *Salmonella dublin, Salmonella newport* and *Salmonella typhimurium* [combo 180]. According to a preferred embodiment, the combination vaccine comprises *M. bovis*, preferably the attenuated and avirulent *M. bovis* as described herein, and one or more toxins of *Salmonella*, preferably each of *Salmonella dublin, Salmonella newport*, and/or *Salmonella typhimurium* [combo 181].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178 and 179], that further comprises immunologically active components effective for the treatment and/or prophylaxis of infections caused by infections caused by *Salmonella*, preferably *Salmonella dublin, Salmonella newport* and *Salmonella typhimurium* [combo 182]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178 and 179], that further comprises one or more antigens, preferably toxins, of *Salmonella*, preferably each of *Salmonella dublin, salmonella newport* and/or *Salmonella typhimurium* [combo 183].

According to a preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida, Salmonella*, preferably *Salmonella dublin, Salmonella newport* and *Salmonella typhimurium* [combo 184]. According to a preferred embodiment, the combination vaccine comprises *M. bovis*, preferably the attenuated and avirulent *M. bovis* as described herein, and *Pasteurella haemolytica, Pasteurella multocida, Salmonella*, preferably *Salmonella dublin, Salmonella newport*, and *Salmonella typhimurium* Bacterin-Toxoid [combo 185]. According to more preferred embodiment, said combination vaccine comprises multiple isolates of *Pasteurella haemolytica* Type A1 and an associated toxoid fraction, and single isolates of *P. multocida, S. dublin*, and *S. typhimurium* [combo 186].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Moraxella bovis* and/or *Klebsiella* spp., preferably *Klebsiella pneumoniae* [combo 187]. According to a preferred embodiment, the combination vaccine comprises *M. bovis*, preferably the attenuated and avirulent *M. bovis* as described herein, and one or more toxins each of *Moraxella bovis* and/or *Klebsiella* spp. preferably *Klebsiella pneumoniae* [combo 188].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, and 186], that further comprises immunologically active components effective for the treatment and/or prophylaxis of infections caused by infections caused by *Moraxella bovis* and/or *Klebsiella* spp., preferably *Klebsiella pneumoniae* [combo 189]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 163, 164, 165, 169, 170, 174, 175, 176, 177, 178, 179, 180, 181, 184, 185 and 186], that further comprises one or more antigens, preferably toxins, each of *Moraxella bovis* and/or *Klebsiella* spp., preferably, *Klebsiella pneumoniae* [combo 190].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Escherichia coli* [combo 191]. According to a preferred embodiment, the combination vaccine comprises *M. bovis*, preferably the attenuated and avirulent *M. bovis* as described herein, and one or more toxins of *Escherichia coli* [combo 192].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and 190], that further comprises an immunologically active component effective for the treatment and/or prophylaxis of infections caused by infections caused by *Escherichia coli* [combo 193]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and 190], that further comprises antigen, preferably a toxin, of *Escherichia coli* [combo 194].

According to a preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida, Salmonella dublin, Salmonella typhimurium* and *Escherichia coli* [combo 195]. According to a preferred embodiment, the combination vaccine comprises *M. bovis*, preferably the attenuated and avirulent *M. bovis* as described herein, and one or more antigens each of *Pasteurella haemolytica, Pasteurella multocida, Salmonella dublin, Salmonella typhimurium* and *Escherichia coli* Bacterin-Toxoid [combo 196]. According to more preferred embodiment, said combination vaccine comprises multiple isolates of *Pasteurella haemolytica* Type A1 and an associated toxoid fraction, and single isolates of *P. multocida, S. dublin*, and *S. typhimurium* [combo 197].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by bovine Rotavirus [combo 198]. According to a preferred embodiment, the combination vaccine comprises *M. bovis*, preferably the attenuated and avirulent *M. bovis* as described herein and antigen of bovine Rotavirus [combo 199].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 195, 196, and 197], that further comprises an immunologically active component effective for the treatment and/or prophylaxis of infections caused by infections caused by bovine Rotavirus [200]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises antigen of bovine Rotavirus [combo 201].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by bovine Coronavirus [combo 202]. According to a preferred embodiment, the combination vaccine comprises *M. bovis*, preferably the attenuated and avirulent *M. bovis* as described herein, and antigen of bovine Coronavirus [combo 203].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises an immunologically active component effective for the treatment and/or prophylaxis of infections caused by infections caused by bovine Coronavirus [combo 204]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, and 197], that further comprises antigen of bovine Coronavirus [combo 205].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein and further immunologically active components effective for the treatment and/or prophylaxis of infections caused by bovine Coronavirus and bovine Rotavirus [combo 206]. According to a preferred embodiment, the combination vaccine comprises *M. bovis*, preferably the attenuated and avirulent *M. bovis* as described herein and one or more antigens each of bovine Coronavirus and bovine Rotavirus [combo 207].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises immunologically active components effective for the treatment and/or prophylaxis of infections caused by infections caused by bovine Coronavirus and bovine Rotavirus [combo 208]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, and 197], that further comprises one or more antigens each of bovine Coronavirus and bovine Rotavirus [combo 209].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Cryptosporidium parvum* [combo 210]. According to a preferred embodiment, the combination vaccine comprises *M. bovis*, preferably the attenuated and avirulent *M. bovis* as described herein, and antigen of *Cryptosporidium parvum* [combo 211].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises an immunologically active component effective for the treatment and/or prophylaxis of infections caused by infections caused by *Cryptosporidium parvum* [combo 212]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises antigen of *Cryptosporidium parvum* [combo 213].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Cryptosporidium hominis* [combo 214]. According to a preferred embodiment, the combination vaccine comprises *M. bovis*, preferably the attenuated and avirulent *M. bovis* as described herein, and antigen of *Cryptosporidium hominis* [combo 215].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises an immunologically active component effective for the treatment and/or prophylaxis of infections caused by infections caused by *Cryptosporidium hominis* [combo 216]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises antigen of *Cryptosporidium hominis* [combo 217].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Cryptosporidium parvum* and *Cryptosporidium hominis* [combo 218]. According to a preferred embodiment, the combination vaccine comprises *M. bovis*, preferably the attenuated and avirulent *M. bovis* as described herein, and one or more antigens each of *Cryptosporidium parvum* and *Cryptosporidium hominis* [combo 219].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises immunologically active components effective for the treatment and/or prophylaxis of infections caused by infections caused by *Cryptosporidium parvum* and *Cryptosporidium hominis* [combo 220]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises one or more antigens each of *Cryptosporidium parvum* and *Cryptosporidium hominis* [combo 221].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Mycobacterium avium paratuberculosis* [combo 222]. According to a preferred embodiment, the combination vaccine comprises *M. bovis*, preferably the attenuated and avirulent *M. bovis* as described herein, and antigen of *Mycobacterium avium paratuberculosis* [combo 223].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221], that further comprises an immunologically active component effective for the treatment and/or prophylaxis of infections caused by infections caused by *Mycobacterium avium paratuberculosis* [combo 224]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220 and 221], that further comprises antigen of *Mycobacterium avium paratuberculosis* [combo 225].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by Adenovirus [combo 226]. According to a preferred embodiment, the combination vaccine comprises *M. bovis*, preferably the attenuated and avirulent *M. bovis* as described herein, and antigen of Adenovirus [combo 227].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224 and 225], that further comprises an immunologically active component effective for the treatment and/or prophylaxis of infections caused by infections caused by Adenovirus [combo 228]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, and 225], that further comprises antigen of Adenovirus [combo 229].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by Astrovirus [combo 230]. According to a preferred embodiment, the combination vaccine comprises *M. bovis*, preferably the attenuated and avirulent *M. bovis* as described herein, and antigen of Astrovirus [combo 231].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228 and 229], that further comprises an immunologically active component effective for the treatment and/or prophylaxis of infections caused by infections caused by Astrovirus [combo 232]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228 and 229], that further comprises antigen of Astrovirus [combo 233].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by bovine Parvovirus [combo 234]. According to a preferred embodiment, the combination vaccine comprises *M. bovis*, preferably the attenuated and avirulent *M. bovis* as described herein, and antigen of bovine Parvovirus [combo 235].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232 and 233], that further comprises an immunologically active component effective for the treatment and/or prophylaxis of infections caused by infections caused by bovine Parvovirus [combo 236]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, and 233], that further comprises antigen of bovine Parvovirus [combo 237].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Cryptosporidium parvum*, Adenovirus, Astrovirus, bovine Parvovirus and *Mycobacterium avium paratuberculosis* [combo 238]. According to a preferred embodiment, the combination vaccine comprises *M. bovis*, preferably the attenuated and avirulent *M. bovis* as described herein, and one or more antigens each of *Cryptosporidium parvum*, Adenovirus, Astrovirus, bovine Parvovirus and *Mycobacterium avium paratuberculosis* [combo 239].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Escherichia coli, Salmonella* spp., preferably *Salmonella dublin, Salmonella typhimurium* and *Salmonella newport*, bovine Rotavirus and bovine Coronavirus, *Cryptosporidium parvum*, Adenovirus, Astrovirus, bovine Parvovirus and *Mycobacterium avium paratuberculosis* [combo 240]. According to a preferred embodiment, the combination vaccine comprises *M. bovis*, preferably the attenuated and avirulent *M. bovis* as described herein, and one or more antigens each of *Escherichia coli, Salmonella* spp., preferably *Salmonella dublin, Salmonella typhimurium* and *Salmonella newport*, bovine rotavirus and bovine Coronavirus, *Cryptosporidium parvum*, Adenovirus, Astrovirus, bovine Parvovirus and *Mycobacterium avium paratuberculosis* [combo 241].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus uberis* and/or *Streptococcus dysgalactiae* [combo 242]. According to a preferred embodiment, the combination vaccine comprises *M. bovis*, preferably the attenuated and avirulent *M. bovis* as described herein, and antigen of *Streptococcus* spp., preferably each of *Streptococcus uberis* and/or *Streptococcus dysgalactiae*, [combo 243]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae* [combo 244].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus uberis* and/or *Streptococcus dysgalactiae* and/or *Staphylococcus aureus* [combo 245]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae*, and/or *Staphylococcus aureus* [combo 246].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, and 241], that further comprises immunologically active components effective for the treatment and/or prophylaxis of infections caused by infections caused by *Streptococcus* spp., preferably *Streptococcus uberis* and/or *Streptococcus dysgalactiae*, and/or *Staphylococcus aureus* [combo 247]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240 and 241], that further comprises one or more antigens each of *Streptococcus* spp., preferably *Streptococcus uberis* and/or *Streptococcus dysgalactiae*, and/or *Staphylococcus aureus* [combo 248]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240 and 241], that further comprises one or more antigens of several serotypes of *Streptococcus* spp., preferably of several serotypes each of *Streptococcus uberis* and/or *Streptococcus dysgalactiae*, and/or *Staphylococcus aureus* [combo 249].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus uberis, Streptococcus dysgalactiae* and/or *Staphylococcus aureus, Klebsiella* spp. and *Mycoplasma* spp. [combo 250]. According to a preferred embodiment, the combination vaccine comprises *M. bovis*, preferably the attenuated and avirulent *M. bovis* as described herein, and one or more antigens of *Streptococcus* spp., preferably each of *Streptococcus uberis, Streptococcus dysgalactiae*, and/or *Streptococcus aureus, Klebsiella* spp. and *Mycoplasma* spp. [combo 251]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae, Staphylococcus aureus, Klebsiella* spp., *Mycoplasma* spp. and endotoxin [combo 252].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 253]. According to a preferred embodiment, the combination vaccine comprises *M. bovis*, preferably the attenuated and avirulent *M. bovis* as described herein, and one or more antigens each of *Trichophyton*, and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 254].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, and 251], that further comprises immunologically active components effective for the treatment and/or prophylaxis of infections caused by infections caused by *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 255]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, and 252], that further comprises one or more antigens each of *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 256].

According to a further aspect, the present invention also relates to the combined use or co-administration of any of the antigens provided in the combination vaccines [combo 1 to combo 256]. Preferably, the *M. bovis* antigen is provided in a first immunogenic composition, and any other antigen/antigens are provided in one or more further immunogenic compositions to be administered.

According to further embodiment, the immunologically active component(s) effective for the treatment and/or prophylaxis of infections caused by one or more cattle relevant pathogen(s) as source of the combination vaccine provided herewith is any one included in the vaccines selected from the group consisting of: ALPHA 7™, ALPHA-7/MB™, ALPHA-CD™ BAR-VAC® 7, BAR-VAC® 7/SOMNUS, BAR-VAC® 8, BAR-VAC® CD, BAR-VAC® C/DT, BREED-BACK™ FP 10, BREED-BACK™ FP 10 HS, BREED-BACK™ FP 5, BREED-BACK™ FP 5 HS, BREED-BACK-10™, CALIBER® 3, CALIBER® 7, ELITE 4™, ELITE 9™, ELITE 9-HS™, EXPRESS® 10, EXPRESS® 10-HS, EXPRESS® 3, EXPRESS® 3/Lp, EXPRESS 4®, EXPRESS® 5, EXPRESS® 5-HS, EXPRESS® 5-PHM, EXPRESS® I, EXPRESS® I/LP, OCU-GUARD® MB, PULMO-GUARD™ MpB, PULMO-GUARD™ PH-M, PULMO-GUARD™ PH-M/SDT, PULMO-GUARD™ PHM-1, TETGUARD™, VIBRIO-LEPTO-5™ (all of Boehringer Ingelheim, St. Joseph, Mo.); COBALT™7, I-SITE™, LEPTO 5, MASTER GUARD® PREG 5, MASTER GUARD® 10, MASTER GUARD® 10+VIBRIO, MASTER GUARD® J5, P.H.M. BAC® 1, PRE-VENT 6™, RESPROMUNE® 4, RESPROMUNE® 4+SOMNUMUNE® (IM, SC), RESPROMUNE® 5 I-B-P+BRSV, RESPROMUNE® 5+L5, RESPROMUNE® 5+L5 SOMNUS, RESPROMUNE® 5+SOMNUMUNE, RESPROMUNE® 5+VL5, RESPROMUNE® 8, RESPROMUNE® 9, RESPROMUNE® 10, SCOUR VAC™ 4, SCOUR VAC™ 9, SCOUR VAC™ E. COLI+C, SOMNUMUNE®, TITANIUM™ 3, TITANIUM™ 4, TITANIUM™ 4 L5, TITANTIUM™ 5, TITANIUM™ 5 L5, TITANIUM™ 5+P.H.M. BAC®-1, TITANIUM™ BRSV 3, TITANIUM™ IBR, TITANIUM™ IBR-LP (all of Agri Laboratories Inc., St. Joseph, Mo.); HERD-VAC® 3, HERD-VAC® 3 S, HERD-VAC® 8, HERD-VAC® 9, SURROUND™ 4, SURROUND™ 4+HS, SURROUND™ 8, SURROUND™ 9, SURROUND™ 9+HS, SURROUND™ HS, SURROUND™ L5, SURROUND™ V-L5 (all of BioCor, Omaha, Nebr. (Pfizer)); MYCOMUNE® (Biomune Co., Lenexa, Kans.); Bluetongue vaccine, Bovine Virus Diarrhea Vaccine, *Campylobacter fetus* bacterin-bovine, ESSENTIAL 1™, ESSENTIAL 2™, ESSENTIAL 2+P™, ESSENTIAL 3™, ESSENTIAL 3+T™, ESSENTIAL 4™, LEPTO-5™, *Mannheimia haemolytica-Pasteurella multocida* bacterin, PRE-BREED 6™, PRE-BREED 8™, RESPIRA-1™, RESPIRA-3™, Wart Vaccine (all of Colorado Serum Company, Denver, Colo.); PYRAMID® 3, PYRAMID® 4, PYRAMID® 4+PRESPONSE® SQ, PYRAMID® 5, PYRAMID® 8, PYRAMID® 9, PYRAMID® IBR, PYRAMID® IBR LEPTO, TRIANGLE® 1+Type II BVD, TRIANGLE® 3+VL5, TRIANGLE® 4+HS, TRIANGLE® 4+PH/HS, TRIANGLE® 4+PH-K, TRIANGLE® 4+TYPE II BVD, TRIANGLE® 9+HS, TRIANGLE® 9+PH-K, TRIANGLE®+Type II BVD, TRICHGUARD®, TRICHGUARD®+V5L, TRIVIB 5L® (all of Fort Dodge Animal Health, Overland Park, Kans. (Wyeth)); J-5 *Escherichia coli* Bacterin, Serpens Species Bacterin; *Staphylococcus aureus* bacterin-toxoid (all of Hygieia Biological Laboratories, Woodland, Calif.); ENDOVAC-BOVI® with IMMUNEPLUS® (Immvac, Inc., Columbia, Mo.); 20/20 VISION® with SPUR®, L5 SQ, NEOGUARD™, MASTERGUARD® PREG 5, ONCE PMH®, ONCE PMH® SQ, VIBRALONE™-L5, VISION® 7 SOMUNUS WITH SPUR®, VISION® 7 WITH SPUR®, VISION® 8 SOMNUS WITH SPUR®, VISION® 8 WITH SPUR®, VISION® CD-T WITH SPUR®, VISION® CD WITH SPUR®, VISTA™ IBR SQ, VISTA™ 3 SQ, VISTA™ 5 SQ, VISTA™ 5 L5 SQ, VISTA™ ONCE SQ, VL5 SQ, VOLAR®, (all of Intervet Inc., Millsboro, Del.); VAC®, RELIANT® 3, RELIANT® 4, RELIANT® IBR, RELIANT® IBR/BVD, RELIANT® IBR/LEPTO, RELIANT® PLUS BVD-K (DUAL IBR™), RELIANT® PLUS (DUAL IBR™), RESPISHIELD™ 4, RESPISHIELD™ 4 L5, RESPISHIELD™ HM (all of Merial LTD, Duluth, Ga.); ARSENAL® 4.1, ARSENAL® IBR, ARSENAL® IBR BVD, BOVINE PILI SHIELD™, BOVINE PILI SHIELD™+C, CLOSTRI SHIELD® 7, CLOSTRI SHIELD® BCD, FUSOGARD®, LEPTO SHIELD™ 5, PINKEYE SHIELD™ XT4, SALMO SHIELD® T, SALMO SHIELD® TD, SCOUR BOS™ 4, SCOUR BOS™ 9, SOMNU SHIELD™, TREP SHIELD™ HW, VIB SHIELD® L5, VIB SHIELD® Plus, VIB SHIELD® PLUS L5, VIRA SHIELD® 2, VIRA SHIELD® 2+BRSV, VIRA SHIELD® 3, VIRA SHIELD® 3+VL5, VIRA SHIELD® 4, VIRA SHIELD® 4+L5, VIRA SHIELD® 5, VIRA SHIELD® 5+L5, VIRA SHIELD® 5+L5 SOMNUS, VIRA SHIELD® 5+SOMNUS, VIRA SHIELD® 5+VL5, VIRA SHIELD® 5+VL5 SOMNUS, VIRA SHIELD® 6, VIRA SHIELD® 6+SOMNUS, WART SHIELD™ (all of Novartis Animal Health, Basel, Switzerland); BOVI-K® 4, BOVI-SHIELDBOVI-SHIELD® 3, BOVI-SHIELD® 4, BOVI-SHIELD™ BRSV, BOVI-SHIELD® FP™ 4+L5, BOVI-SHIELD® GOLD 3, BOVI-SHIELD® GOLD 5, BOVI-SHIELD® GOLD FP™ 5 L5, BOVI-SHIELD® GOLD FP™ 5 VL5, BOVI-SHIELD® Gold IBR-BVD, BOVI-SHIELD® Gold IBR-BVD-BRSV-LP, BOVI-SHIELD™ IBR, BOVI-SHIELD™ IBR-BRSV-LP, BOVI-SHIELD™ IBR-BVD, BOVI-SHIELD™ IBR-BVD-BRSV-LP, BOVI-SHIELD™ IBR-PI3-BRSV, CALF-GUARD®, CATTLE-MASTER® 4, CATTLEMASTER® 4+L5, CATTLEMASTER® 4+VL5, CATTLEMASTER® BVD-K, CATTLEMASTER® Gold FP™ 5, CATTLEMASTER® Gold FP™ 5 L5, DEFENSOR® 3, FORTRESS® 7, FORTRESS® 8, FORTRESS® CD, LEPTOFERM®-5, ONE SHOT®, ONE SHOT ULTRA™ 7, ONE SHOT ULTRA™ 8, PREGGUARD™ FP 9, PREGGUARD® Gold FP™ 10, RESVAC® BRSV/SOMUBAC®, RESVAC® 4/SOMUBAC®, SCOURGUARD 3® (K), SCOURGUARD 3® (K)/C, SOMUBAC®, SPIROVAC®, SPIROVAC® L5, SPIROVAC® VL5, STAYBRED™ VL5, TSV-2™, ULTRABAC® 7, ULTRABAC® 7/SOMUBAC®, ULTRABAC®8, ULTRABAC® CD, ULTRACHOICE™ 7, ULTRACHOICE™ 8, ULTRACHOICE™ CD, UPJOHN J-5 BACTERIN™, VIBRIN® (all of Pfizer Inc., New York, N.Y.); COVEXIN® 8 VACCINE, ELECTROID® 7 VACCINE, ELECTROID® D, GUARDIAN™, JENCINE® 2, JENCINE® 3, JENCINE® 4, NASALGEN® IP, VACCINE, PILIGUARD® PINKEYE-1 TRIVALENT, PILIGUARD® PINKEYE+7, PILIGUARD® PINKEYE TRIVIEW®, SITEGUARD® G, SITEGUARD® MLG VACCINE (all of Schering-Plough Animal Health Corporation, Kenilworth, N.J.); MYCO-BAC™ B, POLY-BAC B® 3, POLY-BAC B® SOMNUS, SUPER POLY-BAC B® SOMNUS (all of Texas Vet Lab, Inc., San Angelo, Tex.), VIRABOS™-3 with IMMUNOSTIM®, VIRABOS™-4+H. SOMNUS with IMMUNOSTIM®, and VIRABOS™-4 with IMMUNOSTIM® (all of Bioniche Animal Health, Athens, Ga.), wherein the *M. bovis* antigen, preferably the attenuated, avirulent *M. bovis* as described herein, is added. Alternatively, when *M. bovis* antigen is present in any of those vaccines, attenuated avirulent *M. bovis*, as described herein, is added, or the *M. bovis* antigen present any of those vaccines is substituted by the attenuated, avirulent *M. bovis* as described herein.

Dose and Administration

According to the present invention, an effective amount of a combination vaccine administered to cattle provides effective immunity against microbiological infections caused by *M. bovis* and at least one further pathogen as listed above. Preferred combinations of antigens for the treatment and prophylaxis of microbiological diseases in cattle are listed above.

In preferred forms, the dose volume of the combination vaccine as well as of each immunogenic composition when separately co-administered is no more than 5 ml, more preferably no more than 3 ml, and more preferably no more than 2 ml. In a most preferred embodiment, the dose is 2 ml, preferably administered intranasally, with 1 ml being administered in each nostril, more preferably administered intramuscularly, even more preferably administered subcutaneously, and most preferably administered both intranasally and subcutaneously on one occasion as a single dose. In some preferred forms, a second or subsequent administration of the immunogenic composition would be administered after the first administration. Such a subsequent administration would preferably occur at least 10 days after the initial administration, more preferably between at least 10-32 days, more preferably between at least 12-30 days, still more preferably at least 14 days, and most preferably between at least 14-28 days. In most preferred forms, the vaccine would be administered either as a single dose, preferably on Day 0 or, in alternative forms, 14-28 days thereafter, preferably on Day 0 and 14-28 days thereafter with exposure to pathogenic forms of *M. bovis* not occurring until after the completion of the immunizing regimen. In a most preferred form, no booster is necessary and the vaccine is administered only one time. The vaccine is administered to animals from 1 day of age through adulthood, preferably to calves from 1 day of age through young adult cattle 2 years of age, more preferably to calves from 1 day of age through 16 weeks of age, and most preferably to calves from 6 weeks to 12 weeks of age. Such administration lessened or reduced signs of *M. bovis* infection as described below. Preferably, signs of *M. bovis* infection in the group vaccinated as described above are reduced by at least 50%, more preferably at least 60%, even more preferably at least 70%, and even more preferably at least 75% in comparison to the non-vaccinated group. Lung pathology assessment, specifically the percentage of lung consolidation attributed to lesions due to *M. bovis*, as customarily scored for various species, was made post-necropsy. Preferably lung lesions are reduced by at least 33%, more preferably at least 50%, even more preferably at least 70%, even more preferably at least 80%, even more preferably at least 90%, and most preferably by at least 95% in comparison to a non-vaccinated group.

The amount of combination vaccine that is effective depends on the ingredients of the vaccine and the schedule of administration. Typically, when bacterial antigen is used in the combination vaccine or in a combined use, the vaccine or immunogenic composition contains an amount of about $10^3$ to about $10^{10}$ colony forming units (CFU) of the bacterial antigen per dose, preferably, about $10^4$ to about $10^9$ CFU of the bacterial antigen per dose, more preferably about $10^5$ to about $10^6$ CFU of the bacterial antigen per dose. For instance, the attenuated, avirulent *M. bovis* is preferably used in amounts of about $10^2$ to about $10^{10}$ CFU per dose, preferably about $10^3$ to about $10^9$ CFU per dose, even more preferably in an amount of about $10^8$ to about $10^{10}$ CFU per dose, most preferably in an amount of about $2.1\times10^9$ CFU per dose.

Typically, when an inactivated virus or a modified live virus preparation is used in the combination vaccine or in a combined use, the vaccine or immunogenic composition containing about $10^2$ to about $10^9$ $TCID_{50}$ viral antigen per dose, preferably about $10^3$ to about $10^8$ $TCID_{50}$ viral antigen per dose, more preferably, about $10^4$ to about $10^8$ $TCID_{50}$ viral antigen per dose. For example, about $10^5$ to about $10^8$ $TCID_{50}$ per dose of attenuated BVDV (types 1 and 2) is effective when administered twice to the animal during a period of about 3 to 4 weeks. In general, inactivated antigen is normally used in higher amounts than live modified viruses.

In the event the combination vaccine comprises live modified IBR, the amount of IBR antigen is preferably in a range of about $10^5$ to $10^{7.5}$ $TCID_{50}$ per dose. In the event the combination vaccine comprises live modified PI3, the amount of PI3 antigen is preferably in a range of about $10^7$ to $10^9$ $TCID_{50}$ per dose. In the event the combination vaccine comprises live modified BRSV, the amount of BRSV antigen is preferably in a range of about $10^{4.5}$ to $10^{6.5}$ $TCID_{50}$ per dose. In the event the combination vaccine comprises killed antigens the $TCID_{50}$ or CFU indicates the amount of antigen per dose in the live culture before inactivation, and for IBR, the amount of IBR antigen is preferably in a range of about $10^{7.0}$ to $10^{9.0}$ $TCID_{50}$ per dose. In the event the combination vaccine comprises killed PI3, the amount of PI3 antigen is preferably in a range of about $10^{7.2}$ to $10^{9.2}$ $TCID_{50}$ per dose. In the event the combination vaccine comprises killed BRSV, the amount of BRSV antigen is preferably in a range of about $10^{5.0}$ to $10^{7.5}$ $TCID_{50}$ per dose. In the event the combination vaccine comprises killed *Leptospira* spp. the amount of each *Leptospira* spp. antigen is preferably in a range of about $10^{7.0}$ to $10^{10}$ (CFU) per dose. In the event the combination vaccine comprises killed *H. somnus*, and/or killed *Pasteurella multocida*, and/or killed *Mannheimia haemolytica* the amount of *H. somnus* antigen and/or *Pasteurella multocida* antigen, and/or *Mannheimia haemolytica* antigen is preferably in a range of about $10^{6.0}$ to $10^{10}$ colony forming unit (CFU) per dose.

Combined Use/Method of Treatment

A further aspect of the present invention relates to the combined use of immunogenic compositions for the treatment and/or prophylaxis of cattle against microbiological infections, wherein the infections are caused by *M. bovis* and at least one further cattle relevant pathogen.

Yet another important embodiment of the invention is a method for the prophylaxis or treatment of diseases caused by *M. bovis*, and further cattle pathogenic microorganism(s), wherein a *M. bovis* antigen, preferably the attenuated, avirulent *M. bovis* as described herein, and further immunologically active components effective for the treatment and/or prophylaxis of the infection caused by said further cattle pathogenic microorganism, preferably as described herein, are administered to an animal in need thereof at a suitable dose, as known to the skilled person.

The combined use or the method of co-administration of two or more antigens of pathogens affecting cattle comprises administering a first immunogenic composition comprising a *M. bovis* antigen, preferably the attenuated, avirulent *M. bovis* as provided herewith, and at least one further immunogenic composition comprising an immunologically active component effective for the treatment and/or prophylaxis of infections caused by a further pathogen of cattle. Preferably, the further pathogen is one of the pathogens as listed herein. Preferably, the first and the further immunogenic compositions are administered separately. Preferably, the further immunogenic composition comprises one or more immunologically active component(s) effective for the treatment and/or prophylaxis of infections caused by a pathogen of cattle other than *M. bovis*. More preferably, the first and the further immunogenic compositions are administered together by means such as mixing before administration and/or by formulating the first and the further immunogenic compositions in a single container.

The co-administration of each of the immunogenic compositions occurs simultaneously, which means at least within 48 hours, preferably within 24 hours, even more preferably within 12 hours, even more preferably within 6 hours, even more preferably within 3 hours, even more preferably within 2, hours, even more preferably within 1 hour. The route of administration of each of the immunogenic compositions depends on the mode-of-action and may be the same, but also could be different.

According to a further embodiment the *M. bovis* antigen as provided herewith and one or more further immunologically active component(s) effective for the treatment and/or prophylaxis of infections caused by a further cattle relevant pathogen other than *M. bovis* can be used a medicament. Preferably, that medicament is a vaccine and can be used for lessening or reducing the signs of a *M. bovis* infection. Most preferably, that medicament or vaccine can be used for lessening or reducing the signs of a *M. bovis* infection and associated with or caused by an infection of the further cattle relevant antigen.

Formulations

A further aspect of the present invention is the preparation of the combination vaccine(s). One of skill in the art can determine additional components which are present in the composition of the invention. (see also Remington's Pharmaceutical Sciences, (1990) 18th ed. Mack Publ., Easton). Known injectable, physiologically acceptable sterile solutions may be used. For preparing a ready-to-use solution for parenteral injection or infusion, aqueous isotonic solutions, such as e.g. saline or corresponding plasma protein solutions, are readily available. The pharmaceutical compositions of the present invention may be present as lyophylisates or dry preparations, which can be reconstituted with a known injectable solution directly before use under sterile conditions, e.g. as a kit of parts.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

Adjuvants include, but are not limited to, the RIBI adjuvant system (Ribi Inc.), alum, aluminum hydroxide gel, Cholesterol, oil-in water emulsions, water-in-oil emulsions such as, e.g., Freund's complete and incomplete adjuvants, Block copolymer (CytRx, Atlanta Ga.), SAF-M (Chiron, Emeryville Calif.), CARBOPOL®, AMPHIGENO adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others.

The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, preferably the composition comprises from about 50 ug to about 2000 ug of adjuvant and preferably about 250 ug/ml dose of the vaccine composition. In another preferred embodiment, the present invention an antibiotic is present in an amount of from about 1 ug/ml to about 60 ug/ml of and preferably less than about 30 ug/ml. According to a further embodiment the combination vaccine (or immunogenic composition) is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

According to a further embodiment, the immunogenic composition or combination vaccine as provided herewith, which comprises at least one *M. bovis* antigen and one or more further immunologically active component(s) effective for the treatment and/or prophylaxis of infections caused by a further cattle relevant pathogen other than *M. bovis* are formulated as fix-dose combination vaccine. Preferably, the immunogenic composition or combination vaccine provided herewith, in particular the fix-dose combination vaccine is formulated for use as a single-dose or multi-dose vaccine, whereas the formulation for use as a single-dose vaccine is most preferred. In other words the immunogenic compositions or vaccine, preferably the fix-dose combination vaccine provided herewith is formulated for the administration as a multi-dose or single-dose, whereas the formulation for the administration as single-dose is most preferred. As shown in the example section, such a single dose administration of the *M. bovis* antigen is effective in lessening or reducing the signs of an *M. bovis* infection. Thus, according to a further embodiment, the immunogenic compositions provided herewith, in particular the fix-dose combination vaccine is formulated for use as a single-dose vaccine, wherein the administration of such single-dose is effective in lessening or reducing the signs of an *M. bovis* infection.

Modes of Administration and Dosing

Compositions of the present invention may be administered in any conventional manner. Examples of administration methods include any that afford access by cells of the immune system to the immunogenic composition, including but not limited to, oral, transdermal, intradermal, intravenous, subcutaneous, intramuscular, intraocular, intraperitoneal, intrarectal, intravaginal, intranasal, intragastrical, intratracheal, intrapulmonarial, or any combination thereof. Preferred modes of administration are intramuscular, subcutaneous and intranasal, with subcutaneous and intranasal being especially preferred. If desired or necessary, booster immunizations may be given once or several times at various intervals. However, it is a preferred embodiment of the present invention that the vaccination be administered as a single-dose. After administration of such a vaccine, an immune response is elicited in the animal and signs of *M. bovis* infection are reduced in incidence and/or severity, as well as a reduction in rate of mortality, in comparison to animals exposed to wild-type bacteria or isolates after challenge with a virulent form of *M. bovis*.

In preferred forms, the dose volume of the vaccine is no more than 5 ml, more preferably no more than 3 ml, and more preferably no more than 2 ml. In a most preferred embodiment, the dose would be 2 ml, preferably administered intranasally, with 1 ml being administered in each nostril, even more preferably administered subcutaneously, and most preferably administered both intranasally and subcutaneously on one occasion as a single dose. In some preferred forms, a second or subsequent administration of the immunogenic composition would be administered after the first administration.

Such a subsequent administration would preferably occur at least 10 days after the initial administration, more preferably between at least 10-32 days, more preferably between at least 12-30 days, still more preferably at least 14 days, and most preferably between at least 14-28 days. In most preferred forms, the vaccine would be administered either on Day 0 as a single dose, or, in alternative forms, on Day 0 and 14-28 days thereafter with exposure to pathogenic forms of *M. bovis* not occurring until after the completion of the immunizing regimen. In a most preferred form, no booster is necessary and the vaccine is administered only one time. The vaccine is administered to animals from 1 day of age through adulthood, preferably to calves from 1 day of age through young adult cattle 2 years of age, more preferably to calves from 1 day of age through 16 weeks of age, and most preferably to calves from 6 weeks to 12 weeks of age. Such administration reduced signs of *M. bovis* infection as described below. In fact, the studies herein show that signs of *M. bovis* infection in the group vaccinated as described above were reduced by at least 50%, more preferably, at least 60%, even more preferably, at least 70%, even more preferably, at least 75%, more preferably, at least 80%, still more preferably at least 83%, more preferably, at least 85%, and, most preferably, at least 90% in comparison to the non-vaccinated group.

In a preferred embodiment, the immunogenic compositions of the present invention are effective in stimulating an onset of immunity within 14 days following a single dose administration. In an additionally preferred embodiment the immunogenic composition of the present invention is effective in stimulating duration of immunity of at least 42 days following a single dose administration of the immunogenic composition.

In another preferred embodiment, the immunogenic compositions of the present invention may be co-administered to an animal (preferably cattle). Specifically two or more antigens may be administered to an animal of the *M. bovis* antigen of the present invention and at least one other immunologically active component(s) effective for the treatment and/or prophylaxis of infections caused by a further cattle relevant pathogen other than *M. bovis* (discussed in more detail infra). The *M. bovis* antigen of the present invention and the immunologically active component(s) may be co-administered or administered separately. An example of separate co-administration includes the *M. bovis* antigen and the immunologically active component(s) occurring within 2 days. Alternatively, the *M. bovis* antigen and one or more immunologically active component(s) may be formulated as fix-dose combination vaccine. Another preferred embodiment would be administering the two or more antigens which comprise *M. bovis* antigen and one or more immunologically active component(s) effective for the treatment and/or prophylaxis of infections caused by a further cattle relevant pathogen other than *M. bovis* are in one only dose. Alternatively two, three, or four doses may be administered that is, co-administered or administered separately.

In a preferred embodiment, the immunogenic composition of the present invention contains an adjuvant. Adjuvants may include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion may be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997), hereby entirely incorporated by reference. For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996, hereby entirely incorporated by reference). Persons skilled in the art may also refer to U.S. Pat. No. 2,909,462 (hereby entirely incorporated by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

Preferably, the adjuvant is added in an amount of about 100 μg to about 1 g per dose. Even more preferably the adjuvant is added in an amount of about 100 μg to about 500 mg per dose. Even more preferably the adjuvant is added in an amount of about 500 μg to about 250 mg per dose. Even more preferably the adjuvant is added in an amount of about 750 μg to about 100 mg per dose. Even more preferably the adjuvant is added in an amount of about 1 mg to about 50 mg per dose. Even more preferably the adjuvant is added in an amount of about 1 mg to about 10 mg per dose. Most preferably the adjuvant is added in an amount of about 1 mg per dose.

Carriers

In addition, the immunogenic and vaccine compositions of the present invention may include one or more veterinary-acceptable carriers. Thus, the present invention relates to the use of an *M. bovis* strain, attenuated through multiple passage or serial attenuation as described above, as a medicine, preferably as a veterinary medicine. *M. bovis* strains attenuated as described above may be used for the preparation of a pharmaceutical composition, as described herein, for the prophylaxis or treatment of infections caused by *M. bovis*. As noted above, those pharmaceutical compositions/vaccine compositions may be used for the treatment and/or prophylaxis of animals susceptible to infection by *M. bovis.*

Methods of Treatment or Prophylaxis

In another aspect of the present invention, the invention is a method for the treatment or prophylaxis including a lessening of the incidence of wild type infection in a herd or reduction in the severity of signs of *M. bovis* infection associated with wild type *M. bovis* infected animals administered immunogenic compositions in accordance with the present invention in comparison to animals that are either not vaccinated or vaccinated with vaccines available prior to the present invention is provided. Additionally, administration of the vaccine in accordance with the present invention reduces the number of animals in a herd that become infected with *M. bovis*. Such a method generally involves the administration of a therapeutically effective amount of an *M. bovis* strain attenuated through the methods disclosed above, to a subject or herd of subjects in need of such a treatment. Preferably, clinical symptoms are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to animals that are either not vaccinated or vaccinated with an *M. bovis* immunogenic composition that was available prior to the present invention but subsequently infected by wild-type *M. bovis.*

EXAMPLES

The following examples are provided for the purposes of illustration and are not intended to limit the scope of the present invention

Example 1

Preparation and Testing of a High-Passage *M. bovis* Isolate Vaccine

Materials and Methods

Forty-four (44) calves were reared. Post-weaning, the calves were randomly assigned to 1 of 5 groups. Calves were 6±2 weeks of age at initiation of the study and received vaccination according to group assignment on Day 0 and Day 14. Approximately four (4) weeks later (Day 27), calves were challenged with virulent *M. bovis* or media only according to group assignment. Sixteen (16) days after challenge, (Day 43) the calves were necropsied. The group treatments are summarized in Table 1.

TABLE 1

| Group Treatments | | | | | | | |
|---|---|---|---|---|---|---|---|
| | | Test Substance | | | Challenge | | |
| Groups | Animals/ group | Article | Dose/Route | Admin Schedule | Material | Dose/Route | Admin Schedule |
| Group 1 | 8 | *M bovis* MLV | ~$10^9$ CFU in 2 ml/SQ and ~$10^9$ CFU 2 mL IN | Day 0 and 14 | *M. bovis* (Single Isolate Fresh) | 30 ml of challenge material and 10 ml of PBS | Day 27 (approx 4 weeks after vaccination) |
| Group 2 | 9 | *M bovis* MLV | ~$10^9$ CFU in 2 ml SQ | Day 0 | *M. bovis* (Single Isolate Fresh) | 30 ml of challenge material and 10 ml of PBS | Day 27 (approx 4 weeks after vaccination) |
| Group 3 | 9 | *M bovis* MLV | ~$10^8$ CFU in 2 ml SQ | Day 0 | *M. bovis* (Single Isolate Fresh) | 30 ml of challenge material and 10 ml of PBS | Day 27 (approx 4 weeks after vaccination) |
| Group 4 | 9 | *M bovis* MLV | ~$10^7$ CFU in 2 ml SQ | Day 0 | *M. bovis* (Single Isolate Fresh) | 30 ml of challenge material and 10 ml of PBS | Day 27 (approx 4 weeks after vaccination) |
| Group 5 | 9 | Media Only | 2 ml SQ | Day 0 | *M. bovis* (Single Isolate Fresh) | 30 ml of challenge material and 10 ml of PBS | Day 27 (approx 4 weeks after vaccination) |

High passage live *Mycoplasma bovis* strain, ATCC PTA-9666 (vaccine candidate 052823A131 MS+4), which was passaged 135 times in raw culture media, was used for vaccination. This strain was obtained from naturally occurring disease outbreak then serially passaged in a modified (i.e. modified to remove CNS components therefrom) Friis Media to prepare the material. More specifically, the isolate was grown in Friis media supplemented with 10% yeast extract and 20% horse serum. The culture was grown 24±2 hours at 37° C. after inoculation with an appropriate volume of seed culture determined before the study. Material was then frozen at <−60° C. Prior to vaccination, the material was rapidly thawed and three dose levels were prepared using Friis media as the diluent.

1e9 CFU Preparation (Groups 1 and 2):

2 ml dose administered subcutaneously and (group 1 only) 2 ml dose administered intranasally (1 ml in each nostril).

SQ Total: 8.4E8 CFU/Animal

IN Total: 8.4E8 CFU/Animal

1e8 CFU Preparation (Group 3):

2 ml dose administered subcutaneously.

SQ Total: 9.4E7 CFU/Animal

1e8 CFU Preparation (Group 4):

2 ml dose administered subcutaneously.

SQ Total: 1.0E7 CFU/Animal

Modified Live Vaccine *M. bovis* PTA-9666 (2$^{nd}$ Vaccination) High passage live *Mycoplasma bovis* PTA-9666 in raw culture media.

The isolate used for vaccination was obtained from naturally occurring disease outbreak then serially passaged in the modified Friis Media. Material was prepared at BIVI. The isolate was grown in Friis media supplemented with 10% yeast extract and 20% horse serum. The culture was grown 24±2 hours at 37° C. after inoculation with an appropriate volume of seed culture determined before the study. Material was frozen (<−60° C.). Prior to vaccination, material was rapidly thawed and a single dose level was prepared using Friis media as the diluent.

1e9 CFU Preparation (Group 1):

2 ml dose administered subcutaneously and 2 ml dose administered intranasally (1 ml in each nostril).

SQ Total: 7.2E8 CFU/Animal

IN Total: 7.2E8 CFU/Animal

Media Only (1$^{st}$ Vaccination) Friis Media supplemented with 10% yeast extract and 20% horse s2 ml dose administered subcutaneously.

SQ Total: 0 CFU/Animal serum

A summary of the study timeline is below in Table 2.

TABLE 2

| Study Timeline | | | |
|---|---|---|---|
| Day | Event | Samples | Testing |
| −42 | Acquire Animals | — | — |
| −42 to 0 | General Observations (Daily) | — | — |
| −35 | Collect samples | Nasal swab (Wet/Dry) | *M. bovis* (Culture/PCR) |
| | | Blood (SST) | *M. bovis* (ELISA) |
| | | Ear-notch | BVDV (IHC) |

TABLE 2-continued

Study Timeline

| Day | Event | Samples | Testing |
| --- | --- | --- | --- |
| −3 to −1 | Transfer animals | — | — |
| 0 to 28 | Clinical assessment | — | — |
| 0 | Collect samples | Nasal swab (Wet/Dry) | *M. bovis* (PCR) |
| | | Blood (SST) | *M. bovis* (ELISA) |
| | 1st Vaccination (All Groups) | — | — |
| | Injection site evaluation | — | — |
| 14 | Injection site evaluation. | — | — |
| | Collect samples | Nasal swab (Wet/Dry) | *M. bovis* (Culture/PCR) |
| | | Blood (SST) | *M. bovis* (ELISA) |
| | 2nd Vaccination (Group 1 only) | — | — |
| 27 | Collect samples | Nasal swab (Wet/Dry) | *M. bovis* (Culture/PCR) |
| | | Blood (SST) | *M. bovis* (ELISA) |
| | Injection site evaluation | — | — |
| | Challenge | — | — |
| 27 to 43 | Clinical observation (Daily) | — | — |
| 34 | Collect samples | Nasal swab (Wet/Dry) | *M. bovis* (Culture/PCR) |
| | | Blood (SST) | *M. bovis* (ELISA) |
| 43 | Collect samples (Pre) | Nasal swab (Wet/Dry) | *M. bovis* (Culture/PCR) |
| | | Blood (SST) | *M. bovis* (ELISA) |
| | Necropsy and Gross Pathology (% Lung path) | — | — |
| | Collect samples (Post) | Tonsil swab (Wet/Dry) | *M. bovis* (Culture/PCR) |
| | | Lung Tissue (Preserved) | *M. bovis* (IHC) |
| | | Lung Tissue (Fresh) | *M. bovis* (Culture/PCR) |

Sampling

Swab

Nasal swabs were collected from all calves on Days −22, 0, 14, 27, 34 and 43 (or day of post). At necropsy, tonsil swabs were collected from all calves. Joint swabs were taken from animals with clinical abnormalities. In addition, samples were taken from other locations in certain animals showing area involvement. In all cases, three sterile swabs were rubbed around the regions, as aseptically as possible, for a few seconds and then removed. The swabs were placed back into the transport containers. Two swabs were placed into individual transport containers with media and one was placed into a transport container without media. The swabs were appropriately labeled with the Study number, calf ID number and date. Sample collections were recorded on the Sample Collection Record. The swabs were stored on ice and transported the same day to BIVI—St. Joseph. The deliveries of the swabs were documented on a Specimen Delivery Form Sera Blood was collected from all calves on Days −42, 0, 14, 27, 34 and 43 (or day of post). Blood was collected aseptically from a jugular vein from each calf into one 12.5 mL Serum Separator Tube (SST). Sample collections were recorded on the Sample Collection Record. The blood was delivered to BIVI—St. Joseph with the delivery being documented on a Specimen Delivery Form. Serum was then harvested from each tube by centrifugation and transferred to a sterile cryovial. The samples were stored at 4° C. until testing followed by long term storage at −20° C.

Tissue

From all animals, samples of lung were collected at the discretion of the Study Investigator. Areas in which gross lesions were observed were targeted for sampling. Samples were placed in whirl pack bags and labeled with the animal number. The tissue samples were stored on ice and transported the same day to BIVI—St. Joseph. An additional set of lung tissues were collected and placed into 10% formalin solution and appropriately labeled. Fixed tissue samples were shipped to ISU—Veterinary Diagnostic Laboratory. The sample sites selected for each calf are listed on the Sample Collection Record.

Testing

Microbiology

Swabs placed in the transport media and tissue samples were shipped to BIVI for *Mycoplasma bovis* isolation (day of posting samples only). Briefly, swabs were swirled in 5 mL *Mycoplasma* selective broth. A small sample (approx. 5 mm) was cut from lung tissue and homogenized in 5 mL of complete Friis media. 100 ul of homogenate were added to *Mycoplasma* selective broth. Cultures were incubated at 37C/5% CO2. After 4-14 days, the broth was examined for growth and subcultured to plates for isolation. All positive subculture samples were stored at −70° C.

PCR

Swabs from each calf not placed in transport media and tissue samples were shipped to BIVI where DNA was extracted and tested by PCR using primers and probe specific for the uvrC gene of *M. bovis* developed at BIVI. Results of PCR were expressed as positive or negative for *M. bovis* DNA detection.

Serology

Serum samples were tested using an ELISA commercially available by Biovet (Canada) using the protocol provided with the test kit. ELISA results are expressed as Optical Density (OD) readings. Sample OD's were compared to the Positivity level (Mean ODp×0.3) established by the positive control included in the test kit. Positive results were then interpreted according to the manufacturer's classification scheme. 0 being no seroconversion to 4 being very strong seroconversion (see seroconversion below in Table 3).

TABLE 3

| Seroconversion | |
|---|---|
| Interval | Interpretation |
| OD sample < Positivity Level | Negative (0) |
| Positivity Level < OD Sample < 1.75 * Positivity Level | +1 |
| 1.75 * Positivity Level < OD Sample < 2.3 * Positivity Level | +2 |
| 2.3 * Positivity Level < OD Sample < 3 * Positivity Level | +3 |
| OD Sample > 3 * Positivity Level | +4 |

Histopathology/IHC

Formalin-fixed tissues were sent to ISU Veterinary Diagnostic laboratory and tested by hematoxylin/eosin stained slide and immunohistochemistry using monoclonal antibodies specific for *M. bovis*

Clinicals

Daily general observations were carried out from Day 0 to Day 27 and then daily clinical observations made from Day 28 to euthanasia and necropsy. Clinical and general observations noted deviation from the norm and were documented.

Necropsy

Following euthanasia, each animal was necropsied. The thoracic cavity and trachea were examined for each calf and gross observations recorded on the Necropsy Report Record. The lungs and about 6 inches of trachea from each calf were removed intact for further examination and sample collection.

Lung Pathology

For each set of lungs, each lung lobe was examined by visualization and by palpation. The quality and amount of pathology present (as a percent) per each lung lobe due to *M. bovis* was determined. Each lung lobe percent was then weighted and summed to determine the percentage of total lung with pathology.

Joint Pathology

Affected joints were examined and gross observations recorded.

TABLE 4

| Statistical Methods of Analysis between groups for each parameter | | | |
|---|---|---|---|
| Parameter | Scoring System | Evaluation Of Each Parameter | Statistical Analysis between Groups |
| Total % Lung Pathology | Gross Pathology Sum of % lung lobe pathology multiplied by lobular fraction of total lung per animal | Total % Lung Pathology Scores between groups | Wilcoxon Test |
| Clinical Signs of Coughing Post-Challenge | Clinical Observation (per day) 0 = No Coughing 1 = Coughing | Number of animals with coughing scores >0 from Day 27 (DPC 0) to Day 43 (DPC 16)/ total number of animals in the group. | Fisher's Exact Test |
| | | Number of days with coughing scores >0 from Day 27 (DPC 0) to Day 43 (DPC 16)/ total number of days. | Fisher's Exact Test |
| Clinical Signs of Lameness Post-Challenge | Clinical Observation (per day) Lameness Severity Score (per limb) 0 = No Lameness 1 = Mild 2 = Moderate | Number of animals with total lameness scores >0 from Day 27 (DPC 0) to Day 43 (DPC 16)/ total number of animals in the group. | Fisher's Exact Test |
| | 3 = Severe Note: Score of 5 if removed early from the study for humane reasons | Number of days with total lameness scores >0 from Day 27 (DPC 0) to Day 43 (DPC 16)/ total number of days. | Fisher's Exact Test |
| | Sum of lameness score per animal | Total lameness Scores between groups | Wilcoxon Test |
| Clinical Signs of Joint Swelling Post-Challenge | Clinical Observation (per day) Joint Swelling Score (per animal) 0 = No Swelling 1-12 = Number of joints with swelling | Number of animals with total joint swelling scores >0 from Day 27 (DPC 0) to Day 43 (DPC 16)/ total number of animals in the group. | Fisher's Exact Test |
| | Note: Last score for the remainder of the study if removed early from the study for humane reasons | Number of days with total joint swelling scores >0 from Day 27 (DPC 0) to Day 43 (DPC 16)/ total number of days. | Fisher's Exact Test |
| | | Total Joint Swelling Scores between groups | Wilcoxon Test |
| Early Removal Rates (Mortality or Culling Rate) | Clinical Observation (per day) 0 = Alive 1 = Death or early removal for humane reasons | Number of animals removed from study prior to Day 43 (DPC 16)/total number of animals in the group | Fisher's Exact Test |
| Clinical Signs of Arthritis Score Post-Challenge | Clinical Observation (per day) Sum of total lameness and joint swelling scores | Number of animals with arthritis score >0 from Day 27 (DPC 0) to Day 43 (DPC 16)/total number of animals in the group. | Fisher's Exact Test |
| | | Number of days with arthritis score >0 from Day 27 (DPC 0) to Day 43 (DPC 16)/total number of days. | Fisher's Exact Test |

TABLE 4-continued

| Statistical Methods of Analysis between groups for each parameter | | | |
|---|---|---|---|
| Parameter | Scoring System | Evaluation Of Each Parameter | Statistical Analysis between Groups |
| | | Total Arthritis Scores between groups | Wilcoxon Test |
| | | Total Arthritis Scores between groups by day | Wilcoxon Test |

Percent Reduction for All Parameters
Groups compared using percent reduction [1-(vaccinate/challenge)] and statistical significance for each parameter.

TABLE 5

Percent Reduction and Significance for all Parameters as Compared to the Challenge Control Group - Summary

| | Total % Long Pathology | Clinical Signs of Coughing Post-Challenge | | Clinical Signs of Lameness Post Challenge | | |
|---|---|---|---|---|---|---|
| Group | Total % Lung Pathology Scores | Number of Animals with coughing scores > 0 | Days with coughing scores > 0 | Number of animals with total lameness scores > 0 | Days with total lameness > 0 | Total Lameness scores |
| 1 | 68% | 0% | −57% | 33% | −8% | 70% |
| 2 | 30% | −19% | −129% | 11% | −8% | 31% |
| 3 | 57% | −14% | −86% | 5% | −8% | 10% |
| 4 | 71% | 77% | 85% | −11% | −17% | 6% |

| | Clinical Signs of Joint Swelling Post-Challenge | | | Early Removal Rates | Clinical Signs of Arthritis Score Post-Challenge | | |
|---|---|---|---|---|---|---|---|
| Group | Number of animals with total joint swelling scores > 0 | Days with total joint swelling scores > 0 | Total joint swelling scores | Number of animals removed early from study | Number of animals with arthritis score > 0 | Number of days with arthritis score > 0 | Total Arthritis scores |
| 1 | 33% | 0% | 63% | 83% | 17% | −8% | 67% |
| 2 | 26% | −8% | 58% | 55% | 11% | −8% | 39% |
| 3 | −33% | −8% | 22% | 43% | −33% | −8% | 12% |
| 4 | −14% | −17% | 32% | 33% | −33% | −17% | 10% |

Group 1 = 2 Hi Dose (dual IN/SQ Day 0 and Day 14)
Group 2 = 1 Hi Dose (SQ Day 0)
Group 3 = 1 Mid Dose (SQ Day 0)
Group 4 = 1 Lo Dose (SQ Day 0)
Group 5 = Challenge Only Control (all values are in comparison to challenge controls)

Discussion

The objective of this study was to evaluate the efficacy of a live high passage *M. bovis* vaccine candidate at 3 different dosage levels (1E9, 1E8 and 1E7 CFU per dose) administered subcutaneously (SQ) with a single dose (Day 0). A vaccine control group was also included and given two doses (days 0 and 14) SQ and intranasally (IN) with the high dose level of vaccine.

The challenge and vaccine candidate *Mycoplasma bovis* isolates used in this study originated from different naturally infected farms. The challenge isolate was previously shown to cause both lung and joint disease during experimental challenge and predominated in mixed isolate challenge studies. The live vaccine candidates are high passage isolates originally derived from diagnostic samples. High passage of the vaccine candidates was performed by serial limiting dilution in Friis base media supplemented with horse serum and yeast extract. Although no appreciable difference has been observed in the growth rate in the Friis complete media, at high passage, vaccine candidate PTA-9666 has demonstrated restricted growth on some *Mycoplasma* selective agar formulations while the low passage parent isolate shows no apparent growth restriction. Also, genotypes of the challenge and vaccine isolates are dissimilar (as determined by insertion sequence PCR fingerprinting).

The challenge procedure using a total volume of 30 mL of the challenge isolate and resulted in the challenge control group showing lung pathology in all animals and joint involvement in 6 of 8 animals.

Figure 2:
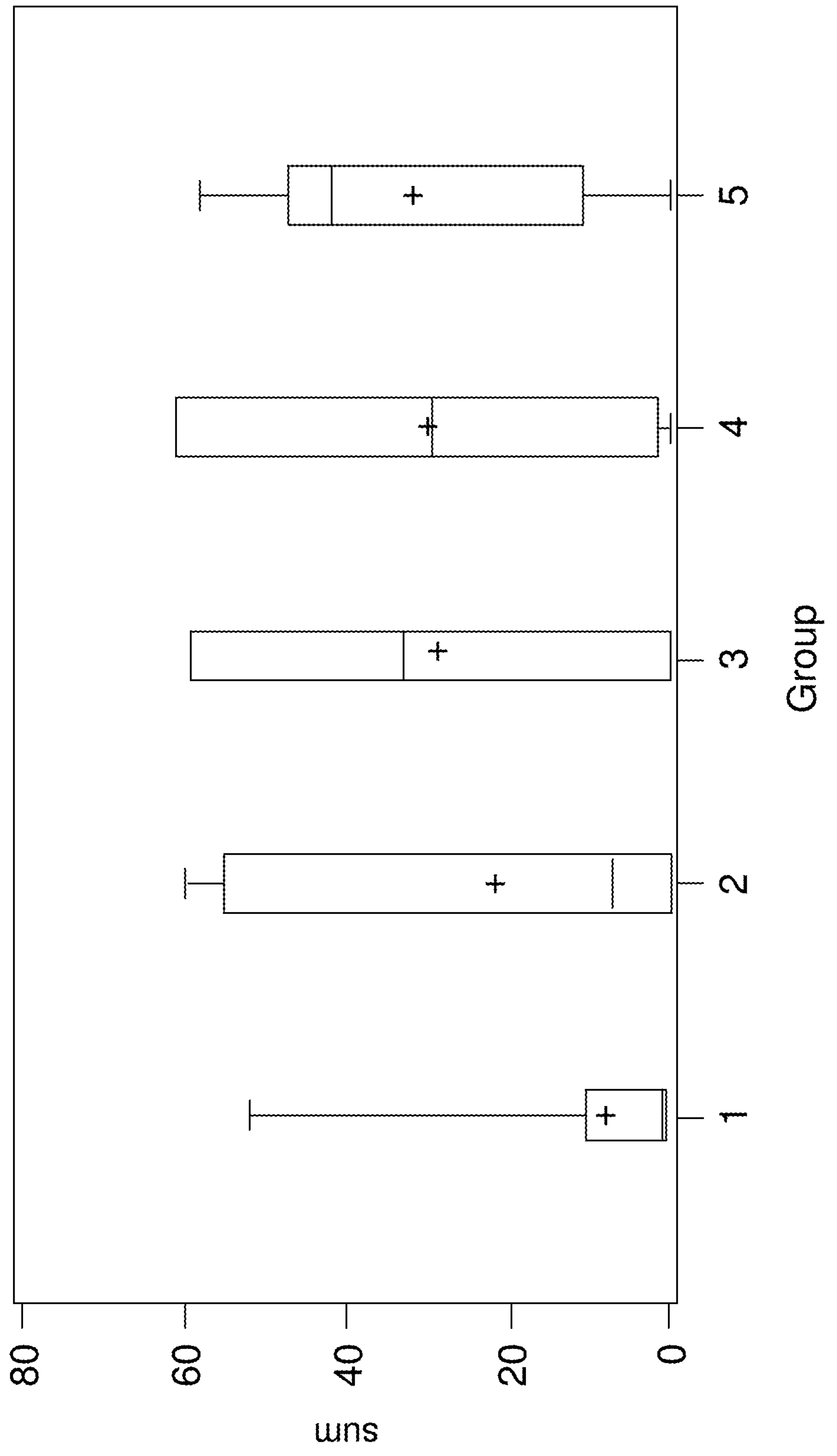
FIG. 2 is a graph illustrating total lameness scores for animals receiving an *M. bovis* isolate passaged 135 times in accordance with the present invention.

Multiple parameters were investigated during this study to access vaccine benefits and identify possible primary parameters for future studies. Of those parameters, animal removal rates and joint clinical signs (lameness and joint swelling) were proposed as indicators of joint protection. Lung pathology (percent gross lung lesions) and clinical signs of coughing were proposed as indicators of lung protection. Lung lesion scores are provided in FIG. 1. Total lameness scores were also taken and are presented in FIG. 2.

Figure 3:
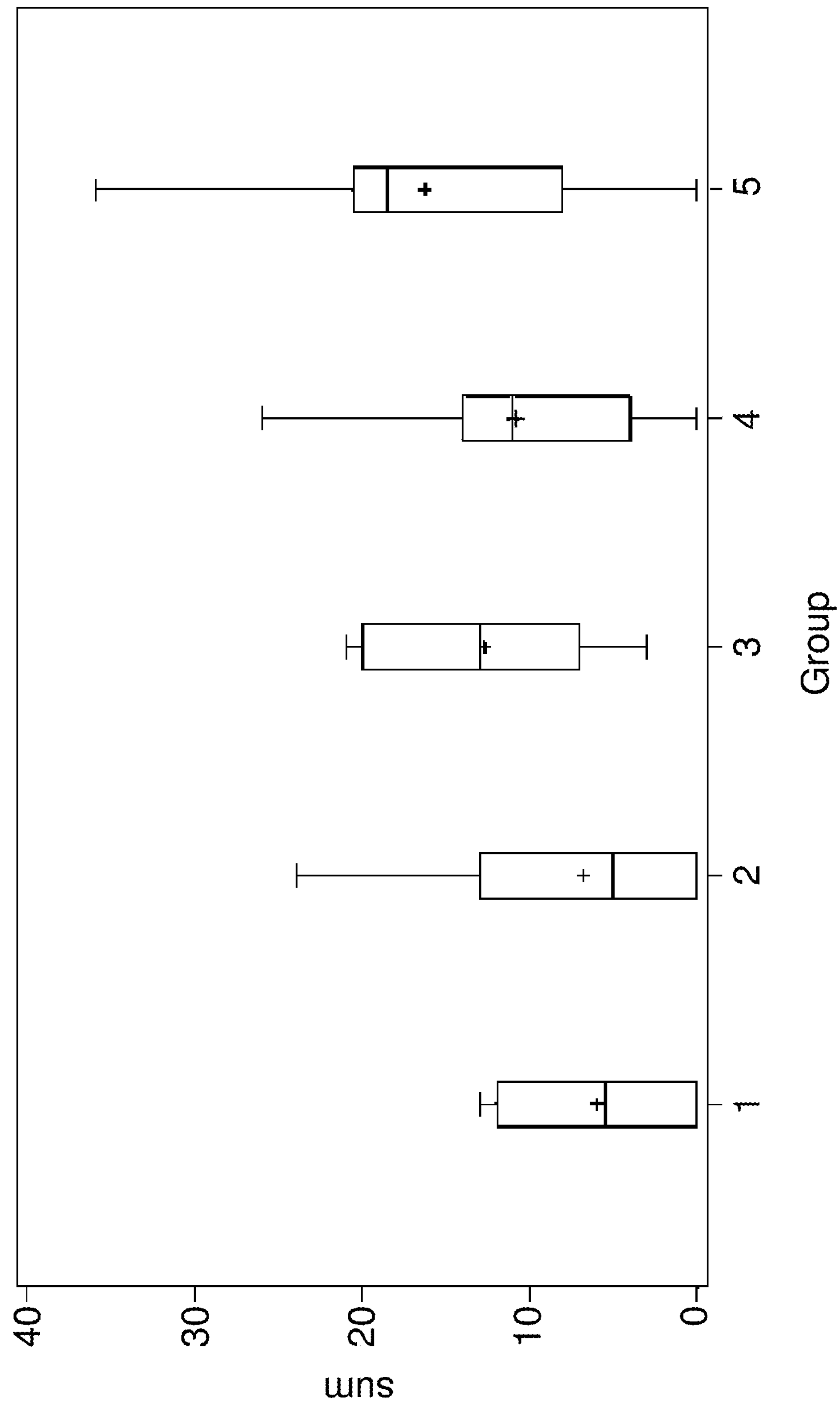
FIG. 3 is a graph illustrating total joint swelling for animals receiving an *M. bovis* isolate passaged 135 times in accordance with the present invention.
Figure 4:
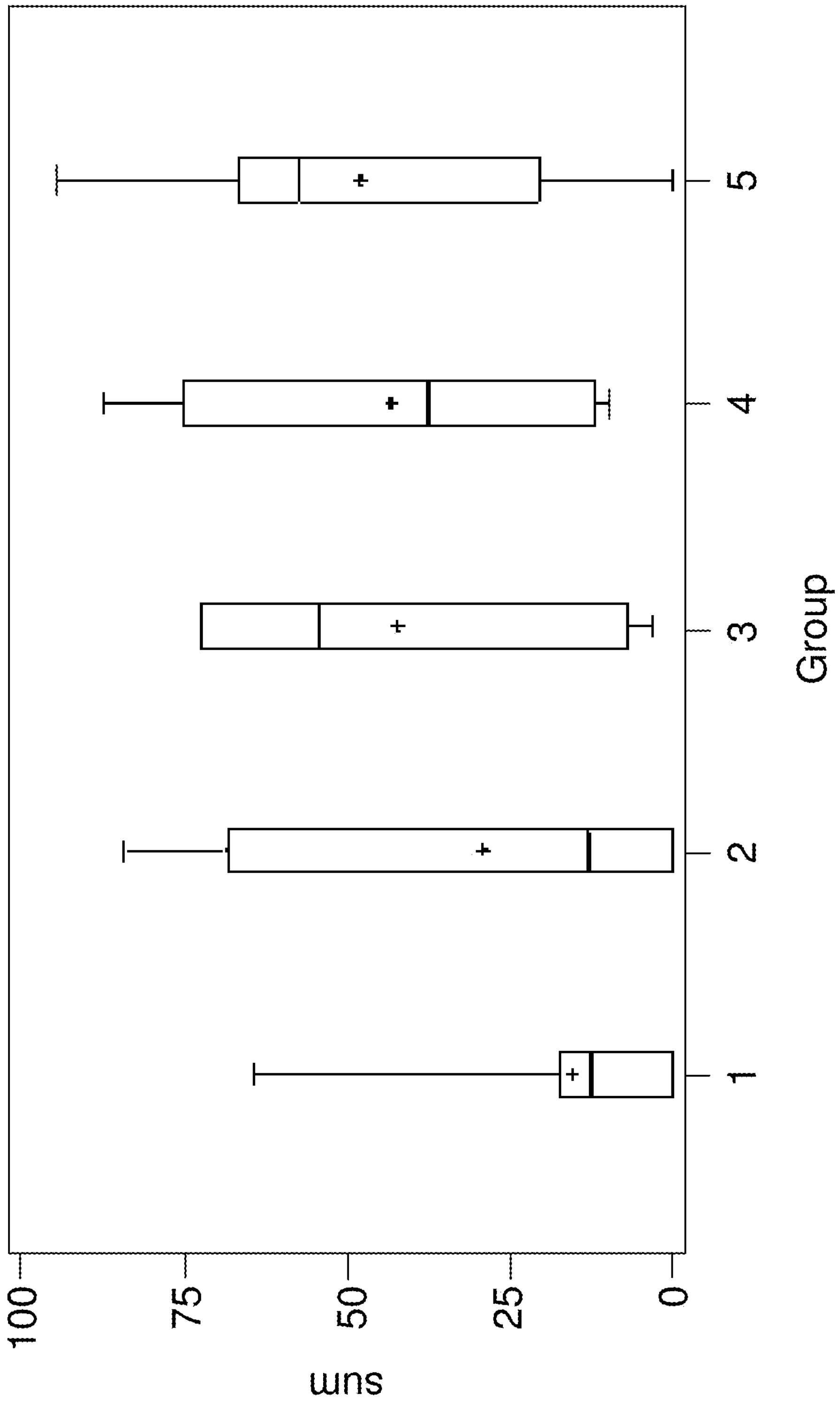
FIG. 4 is a graph illustrating arthritis scores for animals receiving an *M. bovis* isolate passaged 135 times in accordance with the present invention.

Post-challenge, the SQ/IN two high dose vaccine group (group 1) had a lower incidence of joint swelling and removal rates, compared with the challenge control group (group 5). In addition, group 1 showed a trend in a reduced incidence of arthritis as shown in FIG. 4. In the SQ/IN single high dose vaccine group (group 2), a trend was observed in a lower incidence of joint swelling as shown in FIG. 3. Other groups did show a reduction in the incidence of joint clinical signs and removal rates.

Five animals tested positive for *M. bovis* antibodies prior to or on Day 0 and 5 of 9 within the challenge control group tested positive during the vaccination phase prior to challenge (see Protocol Deviation 3 & 4). Reasons for the serum titers prior to exposure may include ELISA reagent cross-reactivity, maternal antibodies and/or residual material from prior studies.

The data for this isolate passaged 135 times was compared to the data for this isolate when passaged at 106 times. Specifically, the data was compared where both passages of the isolate were administered two times subcutaneously and intranasaly. In the 135 passage study, only 1 animal out of 8 were removed from the study due to death and culling. In the 106 passage study, 4 out of 9 animals were removed from the study due to death and culling. Death and culling was reduced in the isolate passaged 135 times by 31.9%. The results are summarized in the Table 6.

TABLE 6

Comparison of 135 passage to 106 passage for death and culling

| | Administration Method | Number of Animals Removed due to Death and culling | Percentage |
|---|---|---|---|
| 135 passage | Two times subcutaneously and intranasaly | 1/8 | 12.5% |
| 106 passage (Live VacI) | Two times subcutaneously and intranasaly | 4/9 | 44.4% |
| Difference | | | 31.9% |

Conclusions

*Mycoplasma bovis* vaccine candidate PTA-9666 via a simultaneous intranasal and subcutaneous route administered 2 times with a 2 week interval at a high dose level (1E9 CFU) showed a reduction of total joint swelling scores and early removal rates (joint protection) in colostrum deprived calves when challenged.

Example 2

Efficacy of Live *Mycoplasma bovis* Vaccine (05-2823 P106) Using Various Administration Routes

Materials and Methods 42 weaned calves negative for *Mycoplasma bovis* were reared. At post weaning (6 weeks±2 weeks), the calves were randomly assigned to 1 of 6 groups. Calves were allowed to adjust for six (6) days and received vaccination according to group assignment on Day 0. Approximately four (4) weeks later (Day 28) all calves were challenged with virulent *M. bovis* according to group assignment. Fourteen (14) days after challenge (Day 42), the calves were necropsied. Three live vaccine candidates were used to immunize the calves. They are referred to as *M. bovis* Live Vaccine I, *M. bovis* Live Vaccine II, and *M. bovis* Live Vaccine III. These three representative strains include 052823A106, deposited with the ATCC in Manassas, Va. on Oct. 16, 2007 under the terms of the Budapest Treaty and designated as PTA-8694 (Live VacI); 05249A102, also deposited with the ATCC in Manassas, Va. on Oct. 16, 2007 under the terms of the Budapest Treaty and designated as PTA 8696 (Live Vac II); and 0519021B106, also deposited with the ATCC in Manassas, Va. on Oct. 16, 2007 and designated as PTA 8695 (Live Vac III).

Groups 1, 2, and 3 were given Live Vaccine I on Day 0 and Day 14. Group 1 was administered 2 mL subcutaneously and 2 mL intranasally for each administration. Group II was administered 2 mL subcutaneously for each administration. Group III was administered 2 mL intranasally for each administration. Group IV was a control group and was administered 2 mL of media subcutaneously and 2 mL of media intranasally for each administration. Group V was administered Live Vaccine II on Day 0 and Day 14 at a dose of 2 mL subcutaneously and 2 mL intranasally for each administration. Group VI was given Live Vaccine III on Day 0 and Day 14 at a dose of 2 mL subcutaneously and 2 mL intranasally for each administration. All groups were challenged with virulent *M. bovis* on Day 28. A summary of the Study Design is illustrated in Table 7.

TABLE 7

| Group Treatments | | | | | | | |
|---|---|---|---|---|---|---|---|
| | | Test Substance | | | Challenge | | |
| Groups | Animals/ group | Article | Dose/Route | Admin Schedule | Material | Dose/Route | Admin Schedule |
| Group 1 | 10 | *M bovis* Live I | 2 ml SQ and 2 mL IN | Day 0 and 14 | *M. bovis* (24466-192) | 120 ml of challenge material with 15 ml PBS | Day 28 (approx 4 weeks after vaccination) |
| Group 2 | 10 | *M bovis* Live I | 2 ml SQ | Day 0 and 14 | *M. bovis* (24466-192) | 120 ml of challenge material with 15 ml PBS | Day 28 (approx 4 weeks after vaccination) |
| Group 3 | 9 | *M bovis* Live I | 2 mL IN | Day 0 and 14 | *M. bovis* (24466-192) | 120 ml of challenge material with 15 ml PBS | Day 28 (approx 4 weeks after vaccination) |
| Group 4 | 9 | Media Only | 2 ml SQ and 2 mL IN | Day 0 and 14 | *M. bovis* (24466-192) | 120 ml of challenge material with 15 ml PBS | Day 28 (approx 4 weeks after vaccination) |
| Group 5 | 2 | *M bovis* | 2 ml SQ and | Day 0 and 14 | *M. bovis* (24466- | 120 ml of challenge | Day 28 (approx 4 |

TABLE 7-continued

| Group Treatments | | | | | | | |
|---|---|---|---|---|---|---|---|
| | | Test Substance | | | Challenge | | |
| Groups | Animals/ group | Article | Dose/Route | Admin Schedule | Material | Dose/Route | Admin Schedule |
| | | Live II | 2 mL IN | | 192) | material with 15 ml PBS | weeks after vaccination) |
| Group 6 | 2 | *M bovis* Live III | 2 ml SQ and 2 mL IN | Day 0 and 14 | *M. bovis* (24466-192) | 120 ml of challenge material with 15 ml PBS | Day 28 (approx 4 weeks after vaccination) |

The *M. bovis* Live Vaccine I isolate used for vaccination was obtained from naturally occurring disease outbreak then serially passaged (106 times) in modified Friis Media. The isolate was grown in Friis media supplemented with 10% yeast extract and 20% horse serum. The culture was grown 24±2 hours at 37° C. after inoculation with an appropriate volume of seed culture determined before the study. The isolate was used without dilution. The average pre and post vaccination concentration was found to be 3.0E9 CFU/ml.

The *M. bovis* Live Vaccine II isolate used for vaccination was obtained from naturally occurring disease outbreak then serially passaged (102 times) in modified Friis Media. The isolate was grown in Friis media supplemented with 10% yeast extract and 20% horse serum. The culture was grown 24±2 hours at 37° C. after inoculation with an appropriate volume of seed culture determined before the study. The isolate was used without dilution. The average pre-vaccination concentration was found to be 7.8E8 CFU/ml.

The *M. bovis* Live Vaccine III isolate used for vaccination was obtained from naturally occurring disease outbreak then serially passaged (106 times) in modified Friis Media. The isolate was grown in Friis media supplemented with 10% yeast extract and 20% horse serum. The culture was grown 24±2 hours at 37° C. after inoculation with an appropriate volume of seed culture determined before the study. The isolate was used without dilution. The average pre vaccination concentration was found to be 1.7E8 CFU/ml.

The challenge material, a virulent *M. bovis* isolate was obtained from naturally occurring disease outbreak. The average pre and post challenge concentration was found to be 1.8E9 CFU/ml.

Samples were taken from the animals, such as nasal swabs and blood tests. The Sample Schedule is summarized in Table 8.

TABLE 8

| Study Timeline | | | |
|---|---|---|---|
| Day | Event | Samples | Testing |
| approx. −42 | Acquire Animals | — | — |
| −42 to 0 | General Observations (Daily) | — | — |
| Approx −35 | Collect samples | Nasal swab (Wet/Dry) | *M. bovis* (Culture/PCR) |
| | | Blood (SST) | *M. bovis* (ELISA) |
| | | Ear-notch | BVDV (IHC) |
| −6 | Transfer animals | — | — |
| 0 to 28 | Clinical assessment | — | — |
| 0 | Collect samples | Nasal swab (Wet/Dry) | *M. bovis* (Culture/PCR) |
| | | Blood (SST) | *M. bovis* (ELISA) |
| | 1st Vaccination | — | — |
| 14 | Injection site evaluation. | — | — |
| | Collect samples | Nasal swab (Wet/Dry) | *M. bovis* (Culture/PCR) |
| | | Blood (SST) | *M. bovis* (ELISA) |
| | 2nd Vaccination | — | — |
| 27 | Collect samples | Nasal swab (Wet/Dry) | *M. bovis* (Culture/PCR) |
| | | Blood (SST) | *M. bovis* (ELISA) |
| 28 | Challenge | — | — |
| 29 to 42 | Clinical observation (Daily) | — | — |
| 35 | Collect samples | Nasal swab (Wet/Dry) | *M. bovis* (Culture/PCR) |
| | | Blood (SST) | *M. bovis* (ELISA) |
| 41 | Collect samples | Nasal swab (Wet/Dry) | *M. bovis* (Culture/PCR) |
| | | Blood (SST) | *M. bovis* (ELISA) |
| 42 | Necropsy and Gross Pathology | — | — |
| | Collect samples (Post) | Tonsil swab (Wet/Dry) | *M. bovis* (Culture/PCR) |
| | | Lung Tissue (Preserved) | *M. bovis* (IHC) |
| | | Lung Tissue (Fresh) | *M. bovis* (Culture/PCR) |
| | | Joint swabs (Wet/Dry) | *M. bovis* (Culture/PCR) |

Sampling

Nasal swabs were collected from all calves on Days 0, 14, 27, 35 and 41. At necropsy, tonsil swabs were collected from all calves. Joint swabs were taken from animals with clinical abnormalities. In addition, samples were taken from other locations in certain animals showing area involvement. In all cases, three sterile swabs were rubbed around the regions, as aseptically as possible, for a few seconds and then removed.

Tissue

From all animals, samples of lung were collected. Areas in which gross lesions were observed were targeted for sampling. An additional set of lung tissues were collected and placed into 10% formalin solution.

Sera

Blood was collected from all calves on Days 0, 14, 27, 35 and 41. Blood was collected aseptically from a jugular vein from each calf into one 12.5 mL Serum Separator Tube (SST).

Testing

Microbiology

Briefly, swabs were swirled in 5 mL *Mycoplasma* selective broth. A small sample (approx. 5 mm) was cut from lung tissue and homogenized in 2 mL of complete Friis media. 100 ul of homogenate were added to *Mycoplasma* selective broth. Cultures were incubated at 37C/5% CO2. After 4-14 days, the broth was examined for growth and subcultured to plates for isolation. All positive subculture samples were stored at −70° C.

PCR

DNA was extracted and tested by PCR using primers and probe specific for the uvrC gene of *M. bovis*. Results of PCR were expressed as positive or negative for *M. bovis* DNA detection.

Serology

Serum samples were tested using an ELISA commercially available by Biovet (Canada) using the protocol provided with the test kit. ELISA results are expressed as Optical Density (OD) readings. Sample OD's were compared to the Positivity level (Mean ODp×0.3) established by the positive control included in the test kit. Positive results were then interpreted according to the manufacturer's classification scheme, with 0 being no seroconversion to 4 being very strong seroconversion.

Histopathology/IHC

Formalin-fixed tissues were sent to ISU Veterinary Diagnostic laboratory and tested by hematoxylin/eosin stained slide and immunohistochemistry using monoclonal antibodies specific for *M. bovis.*

Clinical Signs

Daily general observations were carried out from Day 0 to Day 28 and then daily clinical observations made from Day 29 to euthanasia and necropsy. Clinical and general observations noted deviation from the norm and were documented.

Necropsy

Following euthanasia, each animal was necropsied. The thoracic cavity and trachea were examined for each calf and gross observations recorded on the Necropsy Report Record. The lungs and about 6 inches of trachea from each calf were removed intact for further examination and sample collection.

For each set of lungs, the dorsal and ventral lung surfaces were photographed with an appropriate ear tag alongside each view.

Lung Pathology

For each set of lungs, each lung lobe was examined by visualization and by palpation. An approximation of how much pathology was present (as a percent) per each lung lobe due to *M. bovis* was determined. Each lung lobe percent was then weighted and summed to determine the percentage of total lung with pathology.

Joint Pathology

Affected joints were examined and gross observations recorded.

Changes to the Study Protocol

Six animals were excluded from analysis. One animal each was excluded from Groups I, II, and III. Three animals were excluded from Group IV. The one animal in Group II was found dead with lung pathology inconsistent with *M. bovis*, and the rest were excluded from analysis for testing positive for *M. bovis*. Twenty-two animals were removed prior to study termination from Day 30-38 for humane reasons. One animal in Group 5 was removed on Day 40, prior to study termination, because the animal died by asphyxiation after becoming trapped in the feed bunk.

Results and Discussion

Post-Challenge Clinical Signs

Clinical observations were made from Day 28 through Day 42. Coughing, labored respiration, depression, swollen joints, lameness and droopy ear were clinical observations noted during this phase of the study. Clinical signs were divided into three types (respiratory, joint and other) typical of *Mycoplasma bovis* infection. Respiratory signs included coughing, rapid/labored respiration and nasal discharge. Joint signs included swollen joints and lameness.

Lung Pathology

At necropsy, lungs were collected and observed for lesions associated with *M. bovis*. Animals exhibited variability in pathological features such as consolidation and nodular lesion formation. Results of lung involvement were expressed as a percent using a scoring system, which reflects the percentage of the total lung with gross pathology associated with *M. bovis* infection. In some cases, determination of lung percent involvement was hampered by adhesions or the atypical nature of lesions.

Joint Pathology

At necropsy, joints from animals that previously exhibited clinical symptoms (swelling and/or lameness) were examined for gross pathology. Areas affected varied by animal and may involve the carpus, hock, stifle, fetlock and/or elbow. Animals presented with gross swelling, increased synovial fluid, abnormal fluid appearance, or thickening of the joint capsule. In more severely affected calves, fibrin was present as was erosion of the articular surface. Samples of joint fluid and/or surface swabs were tested by culture and PCR for the presence of *Mycoplasma bovis.*

PCR Detection of *M. bovis* from Nasal, Tonsil and Lung Samples

The nasal passages were sampled from each animal by swab on Day 0, 14, 27, 35 and 41 or Day of Necropsy. In addition, during the post-mortem, samples of tonsils were taken by swab and representative lung tissue was recovered. The frequency of detection using real-time PCR targeting a general *M. bovis* marker (uvrC) was analyzed. In addition, tonsil and lung tissue were analyzed using a recently developed end-point PCR assay targeting markers not found in the *M. bovis* challenge isolate but found in all vaccine candidates.

*M. bovis* Serology

Figure 5:
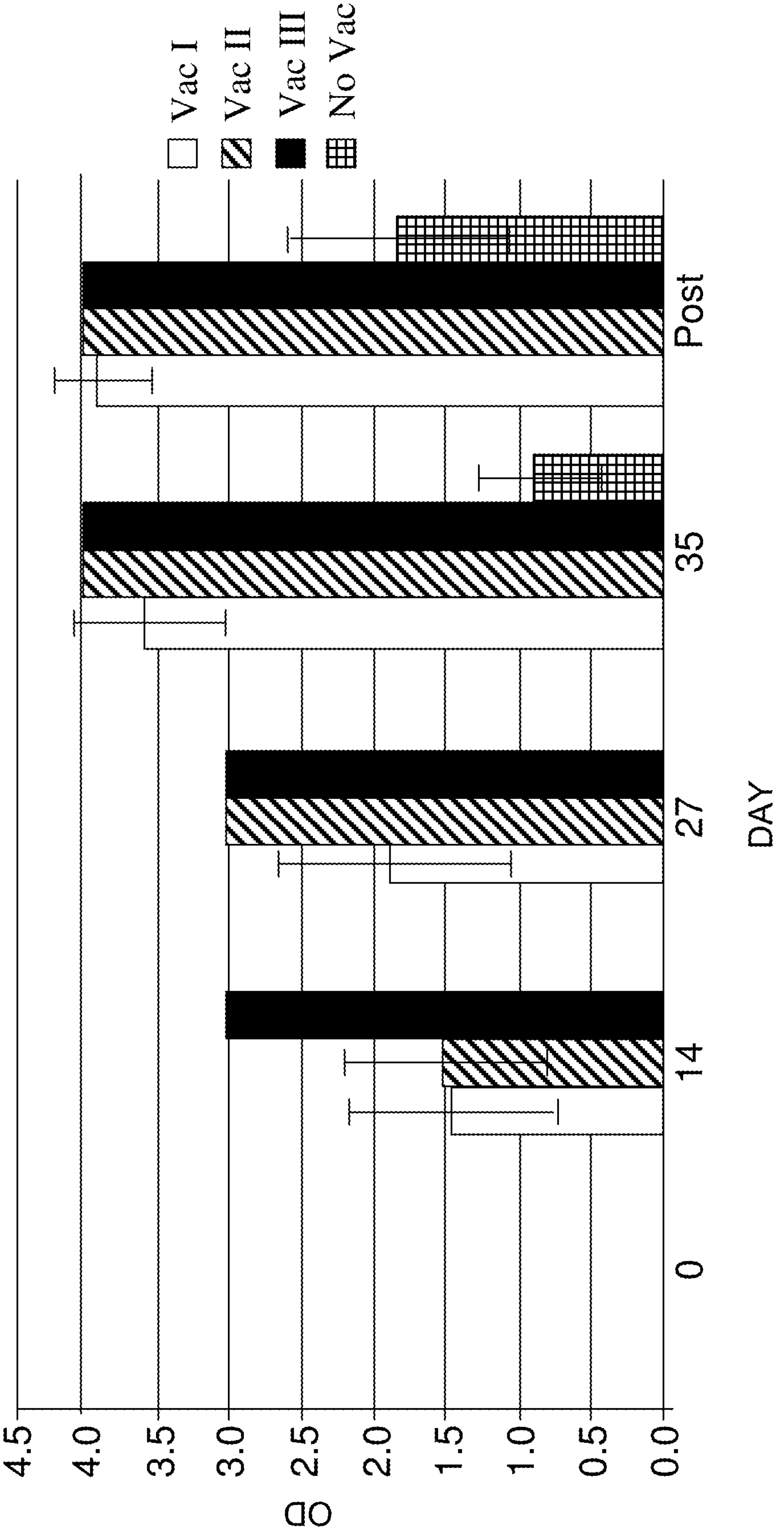
FIG. 5 is a graph illustrating a comparison of serology for Live Vac I, II, III and No Vaccine Group (SQ+IN only)
Figure 6:
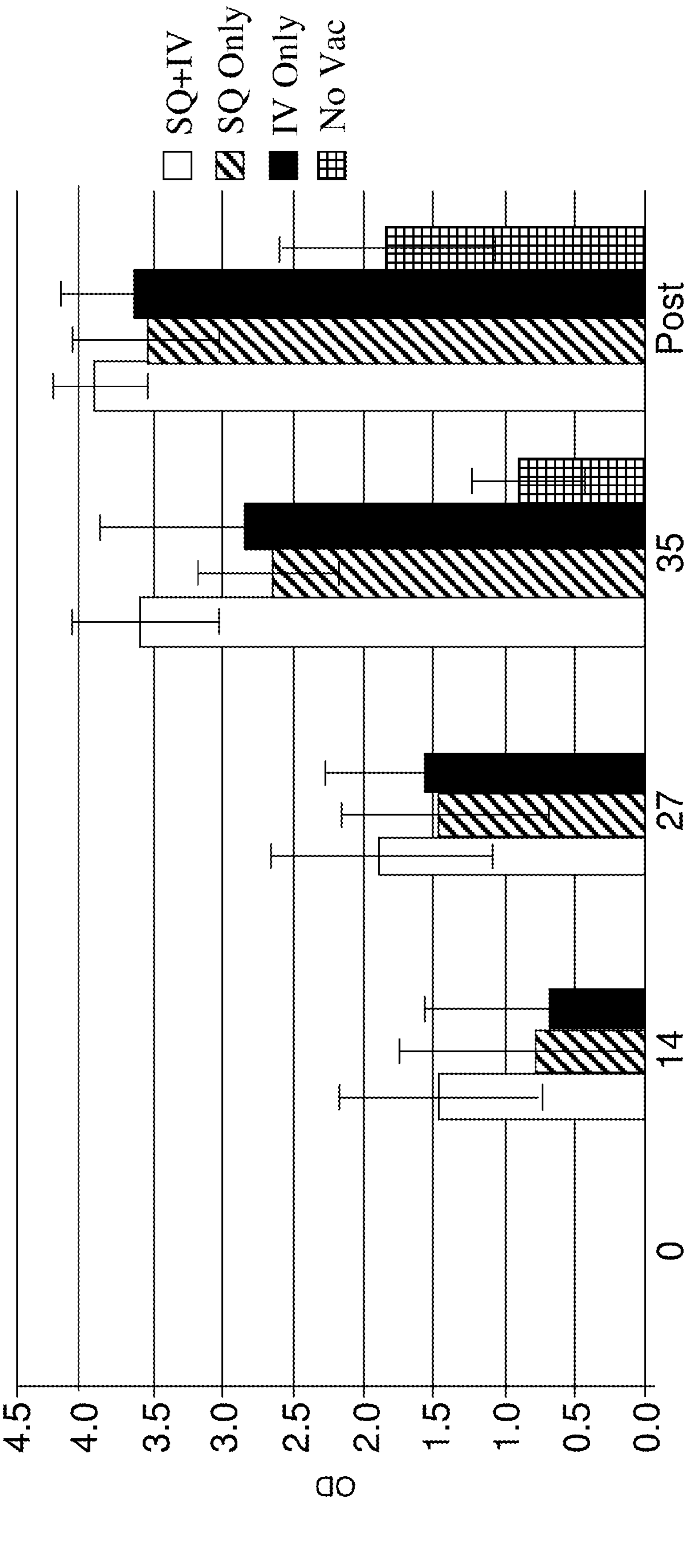
FIG. 6 is a graph illustrating a comparison of serology for Live Vac I using various routes of administration.

All samples were tested in the Biovet *M. bovis* ELISA to monitor the serological response to *M. bovis*. Seroconversion was scored according to grouped multipliers of positivity ODs. The mean serological scores detected from each group on Day 0, 14, 27, 35 and Post (post represents a range of study days from 37 to 41 due to early removal of certain animals) were analyzed. FIG. 5 illustrates the serology results for Live Vac I, II, III, and controls and FIG. 6 illustrates the comparison of serology for Live Vac I using various routes of administration.

Discussion

The objective of this study was to assess the efficacy of an experimental live *Mycoplasma bovis* vaccine (05-2823 P106) using various 2 mL administration routes (SQ, IN, SQ+IN) fourteen days apart and a dual challenge model in the target species. The challenge model used a high volume administered to two locations of the lung with the addition of an IV administration. In addition, two other live vaccine candidates (05-249 P102 and 05-1902-1 P106) were evaluated for efficacy using only the SQ+IN route.

The challenge and vaccine candidate *Mycoplasma bovis* isolates originated from different naturally infected farms. The challenge isolate was previously shown to cause both lung and joint disease during experimental challenge and predominated in mixed isolate challenge studies. The live vaccine candidates are high passage isolates originally derived from diagnostic samples. High passage of the vaccine candidates was performed by serial limiting dilution in Friis base media supplemented with horse serum and yeast extract. Although no appreciable difference has been observed in the growth rate in the Friis complete media, at high passage, vaccine candidate 05-2823 P106 has demonstrated restricted growth on some *Mycoplasma* selective agar formulations while the low passage parent isolate shows no apparent growth restriction. Also, genotypes of the challenge and vaccine isolates are dissimilar (as determined by insertion sequence PCR fingerprinting).

The challenge procedure using a total volume of 120 mL of the challenge isolate administered to each animal resulted in the challenge only group showing lung pathology and joint involvement in all animals.

Multiple parameters were investigated during this study to access vaccine benefits. Of those parameters, animal removal rates and joint clinical symptoms were used as primary indicators of joint protection. Lung pathology (percent gross lung lesions) was used as the primary indicator of lung protection. Other data such as detection of organism from tissue, joint distribution, and serology provided additional data for conformation.

All groups showed some lung and joint protective benefit after receiving the vaccine candidate *Mycoplasma bovis* Live Vaccine I (05-2823 P106) regardless of route or route combination as demonstrated by a reduction in lung lesions, joint clinical symptoms and animal removal rates. The combined SQ and IN route (Group 1) resulted in the greatest reduction of lung lesions (86%) compared to the groups using only a single route. Additionally, results of lung lesions, joint clinical symptoms and removal rate reductions suggest benefit from receiving the two other vaccine candidates Live Vaccine II (05-249 P102) and Live Vaccine III (05-1902-1 P106) by a combined SQ and IN route. ELISA results demonstrated a strong humoral response to vaccination with all vaccine candidates.

All vaccine candidates demonstrated safety. No animals from any group receiving a vaccine presented with clinical symptoms during the vaccination period and only one animal that had received Live Vaccine III (05-1902-1 P106) showed reactivity at an injection site. Additionally, results of PCR showed non-challenge *M. bovis* detection from the tonsil tissue of only groups receiving a vaccine candidate via the IN route and detection of non-challenge from lung tissue in only a single animal that had received Live Vaccine I (05-2823 P106) by both IN and SQ routes. A comparison of serology for Live Vac I, II, II, and no vaccine where the vaccine was administered subcutaneously and intramuscularly, is provided in FIG. 5. FIG. 5 illustrates that Live Vac III consistently had the highest level of serology, with Live Vac II being equal in serology with Live Vac III for days 27, 35, and post necropsy. All groups had higher serology than the group given no vaccine. FIG. 6 illustrates a comparison of the serology for Live Vac I, using various routes of administration. Subcutaneous and intramuscular administration consistently had the highest serology over the period of the study, with intramuscular administration only being in second. All groups had higher serology values than those animals not administered vaccine.

Conclusions

Protective benefits (respiratory and joint) were observed for *M. bovis* vaccine candidates Live Vaccine I (05-2823 P106), Live Vaccine II (05-249 P102) and Live Vaccine III (05-1902-1 P106) via a simultaneous intranasal and subcutaneous route administered 2 times with a 2 week interval in colostrum deprived calves using a dual lung/joint challenge.

Protective benefits (respiratory and joint) were observed for *M. bovis* vaccine candidate Live Vaccine I (05-2823 P106) with either intranasal or subcutaneous route administered 2 times with a 2 week interval in colostrum deprived calves using a dual lung/joint challenge.

Example 3

DNA Fingerprinting

The DNA fingerprinting process was used to differentiate *M. bovis* strains by isolating, amplifying and detecting DNA using the methods and primers as disclosed in WO 2008-030619.

Materials and Methods

*Mycoplasma* sp. isolates were used in the studies. Isolates were obtained from in-house sources or field isolates obtained from infected animals. Isolates were grown using a combination of *Mycoplasma*-selective agar and broth for 1-7 days. To isolate DNA, broth cultures were spun and pelleted. DNA from the pellet was then extracted (using the Qiagen DNeasy Tissue Kit and resuspended in molecular grade water). Genomic DNA was quantitated using Picogreen (Invitrogen). Primers were designed based on the known insertion sequences (transposable elements) present in the bacterial genome (*Mycoplasma bovis*) and are disclosed in WO 2008-030619. Outwardly facing primers were manually selected from the element ends (excluding the terminal repeat regions) at a Tm of 55-58C. PCR reactions were then carried out using a multiplex PCR master mix (Qiagen Multiplex PCR Kit). The reactions contained 1× Master mix, 300 nM of each primer and 1 ng of template DNA. Thermal cycling conditions were 95° C. for 15 minutes, 35 cycles of 94° C. for 30 seconds, 56.1° C. for 90 seconds, 72° C. for 2 minutes, with a final extension of 72° C. for 4 minutes and a 4° C. hold. The amplified products were separated on a 4% agarose gel with ethidium bromide (Invitrogen E-gel), run for 50 minutes at room temperature and imaged under UV light.

Results and Discussion

The results showed that each of the isolates used in this application had a unique fingerprint. However, as shown in Example 2, each isolate was also an effective attenuated live culture vaccine that was effective at providing cross protection against a challenge isolate having a different fingerprint than any of the vaccine candidates. Three field isolates, 05-2823 P106 (PTA-8694), 05-249 P102 (PTA-8696), and 05-1902-1-P106 (PTA-8695), were grown and DNA isolated according to the above protocol. 2-5 ng of DNA from each isolate was amplified according to the above protocol using a multiplex of 4 sets of IS primers identified as SEQ ID Nos. 1-8 as disclosed in WO 2008-030619. The amplified products were separated on a Invitrogen E-gel 4% agarose gel containing ethidium bromide (according to manufacturer) for 50 minutes and visualized under UV light. All isolates produced unique patterns. The patterns were reproducible using independent aliquots under the sample PCR reaction conditions.

Example 4

Comparative Analysis of Efficacy of *Mycoplasma bovis* Vaccine at Passage 135 as Compared to Vaccine at the Lower Passage Level of 106

The study in Example 2 used the *Mycoplasma bovis* vaccine at the lower passage 106, and measured the effectiveness in protecting vaccinated calves from 3 key manifestations of *Mycoplasma bovis* disease: clinical signs of respiratory disease, lameness, and "early removal" or euthanasia and death resulting from a severe myriad of clinical signs caused by *Mycoplasma bovis* disease. The latter manifestation of disease is obviously most consequential, and hence, was considered the most important feature of vaccine efficacy. This most important parameter was used to measure any differences in efficacy between vaccine at passage 106 and passage 135.

In the study described in Example 2 with passage 106 vaccine, Group 1 (Live Vac I SQ+IN) received vaccine twice at 14 day intervals and via two routes of administration, intranasal (IN) and subcutaneously (SQ), at each vaccination event. Separate groups of calves were also vaccinated with passage 106 vaccine. Most pertinent was Group 2 (Live Vac I SQ) which was given vaccine twice at 14 day intervals but via one route of administration, only subcutaneously (SQ), at each vaccination event.

Following vaccination, both the vaccinated Group 1 and Group 2 and a separate assembly (Group 4) of non-vaccinated (No Vac) calves were purposely exposed to virulent *Mycoplasma bovis* delivered directly into each calf. Disease resulting from the challenge exposure was measured and compared among the groups, and specifically, comparing the most significant disease "early removal" (death) in vaccinated Group 1 and Group 2 to the non-vaccinated (No Vac) calves of Group 4 to measure the effectiveness of the passage 106 vaccine. As presented in Table 8, passage 106 vaccinated Group 2 given vaccine twice at 14 day intervals but via one route of administration, subcutaneously, provided a notable 56% reduction in death/euthanasia. Group 1 (Live Vac I SQ+IN) given passage 106 vaccine twice at 14 day intervals and via two routes of administration, intranasal (IN) and subcutaneously (SQ), at each vaccination event, provided the same notable 56% reduction in death/euthanasia of vaccinated calves.

TABLE 9

| | Respiratory | | | Joint | | | Early Removal | | |
|---|---|---|---|---|---|---|---|---|---|
| Group | Affected | Fequency | % Reduction | Affected | Fequency | % Reduction | Affected | Fequency | % Reduction |
| 1 Live Vac I (SQ + IN) | 3/9 | 33% | 0% | 6/9 | 67% | 33% | 4/9 | 44% | 56% |
| 2 Live Vac I (SQ) | 0/9 | 0% | 100% | 7/9 | 78% | 22% | 4/9 | 44% | 56% |
| 4 No Vac | 2/6 | 33% | | 6/6 | 100% | | 6/6 | 100% | |

In this study the *Mycoplasma bovis* vaccine at the higher passage 135 was also evaluated for its effectiveness in protecting vaccinated calves from the most important manifestation of *Mycoplasma bovis* disease, "early removal rates" or euthanasia and death resulting from a severe myriad of clinical signs caused by *Mycoplasma bovis* disease. In the study described in Example 1, Group 1 also received vaccine twice at 14-day intervals via two routes of administration, intranasal (IN) and subcutaneously (SQ), at each vaccination event as was done in the study described in Example 2, with passage 106 vaccine. However, the critical difference between the vaccines in Group 1 of each of these two studies was passage level. In the study of Example 2 Group 1 was given vaccine at passage level 106, and in this second Study of Example 1 Group 1 received vaccine at the higher passage 135.

Separate groups of calves were also vaccinated with passage 135 vaccine in the study described in Example 1. Most pertinent again was Group 2 which was given vaccine only once via one route of administration, subcutaneously (SQ). Following vaccination, both the vaccinated Group 1 and Group 2 and a separate assembly (Group 5) of non-vaccinated calves were purposely exposed to virulent *Mycoplasma bovis* delivered directly into each calf. Disease resulting from the challenge exposure was measured and compared among the groups. Specifically, efficacy was determined by comparing the most significant disease "early removal rates" (death) in vaccinated Group 1 and Group 2 to the non-vaccinated calves of Group 5 to measure the effectiveness of the passage 135 vaccine. As presented in Table 10, Group 1 given passage 135 vaccine twice at 14 day intervals via two routes of administration, intranasal (IN) and subcutaneously (SQ), at each vaccination event provided a quite unanticipated and very high effectiveness by reducing calf early removal rates (death) by 83%, or much higher efficacy than was achieved with passage 106 vaccine that provided a notable but lower 56% reduction of early removal rates. The comparative results between the two studies appear in Table 11.

Also unanticipated was the efficacy achieved in Group 2 the study of Example 1, with a single dose of vaccine. Group 2 received just a single dose of passage 135 vaccine via one route of administration, subcutaneously. This higher passage 135 vaccine provided a 55.6% (56%) reduction in calf death/euthanasia. By contrast, the 106 passage vaccine required two doses of vaccine, a priming dose followed by a booster 14 days later in the study of Example 2 to achieve comparable efficacy delivered in just one dose (no booster needed) to calves receiving passage 135 vaccine in the study of Example 1.

TABLE 10

Percent Reduction and Significance for all Parameters in comparison to the Challenge Control

| | Total % Lung Pathology | Clinical Signs of Coughing Post-Challenge | | Clinical Signs of Lameness Post-Challenge | | |
|---|---|---|---|---|---|---|
| Group | Total % Lung Pathology Scores | Number of animals with coughing scores > 0 | Days with coughing scores > 0 | Number of animals with total lameness scores of > 0 | Days with total lameness scores > 0 | Total Lameness Scores |
| 1 | 68% * | 0% | −57% | 33% | −8% | 70% * |
| 2 | 30% | −19% | −129% | 11% | −8% | 31% |

| | Clinical Signs of Joint Swelling Post-Challenge | | | Early Removal Rates | Clinical Signs of Arthritis Score Post-Challenge | | |
|---|---|---|---|---|---|---|---|
| Group | Number of animals with total joint swelling scores > 0 | Days with total joint swelling scores > 0 | Total Joint Swelling Scores | Number of animals with arthritis score > 0 | Number of days with arthritis score > 0 | Number of days with arthritis score > 0 | Total Arthritis Scores |
| 1 | 33% | 0% | 63% ** | 83% ** | 17% | −8% | 67% * |
| 2 | 26% | −8% | 58% * | 55% * | 11% | −8% | 39% |

Group 1 = 2 Hi Dose (dual IN/SQ Day 0 and Day 14)
Group 2 = 1 Hi Dose (SQ Day 0)

TABLE 11

Comparative Results of Passage 135 and Passage 106 Vaccine

| Study Number | Group | Vaccine Passage | Doses | Booster | Route of Vacci-nation | Reduction: Death due to *M. bovis* |
|---|---|---|---|---|---|---|
| Example 2 | 1 | 106 | 2 | Yes | IN & SQ | 56% |
| Example 1 | 1 | 135 | 2 | Yes | IN & SQ | 83%[a] |
| Example 2 | 2 | 106 | 2 | Yes | SQ | 56% |
| Example 1 | 2 | 135 | 1[b] | No | SQ | 56% |

[a]passage 135 vaccine provides unanticipated reduction in death due to *M. bovis* compared to passage 106
[b]passage 135 vaccine is effective as single dose without need for booster, whereas passage 106 requires a booster for comparable reduction in death due to *M. bovis*

Hence, the passage 135 vaccine yielded an improved and unexpectedly higher level of efficacy by significantly reducing death due to *Mycoplasma bovis* infection using a more convenient, less costly single dose of vaccine, whereas the lower passage 106 vaccine required two doses of vaccine to provide comparable efficacy. In addition, substantially better efficacy of 83% reduction in death was achieved with high passage Group 1 of the study of Example 1 using an identical vaccination regimen as used with low passage Group 1 of the study of Example 2, the only difference being the passage 135 vaccine in the former and passage 106 vaccine in the latter study. The passage 135 vaccine reduced death due to *Mycoplasma bovis* by 83% as compared to a lower but notable efficacy with passage 106 vaccine of 56%. Typically the efficacy of a vaccine is reduced on progressive passages in vitro as the microorganism further adapts to cell culture and loses expression of potentially immunogenic virulence proteins. Unexpectedly, the avirulent *M. bovis* vaccine of this invention demonstrated improved effectiveness in response to higher in vitro passages, and specifically in progressing from passage 106 to passage 135 vaccine.

Example 5

Minimum Immunizing Doses

Materials and Methods

An *M. bovis*, avirulent live bacterial culture in lyophilized presentation that was rehydrated with sterile water diluent was used at 2×2 mL doses administered at 2 to 3 week intervals via subcutaneous injection in cattle 6 weeks of age or older.

The study design utilized 3 vaccine treated groups and 1 placebo treated each containing 15 to 17 calves. Test animals all received two subcutaneous doses of experimental vaccines formulated at 3 different antigen levels or a placebo vaccine composed of the media used to produce the *Mycoplasma Bovis* culture. Calves were 6-weeks of age at the time of administration of the first dose of vaccine or placebo. Calves were challenged on day 42 and post-challenge observations were made for 28 days. Primary parameters of mortality/culling, and lameness and joint swelling on any day were observed to assess the efficacy of the vaccine.

Table 12 summarizes the conclusions made from the analysis of the data.

TABLE 12

Minimum Immunizing Doses

| Variable | Treatment | No. of calves | Prevented Fraction | Lower 95% CL | Upper 95% CL | Conclusion |
|---|---|---|---|---|---|---|
| Mortality/ Culling | Low Dose = $10^{6.8}$/dose | 16 | 0.04 | −0.859 | 0.5113 | Incomplete Efficacy |
| | Middle Dose = $10^{7.9}$/dose | 15 | 0.1467 | −0.631 | 0.6163 | Incomplete Efficacy |
| | High Dose = $10^{8.9}$/dose | 17 | 0.6235 | 0.0855 | 0.9268 | Efficacy Established |
| | Placebo | 15 | | | | |
| Presence of Lameness | Low Dose = $10^{6.8}$/dose | 16 | 0.2857 | −0.1 | 0.5994 | Incomplete Efficacy |
| | Middle Dose = $10^{7.9}$/dose | 15 | 0.0857 | −0.324 | 0.4046 | Incomplete Efficacy |
| | High Dose = $10^{8.9}$/dose | 17 | 0.6667 | 0.3653 | 0.8513 | Efficacy Established |
| | Placebo | 15 | | | | |
| Presence of Swelling | Low Dose = $10^{6.8}$/dose | 16 | 0.1818 | −0.468 | 0.5908 | Incomplete Efficacy |
| | Middle Dose = $10^{7.9}$/dose | 15 | 0.0303 | −0.693 | 0.4606 | Incomplete Efficacy |
| | High Dose = $10^{8.9}$/dose | 17 | 0.5722 | 0.0498 | 0.866 | Efficacy Established |
| | Placebo | 15 | | | | |

Conclusions

A preferred dose of $10^{8.9}$ $CCU_{50}$ was efficacious as assessed.

Example 6

Safety—Dissemination and Transmission

Materials and Methods

An *M. bovis*, avirulent live bacterial culture in lyophilized presentation that was rehydrated with sterile water diluent was used at 2×2 mL doses administered at 2 to 3 week intervals via subcutaneous injection in cattle 6 weeks of age or older.

The dissemination and transmission of the vaccine strain was also evaluated in colostrum deprived calves. In this study >10 logs of low passage, Master seed-derived (MS+3) was administered via the subcutaneous route to 10 calves. Samples including 15 different tissues and swabs were collected from treated calves at weekly intervals for 5 weeks after administration. To assess transmission of the vaccine, 10 sentinel calves were comingled with the vaccinated calves throughout the study. Table 13 shows the results of this study.

TABLE 13

Summary of experimental design and results of dissemination and transmission

| Treatment | Administration | No. of calves | Dose | Outcome |
|---|---|---|---|---|
| *Mycoplasma bovis* working seed (MS + 3) | Subcutaneous injection | 10 | $10^{10.5}$/dose | No *M. bovis* isolated beyond 14 days post vaccination. No lesions or clinical signs |
| Commingled w/ treated calves | Animal to animal contact | 10 | Sentinels | No *M. bovis* detected. No lesions or clinical signs |

Conclusions

The 14 day sampling was the only recovery of *Mycoplasma bovis* vaccine, avirulent live culture, and only in one tonsil tissue sample from a single calf in the vaccinated group. The remaining 129 samples collected from dosed calves from day 7 through day 35 after vaccination were all negative for *M. bovis*.

Within this study, an equal number of sentinel calves were commingled with the vaccinated calves. No *M. bovis* was isolated from any of the swab samples or tissues from the sentinel calves.

The data from Examples 5 and 6 demonstrated the safety and efficacy of the vaccine of the present invention. The vaccines of the present invention were highly effective in preventing disease due to *M. bovis* following two subcutaneous injections at the minimum immunizing dose ($10^{8.9}$/dose). The safety evaluations in young, highly susceptible colostrum deprived (CD) calves confirmed the safety of a 20-fold overdose injected subcutaneously. The safety studies also demonstrated the vaccine is safe when injected subcutaneously.

Example 7

Preparation of Combination Vaccines

Vaccine A

*M. bovis*, IBR, and BVDV Types 1 and 2

Attenuated live BVDV type 1 and 2 strains, having at least one mutation in the coding sequence for glycoprotein $E^{rns}$ and/or at least another mutation in the coding sequence for $N^{pro}$, wherein said mutation in the coding sequence for glycoprotein $E^{rns}$ leads to inactivation of RNase activity residing in $E^{rns}$ and/or said mutation in the coding sequence for $N^{pro}$ leads to inactivation of said $N^{pro}$ (as described in WO2005/111201, hereby entirely incorporated by reference), are grown in MDBK-cells until a $TCID_{50}$ of about $10^{5.0}$ to $10^{8.1}$ per ml cell culture fluid. A live attenuated strain of IBR is grown in MDBK cells until a $TCID_{50}$ of about $10^{5.0}$ to $10^{8.6}$ per ml cell culture fluid. A live attenuated strain of *M. bovis* as described above is grown in MDBK cells until a CFU of about $10^{10}$ per ml cell culture fluid. Each culture fluids are collected. Equal amounts of the antigens are mixed and lyophilized by standard techniques. For reconstitution, an aqueous solution is used. One dose of the combination vaccine contains 2 ml of the reconstituted antigens. A final dose includes IBR ($10^{5.0}$ to $10^{8.6}$ $TCID_{50}$), BVDV-1 ($10^{5.0}$ to $10^{8.1}$ $TCID_{50}$), BVDV-2 ($10^{5.0}$ to $10^{8.1}$ $TCID_{50}$), and *M. bovis* ($2.1\times10^{9\cdot}$ CFU).

Vaccine B

*M. bovis*, IBR, BVDV types 1 and 2, and PI3

The preparation of the IBR, BVDV 1 and 2 and *M. bovis* antigens are grown as described for vaccine A. In addition, a live attenuated strain of PI3 is grown in MDBK cells until a $TCID_{50}$ of about $10^{4.2}$ to $10^{6.5}$ per ml cell culture fluid. Afterwards, the PI3 containing culture fluid is harvested. An amount of $10^{4.2}$ to $10^{6.5}$ ($TCID_{50}$) of the PI3 antigen is mixed with the IBR, and BVDV types 1 and 2. The mixture is then lyophilized by standard techniques, so that one dose of the reconstituted combination vaccine contains 2 ml as described for Vaccine A. A final dose includes IBR ($10^{5.0}$ to $10^{8.6}$ $TCID_{50}$), BVDV-1 ($10^{5.0}$ to $10^{8.1}$ $TCID_{50}$), BVDV-2 ($10^{5.0}$ to $10^{8.1}$ $TCID_{50}$), *M. bovis* ($2.1\times10^{9\cdot}$ CFU), and PI3 ($10^{4.2}$ to $10^{6.5}$ $TCID_{50}$).

Vaccine C

*M. bovis*, BVDV types 1 and 2, PI3, *Mannheimia* (*Pasteurella*) *haemolytica*

BVDV 1 and 2, *M. bovis* bacterium according to the present invention, and PI3 viruses are grown as described for vaccines A and B. After the culture fluids are harvested, the antigens are lyophilized. *Mannheimia* (*Pasteurella*) *haemolytica* is grown until the titer reaches $10^{8.0}$ to $10^{11}$ cells per ml of culture. The bacteria are inactivated and the culture fluid is lyophilized or freeze dried, or formulated as a liquid that will not inactivate attenuated cultures of BVD, *M. bovis*, and PI3. An amount of $10^{8.0}$ to $10^{11.0}$ lyophilized or freeze dried or formulated liquid bacteria cells are mixed with the lyophilized BVDV types 1 and 2 antigen (each in an amount of $10^{5.0}$ to $10^{8.1}$ $TCID_{50}$), PI3 antigen ($10^{7.3}$ to $10^{8.3}$ $TCID_{50}$) and *M. bovis* antigen ($2.1\times10^{9}$ CFU). Final antigen amounts per dose are BVDV-1 ($10^{5.0}$ to $10^{8.1}$ $TCID_{50}$), BVDV-2 ($10^{5.0}$ to $10^{8.1}$ $TCID_{50}$), PI3 ($10^{7.3}$ to $10^{8.3}$ $TCID_{50}$) *M. bovis* ($2.1\times10^{9}$CFU), and *Mannheimia* (*Pasteurella*) *haemolytica* ($10^{8.0}$ to $10^{11.0}$ cells).

Vaccine D

*M. bovis* BVDV types 1 and 2, IBR, PI3, *Leptospira canicola, Leptospira grippotyphosa, Leptospira hardjo, Leptospira pomoma, Leptospira borgpetersenii hardjo-bovis*

BVDV 1 and 2, *M. bovis*, IBR, and PI3 are grown as described for vaccines A and B. After the culture fluids are harvested, the viruses and *M. bovis* are lyophilized. *Leptospira canicola, Leptospira grippotyphosa, Leptospira hardjo, Leptospira pomoma, Leptospira borgpetersenii hardjo-bovis* are separately cultivated until reaching $10^{8.0}$ to $10^{11.0}$ cells per ml of culture. The *Leptospira* cultures are inactivated and the culture fluids are lyophilized or freeze dried, or formulated as a liquid that is non-virucidal for the live antigens of the vaccine. Each of the $10^{8.0}$ to $10^{11.0}$ of the lyophilised or freeze dried bacteria cells are reconstituted with the lyophilized modified BVDV types 1 and 2 (each in an amount of $10^{5.0}$ to $10^{7.0}$ $TCID_{50}$), modified live PI3 ($10^{7.3}$ to $10^{8.3}$ $TCID_{50}$), modified live *M. bovis* ($2.1\times10^{9}$ CFU) and modified live IBR ($10^{6.1}$ to $10^{7.7}$ $TCID_{50}$) using sterile water for injection, or the lyophilized components are reconstituted using the liquid non-virucidal formulation of the *Leptospira* cultures. The reconstituted suspension (2 ml per dose) contains traces of neomycin as preservative. Final antigen amounts per dose are BVDV-1 ($10^{5.0}$ to $10^{7.0}$ $TCID_{50}$), BVDV-2 ($10^{5.0}$ to $10^{7.0}$ $TCID_{50}$), PI3 ($10^{7.3}$ to $10^{8.3}$ $TCID_{50}$) *M. bovis* ($2.1\times10^{9}$ CFU), PI3 ($10^{7.3}$ to $10^{8.3}$ $TCID_{50}$), and *Leptospira canicola, Leptospira grippotyphosa, Leptospira hardjo, Leptospira pomoma*, and *Leptospira borgpetersenii hardjo-bovis* (each $10^{8.0}$ to $10^{11.0}$ cells).

Vaccine E

*M. bovis*, BVDV types 1 and 2, IBR, PI3, and *H. somnus*

BVDV 1 and 2, *M. bovis*, IBR, and PI3 are grown as described for vaccines A and B. After the culture fluids are harvested, the viruses and *M. bovis* are lyophilized. *H. somnus* is cultivated until achieving $10^{7.1}$ to $10^{9.2}$ cells per ml culture. The bacteria culture is inactivated and the culture fluid is lyophilized or freeze dried, or formulated as a liquid that is non-virucidal for the live antigens of the vaccine. $10^{7.1}$ to $10^{9.2}$ of the lyophilized or freeze dried bacteria are reconstituted with the lyophilized modified BVDV types 1 and 2 (each in an amount of $10^{5.0}$ to $10^{7.0}$ $TCID_{50}$), modified live PI3 ($10^{7.3}$ to $10^{8.3}$ $TCID_{50}$), modified live *M. bovis* ($2.1\times10^9$ CFU), and modified live IBR ($10^{6.1}$ to $10^{7.7}$ $TCID_{50}$) using sterile water for injection, or the lyophilized components are reconstituted using the liquid non-virucidal formulation of the bacterial *H. somnus* culture. The reconstituted suspension (2 ml per dose) contains traces of neomycin as preservative. Final antigen amounts per dose are BVDV-1 ($10^{5.0}$ to $10^{7.0}$ $TCID_{50}$), BVDV-2 ($10^{5.0}$ to $10^{7.0}$ $TCID_{50}$), PI3 ($10^{7.3}$ to $10^{8.3}$ $TCID_{50}$) *M. bovis* ($2.1\times10^9$ CFU), PI3 ($10^{7.3}$ to $10^{8.3}$ $TCID_{50}$), and *H. somnus* ($10^{7.1}$ to $10^{9.2}$ cells).

Vaccine F

*M. bovis*, IBR, BVDV types 1 and 2, PI3 and BRSV

The preparation of the IBR, PI3, BVDV 1 and 2 and *M. bovis* antigens are grown as described for vaccine A and B. In addition, a live attenuated strain of BRSV is grown in MDBK cells until a $TCID_{50}$ of about $10^{5.0}$ to $10^{7.2}$ per ml cell culture fluid. Afterwards, the BRSV containing culture fluid is harvested. After the culture fluids are harvested, the antigens are mixed and lyophilized as described for vaccine A and B. An amount of $10^{5.0}$ to $10^{7.2}$ of the BRSV antigen is mixed with the IBR, BVDV types 1 and 2, and *M. bovis* antigens. The mixture is then reconstituted in 2 ml dose volume as described for Vaccine A. For reconstitution, an aqueous solution is used. One dose of the combination vaccine contains 2 ml of the reconstituted antigens. A final dose includes IBR ($10^{5.0}$ to $10^{8.6}$ $TCID_{50}$), BVDV-1 ($10^{5.0}$ to $10^{8.1}$ $TCID_{50}$), BVDV-2 ($10^{5.0}$ to $10^{8.1}$ $TCID_{50}$), *M. bovis* ($2.1\times10^9$ CFU), PI3 ($10^{4.2}$ to $10^{6.5}$ $TCID_{50}$) and BRSV ($10^{5.0}$ to $10^{7.2}$ $TCID_{50}$).

The invention claimed is:

1. An attenuated, avirulent *Mycoplasma bovis* (*M. bovis*) bacterium strain, wherein the bacterium is passaged more than 110 times and wherein the attenuated, avirulent *M. bovis* strain is selected from the group consisting of:

a. the attenuated *M. bovis* bacteria strain deposited with the American Type Culture Collection (ATCC) under accession number PTA-9666, and b. the attenuated *M. bovis* bacteria strain deposited with the ATCC under accession number PTA-9667.

2. The attenuated, avirulent *M. bovis* bacterium strain according to claim 1, wherein the bacterium is passaged more than 135 times.

3. A method of attenuating *M. bovis*, comprising, a. passaging *M. bovis* bacteria according to claim 1 more than 110 times to produce a cultured *M. bovis* bacteria;

b. obtaining the cultured *M. bovis* bacteria;

c. testing the cultured *M. bovis* bacteria obtained under step b) for their pathogenicity and immunogenicity; and d. propagating the non-pathogenic, but immunogenic *M. bovis* bacteria to obtain the attenuated *M. bovis* bacteria.

4. The method according to claim 3, wherein the *M. bovis* bacteria are passaged in vitro.

5. The method according to claim 3, wherein the pathogenicity testing comprises:

e. infecting cattle with the passaged *M. bovis* bacteria; and f. monitoring the infected cattle for developing clinical symptoms of a *M. bovis* infection and monitoring the development of the humoral antibody response against *M. bovis* in the infected cattle.

6. The attenuated, avirulent *M. bovis* bacterium strain according to claim 1, wherein the bacterium strain comprises at least 1.0E7 CFU of the live bacteria of the attenuated, avirulent *M. bovis* bacteria per dose.

7. The attenuated, avirulent *M. bovis* bacterium strain according to claim 1, wherein one dose is 1 or 2 ml.

8. A method for the treatment or prophylaxis of infections caused by *M. bovis*, comprising, administering an effective amount of the attenuated, avirulent *M. bovis* bacterium strain according to claim 1 to an animal, wherein said treatment or prophylaxis is selected from the group consisting of reducing signs of *M. bovis* infection, reducing the severity of or incidence of clinical signs of *M. bovis* infection, reducing the mortality of animals from *M. bovis* infection, and combinations thereof.

9. The method according to claim 8, wherein only a single dose is administered to said animal.

10. The method according to claim 8, wherein the attenuated, avirulent *M. bovis* bacterium strain is administered to animals from day 1 of age.

11. The method according to claim 8, wherein two doses are administered to said animal.

12. The method according to claim 11, wherein a second dose is administered at least 10 days after the first administration.

13. The method according to claim 8, wherein the animal is cattle.

14. A method for reducing the incidence of mortality and/or euthanasia of animals resulting from infection by *M. bovis* comprising administering the attenuated, avirulent *M. bovis* bacterium strain of claim 1 to an animal.

15. The method of claim 14, wherein said mortality is reduced by at least 56%.

16. The method of claim 14, wherein said attenuated, avirulent *M. bovis* bacterium strain is administered as a single dose.

17. An attenuated, avirulent *M. bovis* bacterium strain for the treatment and/or prophylaxis of cattle against microbiological infections, wherein said immunogenic composition comprises at least one *M. bovis* bacteria according to claim 1; and one or more further immunologically active component (s) effective for the treatment and/or prophylaxis of microbiological infection in cattle caused by a cattle pathogen other than *M. bovis*.

18. The attenuated, avirulent *M. bovis* bacterium strain according to claim 17, wherein said microbiological infection in cattle caused by a cattle pathogen other than *M. bovis* is caused by one or more immunogenic components selected from the group consisting of: Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (BPV), Adenovirus Astrovirus, *Mannheimia haemolytica* (formerly

*Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus* fetus (formerly *C. fetus intestinalis*), *Leptospira interrogans, Leptospira hardjo, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Streptococcus agalactiae, Escherichia coli, Mycoplasma* spp, *Mycoplasma dispar*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis, Dictyocaulus viviparous* (Lungworm disease), and combinations thereof.

19. The attenuated, avirulent *M. bovis* bacterium strain according to claim 17, wherein said immunogenic composition is a single-dose administration.

20. A method of co-administration of two or more immunologically active components to a cattle comprising, administering to said cattle an attenuated, avirulent *M. bovis* bacterium strain according to claim 1, and one or more further immunologically active component(s) effective for the treatment and/or prophylaxis of infections caused by a further cattle relevant pathogen other than *M. bovis*.

21. The method according to claim 20, wherein said attenuated, avirulent *M. bovis* bacterium strain and said immunologically active component(s) are administered separately.

22. The method according to claim 20, wherein the separate co-administration of the attenuated, avirulent *M. bovis* bacterium strain and said immunologically active component (s) occurs within 2 days.

23. The method according to claim 20, wherein the two or more immunologically active components which comprise an attenuated, avirulent *M. bovis* bacterium strain and one or more immunologically active component(s) effective for the treatment and/or prophylaxis of infections caused by a further cattle relevant pathogen other than *M. bovis* are formulated as fix-dose combination vaccine.

24. The method according to claim 20, wherein the two or more immunologically active components which comprise an attenuated, avirulent *M. bovis* bacterium strain and one or more immunologically active component(s) effective for the treatment and/or prophylaxis of infections caused by a further cattle relevant pathogen other than *M. bovis* are administered to said cattle in one only dose.

* * * * *